United States Patent
Lim et al.

(10) Patent No.: US 10,381,570 B2
(45) Date of Patent: Aug. 13, 2019

(54) COMPOUND AND ORGANIC LIGHT-EMITTING DEVICE INCLUDING THE SAME

(71) Applicant: SAMSUNG DISPLAY CO., LTD., Yongin-si, Gyeonggi-Do (KR)

(72) Inventors: Jino Lim, Yongin-si (KR); Youngkook Kim, Yongin-si (KR); Jongwoo Kim, Yongin-si (KR); Hyungseok Jang, Yongin-si (KR); Seokhwan Hwang, Yongin-si (KR)

(73) Assignee: SAMSUNG DISPLAY CO., LTD., Yongin-si, Gyeonggi-do (KR)

( * ) Notice: Subject to any disclaimer, the term of this patent is extended or adjusted under 35 U.S.C. 154(b) by 538 days.

(21) Appl. No.: 14/886,122

(22) Filed: Oct. 19, 2015

(65) Prior Publication Data

US 2016/0301004 A1    Oct. 13, 2016

(30) Foreign Application Priority Data

Apr. 7, 2015 (KR) .................. 10-2015-0049076

(51) Int. Cl.
| | |
|---|---|
| *H01L 51/54* | (2006.01) |
| *C09K 11/06* | (2006.01) |
| *H01L 51/00* | (2006.01) |
| *C07C 211/54* | (2006.01) |
| *C07C 211/58* | (2006.01) |
| *C07D 213/74* | (2006.01) |
| *C07D 307/91* | (2006.01) |
| *H01L 51/50* | (2006.01) |

(52) U.S. Cl.
CPC .......... *H01L 51/006* (2013.01); *C07C 211/54* (2013.01); *C07C 211/58* (2013.01); *C07D 213/74* (2013.01); *C07D 307/91* (2013.01); *C09K 11/06* (2013.01); *H01L 51/0061* (2013.01); *H01L 51/0077* (2013.01); *C07C 2603/52* (2017.05); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *C09K 2211/185* (2013.01); *H01L 51/0055* (2013.01); *H01L 51/0058* (2013.01); *H01L 51/0067* (2013.01); *H01L 51/0073* (2013.01); *H01L 51/506* (2013.01); *H01L 51/5056* (2013.01); *H01L 51/5072* (2013.01); *H01L 51/5076* (2013.01)

(58) Field of Classification Search
CPC ... C07C 211/43; C07C 211/44; C07C 211/45; C07C 211/46; C07C 211/54; C07C 211/58; C07C 2603/00; C07C 2603/52; C07D 213/74; C07D 307/91; C09K 11/06; C09K 2211/00; C09K 2211/10; C09K 2211/1003; C09K 2211/1007; C09K 2211/1011; C09K 2211/1014; C09K 2211/1029; C09K 2211/1088; C09K 2211/1092; C09K 2211/185; H01L 51/0032; H01L 51/005; H01L 51/0051; H01L 51/0052; H01L 51/0055; H01L 51/0058; H01L 51/0059; H01L 51/006; H01L 51/0061; H01L 51/0065; H01L 51/0067; H01L 51/0068; H01L 51/0072; H01L 51/0073; H01L 51/0074; H01L 51/0077; H01L 51/0079; H01L 51/50; H01L 51/5012; H01L 51/5016; H01L 51/5056; H01L 51/506; H01L 51/5072; H01L 51/5076
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

| | | | |
|---|---|---|---|
| 6,465,115 B2 | 10/2002 | Shi et al. | |
| 6,596,415 B2 | 7/2003 | Shi et al. | |

(Continued)

FOREIGN PATENT DOCUMENTS

| | | | |
|---|---|---|---|
| JP | 2006-151844 A | 6/2006 | |
| KR | 10-2009-0008367 A | 1/2009 | |

(Continued)

OTHER PUBLICATIONS

Machine translation of JP2006-141844. (Year: 2006).*

(Continued)

*Primary Examiner* — Andrew K Bohaty
(74) *Attorney, Agent, or Firm* — Lee & Morse, P.C.

(57) ABSTRACT

A compound represented by Formula 1, below, an organic light-emitting device including the compound represented by Formula 1, below, in an organic layer between a first electrode and a second electrode, and a display device including the organic light emitting device including the compound represented by Formula 1, below:

<Formula 1>

(Continued)

18 Claims, 1 Drawing Sheet

(56) References Cited

U.S. PATENT DOCUMENTS

| | | |
|---|---|---|
| 2009/0079344 A1 | 3/2009 | Saitoh et al. |
| 2010/0295029 A1 | 11/2010 | Kawamura |
| 2012/0326133 A1 | 12/2012 | Kim et al. |
| 2015/0034924 A1 | 2/2015 | Yokoyama et al. |

FOREIGN PATENT DOCUMENTS

| | | | |
|---|---|---|---|
| KR | 10-2010-0088613 A | | 8/2010 |
| KR | 20110085784 A | * | 7/2011 |
| KR | 10-2013-0000230 A | | 1/2013 |
| KR | 10-2014-0084051 A | | 7/2014 |
| WO | WO-2013061805 A1 | * | 5/2013 ........... C07C 211/54 |

OTHER PUBLICATIONS

Machine translation of KR2011-085784. (Year: 2011).*
Extended European Search Report dated Aug. 18, 2016 in Corresponding European Patent Application No. 15196175.2.

\* cited by examiner

10

| 190 |
| :---: |
| 150 |
| 110 |

COMPOUND AND ORGANIC LIGHT-EMITTING DEVICE INCLUDING THE SAME

CROSS-REFERENCE TO RELATED APPLICATION

Korean Patent Application No. 10-2015-0049076, filed on Apr. 7, 2015, in the Korean Intellectual Property Office, and entitled: "Compound and Organic Light-Emitting Device Comprising the Same," is incorporated by reference herein in its entirety.

BACKGROUND

1. Field

Embodiments relate to a compound and an organic light-emitting device including the compound.

2. Description of the Related Art

Organic light-emitting devices (OLEDs) are self-emitting devices that have advantages such as wide viewing angles, excellent contrast, quick response, high brightness, excellent driving voltage characteristics, and can provide multicolored images.

An organic light-emitting device may have a structure in which a first electrode, a hole transport region, an emission layer, an electron transport region, and a second electrode are sequentially disposed in this order on a substrate. Holes injected from the first electrode move to the emission layer via the hole transport region, while electrons injected from the second electrode move to the emission layer via the electron transport region. Carriers such as the holes and electrons recombine in the emission layer to generate excitons. When the excitons drop from an excited state to a ground state, light is emitted.

SUMMARY

Embodiments are directed to a compound and an organic light-emitting device including the compound.

The embodiments may be realized by providing a compound represented by Formula 1:

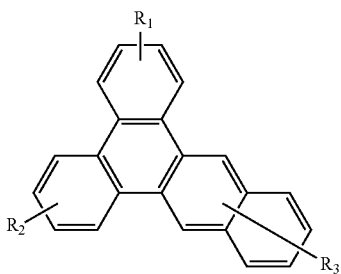

<Formula 1> wherein, in Formula 1, $R_1$ to $R_3$ are each independently selected from a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and a group represented by Formula 1-1; and at least one of $R_1$ to $R_3$ is a group represented by Formula 1-1:

<Formula 1-1> wherein, in Formula 1-1, X is selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group; m is an integer of 1 to 3, a plurality of Xs being the same or different when m is 2 or 3; and $Ar_1$ and $Ar_2$ are each independently selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, wherein at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ arylene group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroarylene group, the substituted monovalent non-aromatic condensed polycyclic group, the substituted monovalent non-aromatic condensed heteropolycyclic group, the substituted divalent non-aromatic condensed polycyclic group, and the substituted divalent non-aromatic condensed heteropolycyclic group is selected from: a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), wherein $Q_{11}$ to $Q_{17}$ and $Q_{21}$ to $Q_{27}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group; and a plurality of Xs are the same or differs when m is 2 or greater.

In Formula 1-1, X may be a substituted or unsubstituted $C_6$-$C_{60}$ arylene group or a substituted or unsubstituted $C_1$-$C_{60}$ heteroarylene group.

In Formula 1-1, X is a group represented by one of Formulae 2a, 2b, and 2c:

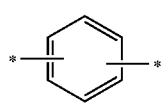

2a

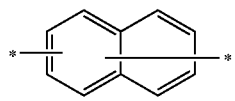

2b

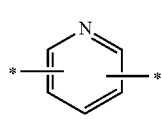

2c wherein, in Formulae 2a, 2b, and 2c, * indicates a binding site to an adjacent atom.

In Formula 1, $Ar_1$ and $Ar_2$ may each independently be a substituted or unsubstituted $C_6$-$C_{60}$ aryl group or a substituted or unsubstituted $C_1$-$C_{60}$ heteroaryl group.

In Formula 1, $Ar_1$ and $Ar_2$ may each independently be a group represented by one of Formulae 3a, 3b, and 3c:

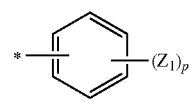

3a

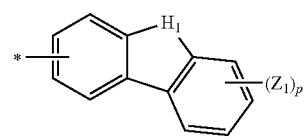

3b

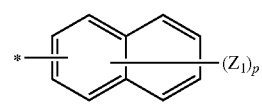

3c wherein, in Formulae 3a, 3b, and 3c, $H_1$ may be O or S; $Z_1$ may be selected from a hydrogen, a deuterium, a substituted or unsubstituted C1-C20 alkyl group, a substituted or unsubstituted C6-C20 aryl group, a substituted or unsubstituted C1-C20 heteroaryl group, a substituted or unsubstituted monovalent non-aromatic condensed polycyclic group, and a substituted or unsubstituted monovalent non-aromatic condensed heteropolycyclic group; p may be an integer of 1 to 7; and * indicates a binding site to a neighboring atom.

$Z_1$ may be a hydrogen, a deuterium, or a group represented by Formula 4a:

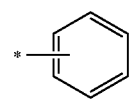

4a wherein, in Formula 4a, * indicates a binding site to a neighboring atom.

The compound represented by Formula 1 may be represented by Formula 2:

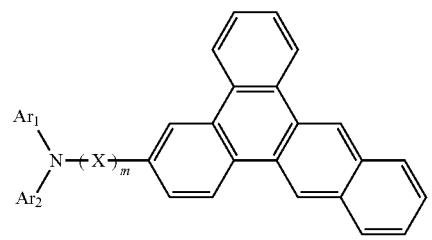

<Formula 2> wherein, in Formula 2, X, m, $Ar_1$, and $Ar_2$ are defined the same as X, m, $Ar_1$, and $Ar_2$ of Formula 1.

The compound represented by Formula 1 may be represented by Formula 3:

<Formula 3>
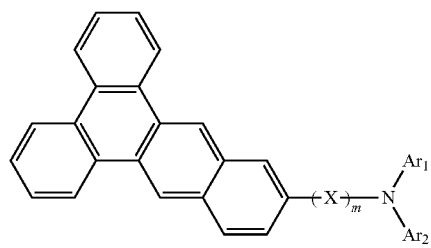
wherein, in Formula 3, X, m, $Ar_1$, and $Ar_2$ are defined the same as X, m, $Ar_1$, and $Ar_2$ of Formula 1.
The compound represented by Formula 1 may be one of the following Compounds 1 to 44, 46, and 47:
1
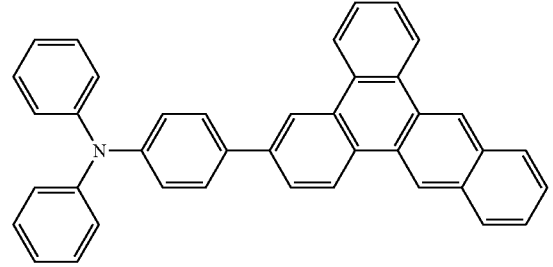
2
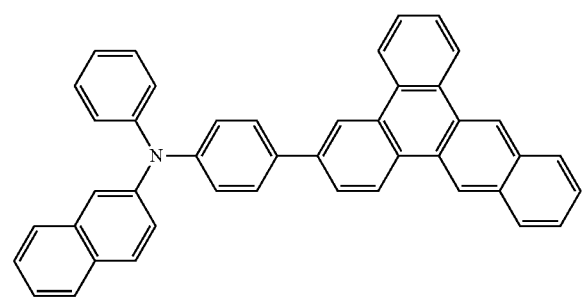
3
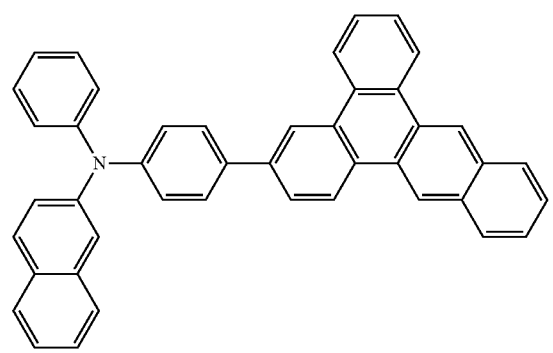
4
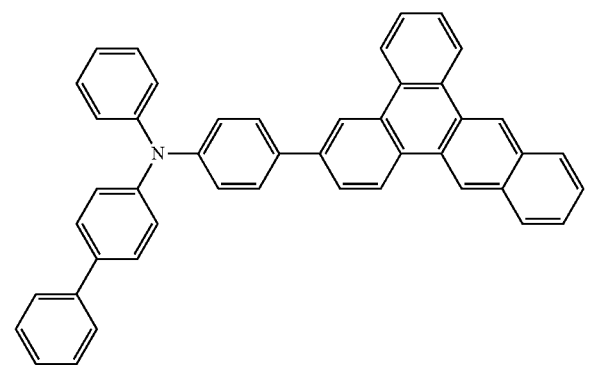
5
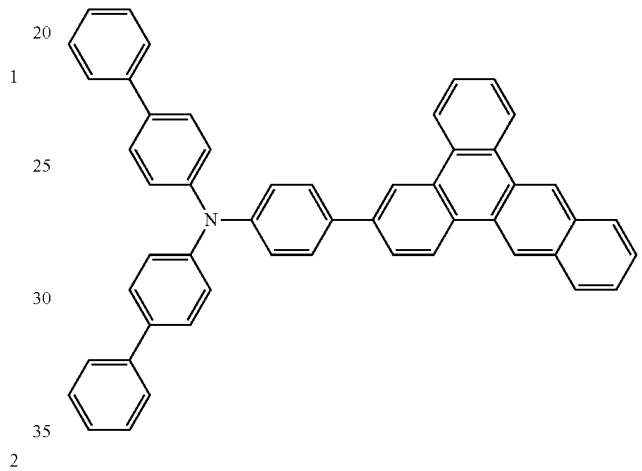
6
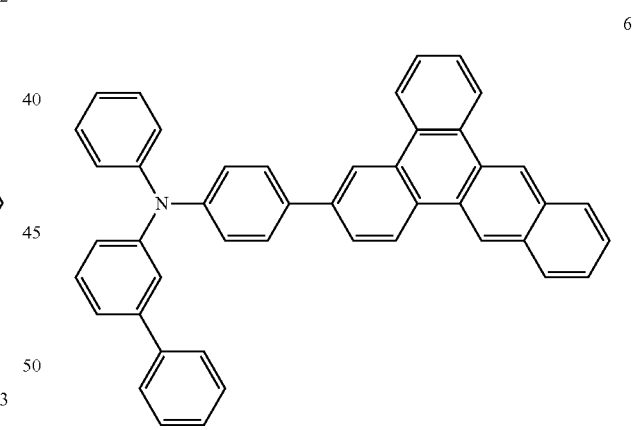
7
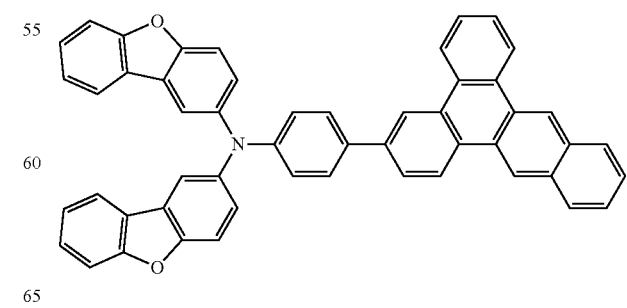

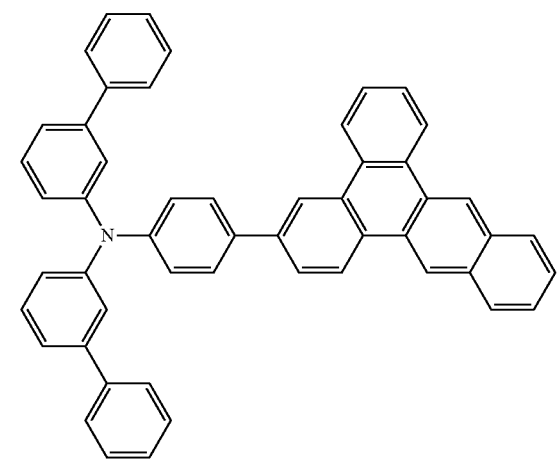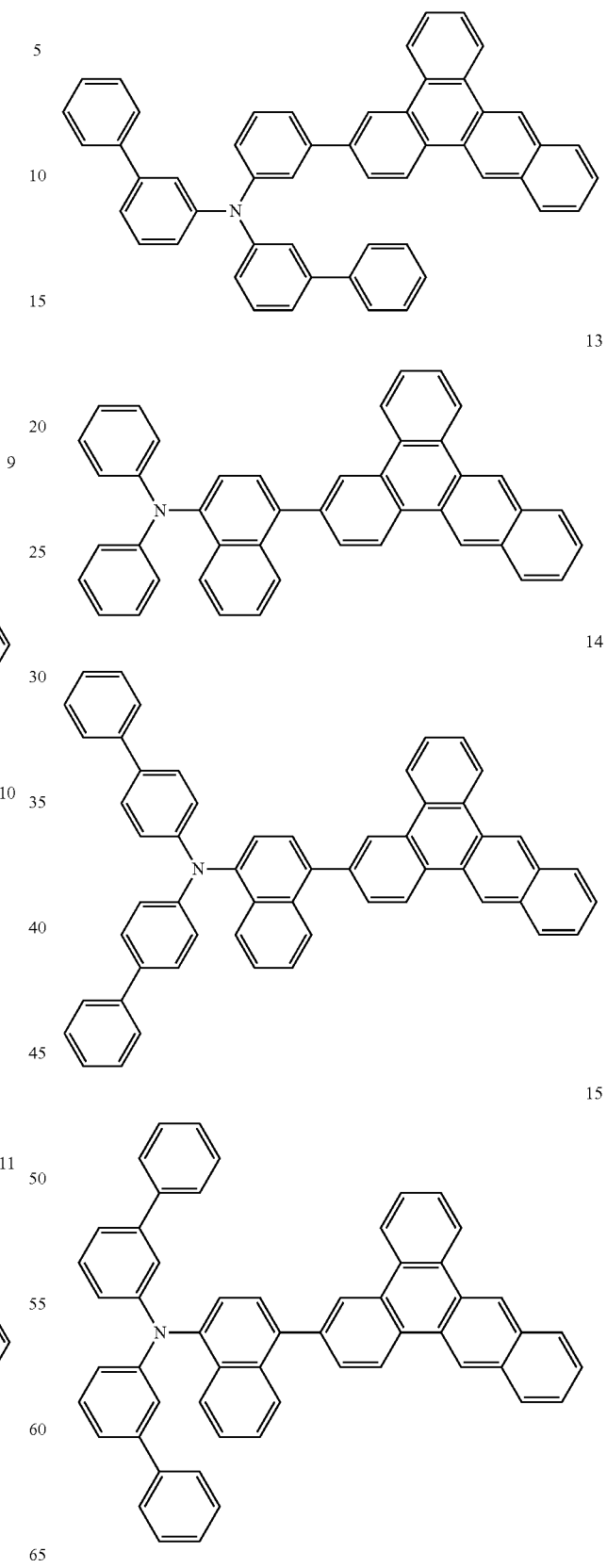

16
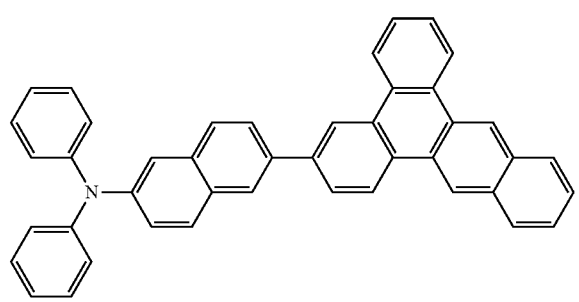
17
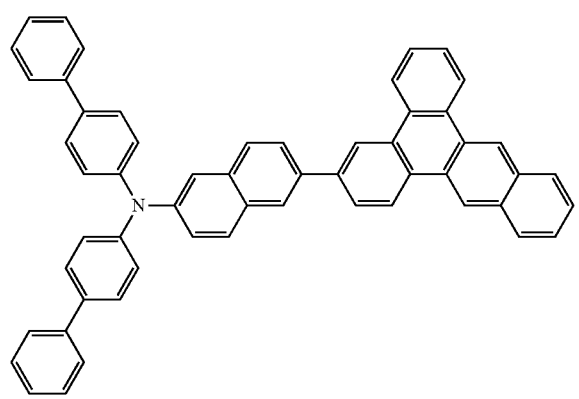
18
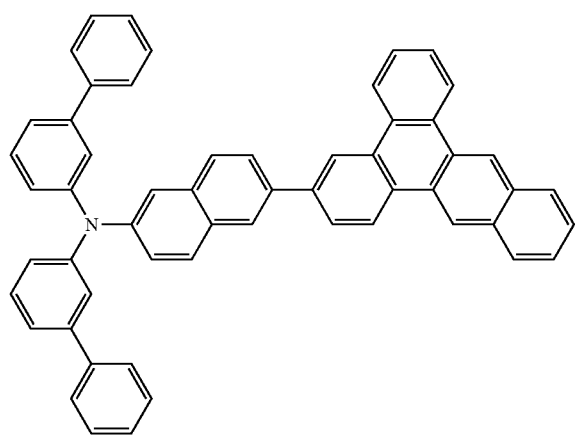
19
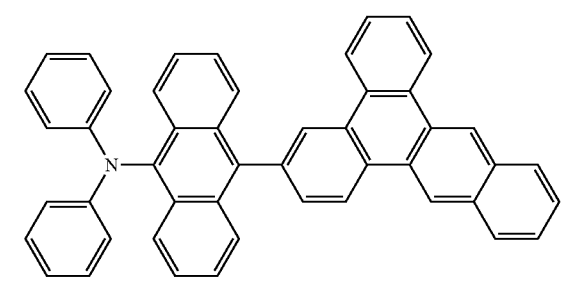
20
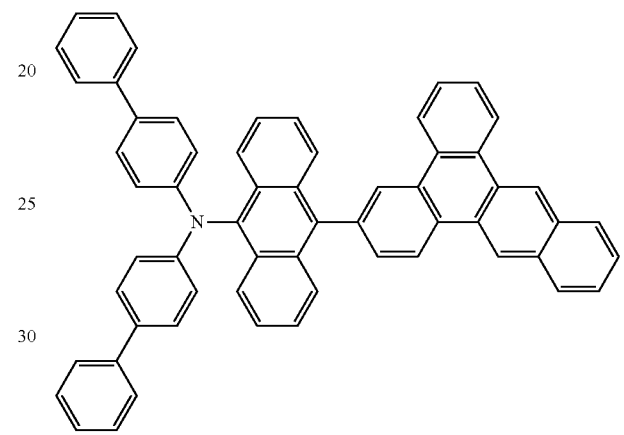
21
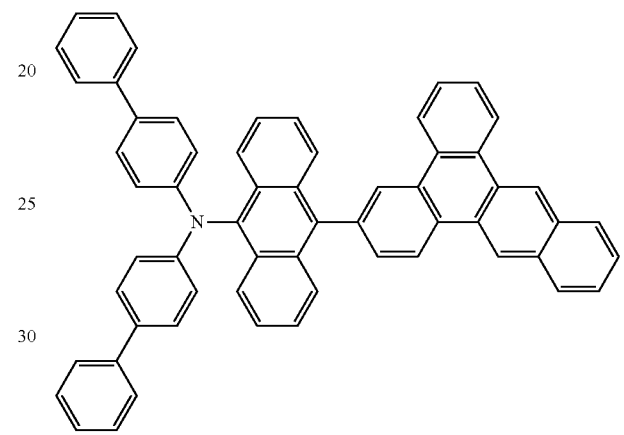
22
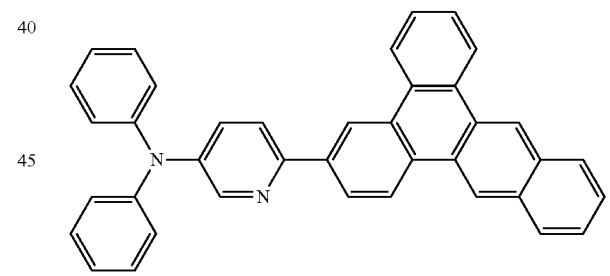
23
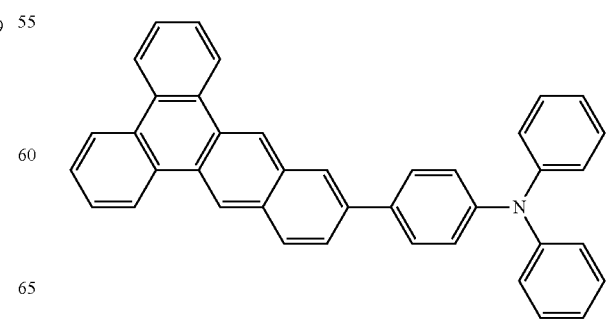

24
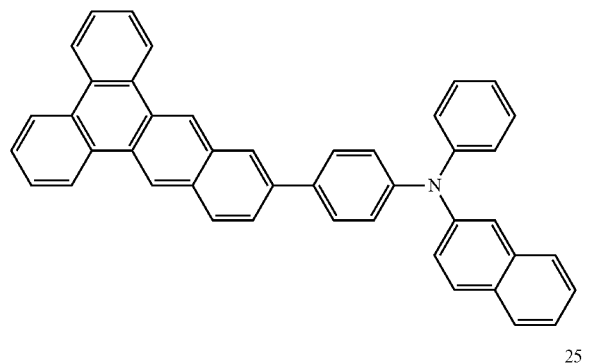
25
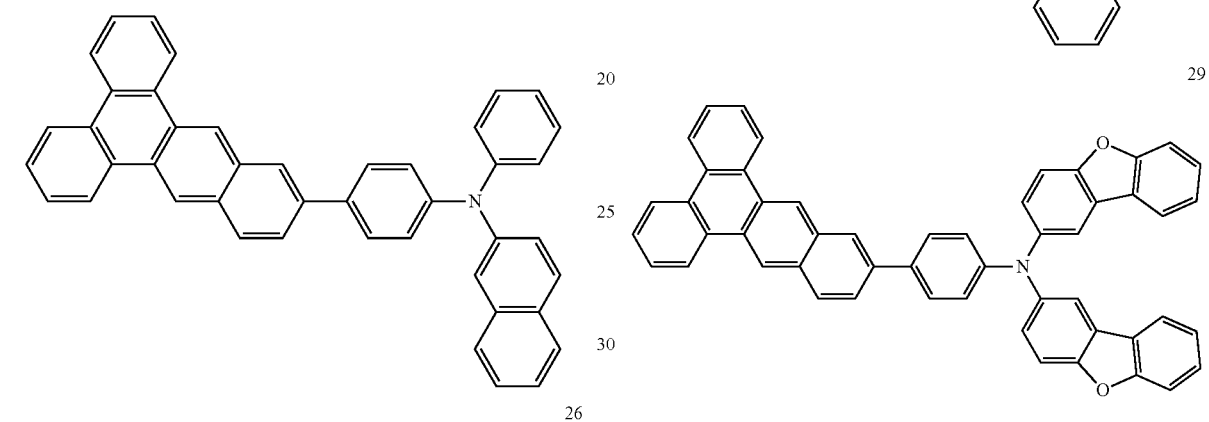
26
27
28
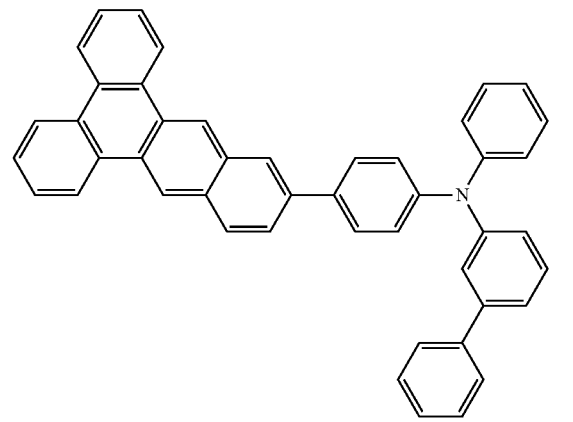
29
30
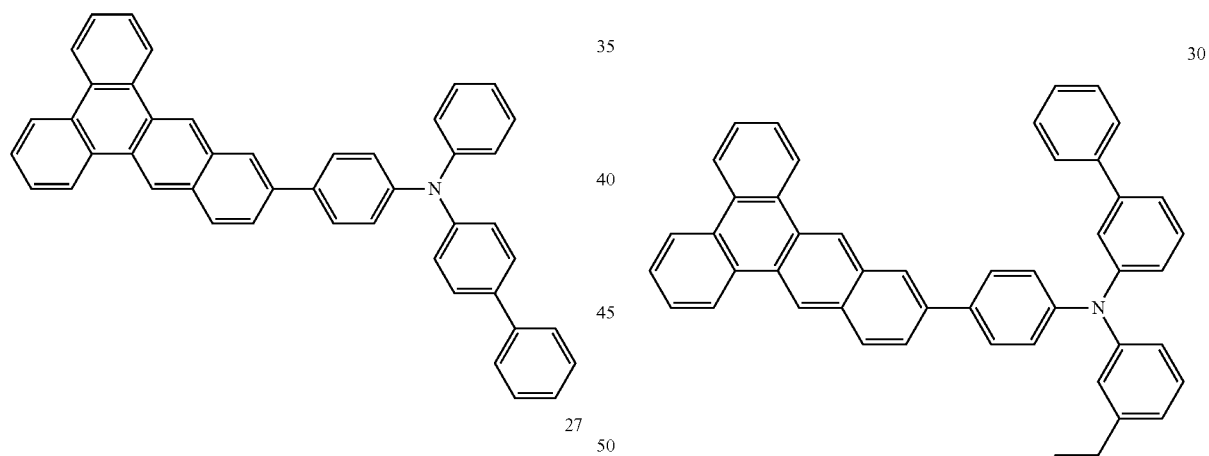
31
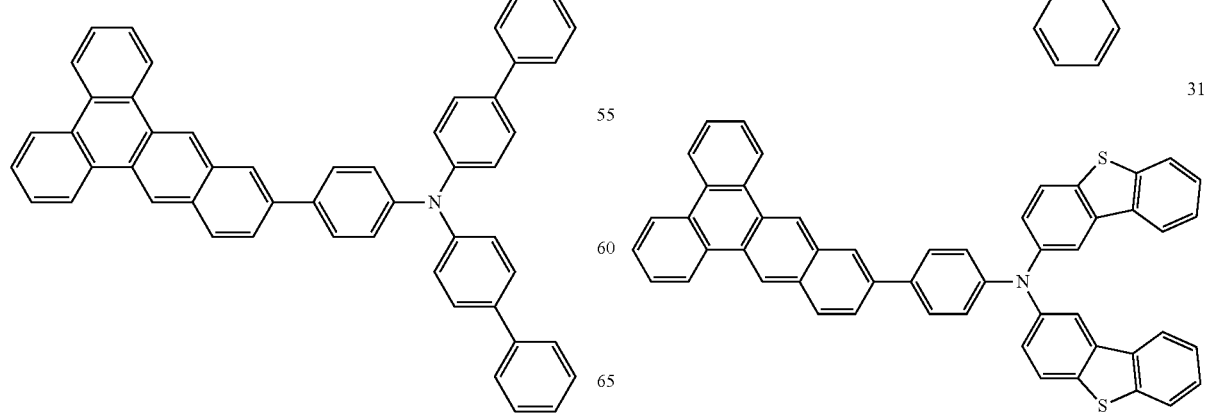

32
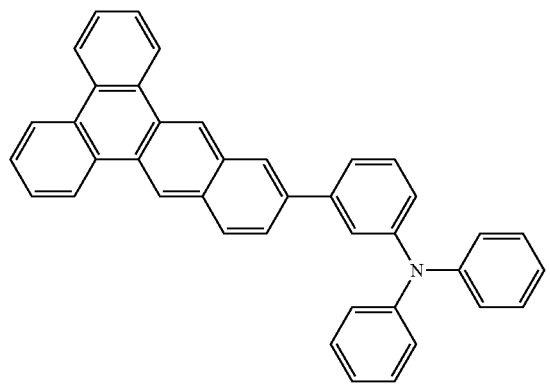
33
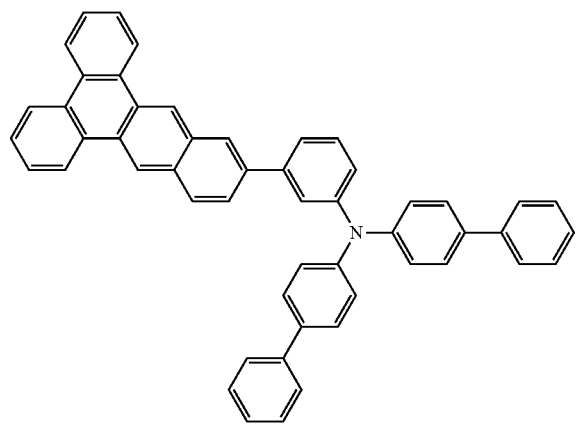
34
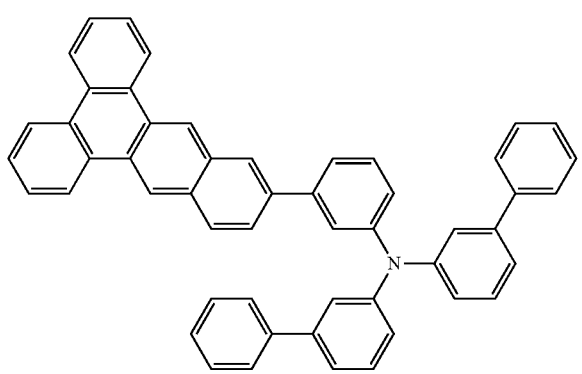
35
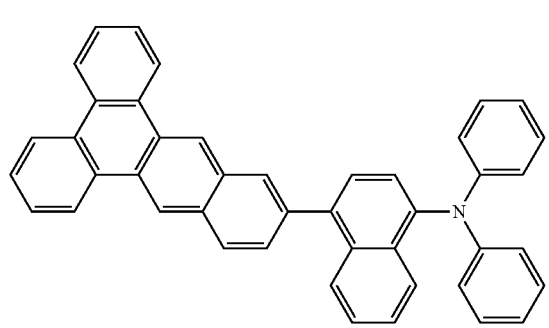
36
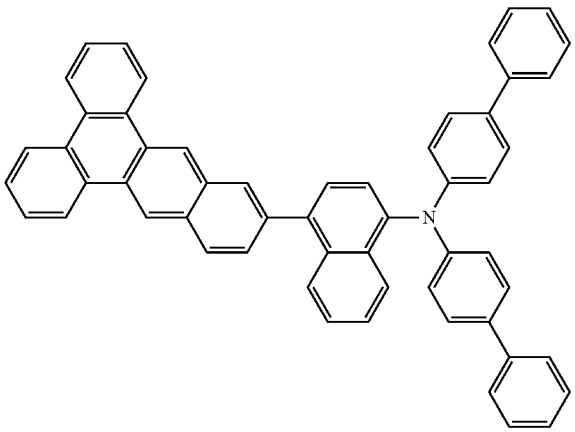
37
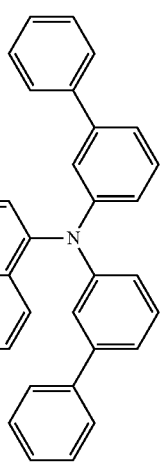
38
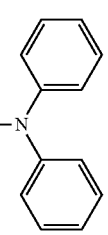

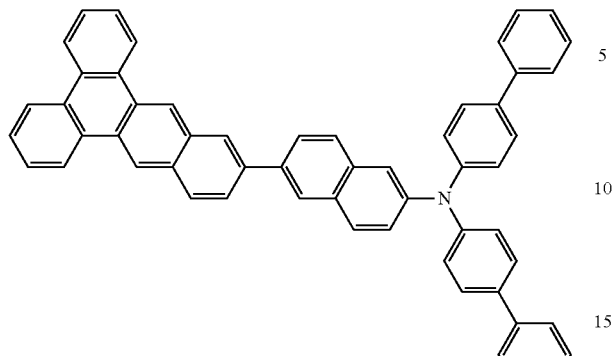
39
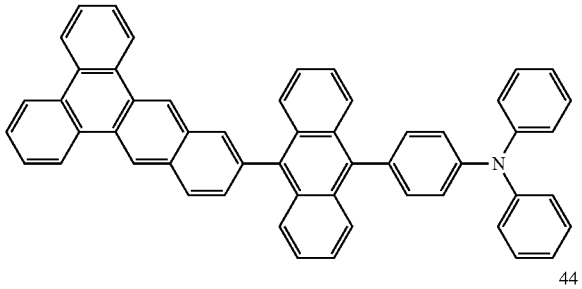
43
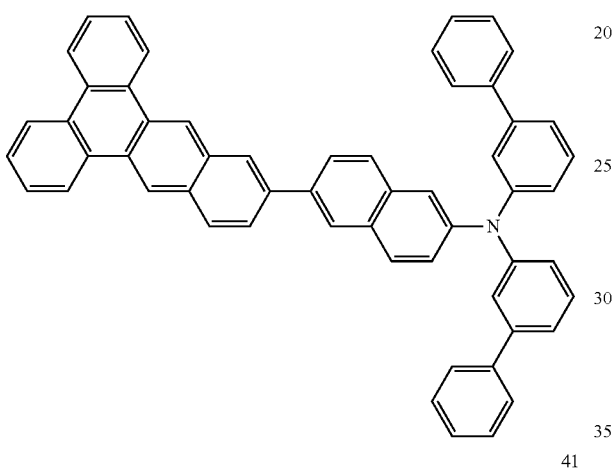
40
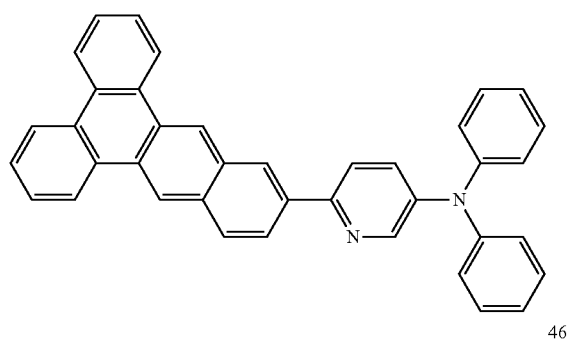
44
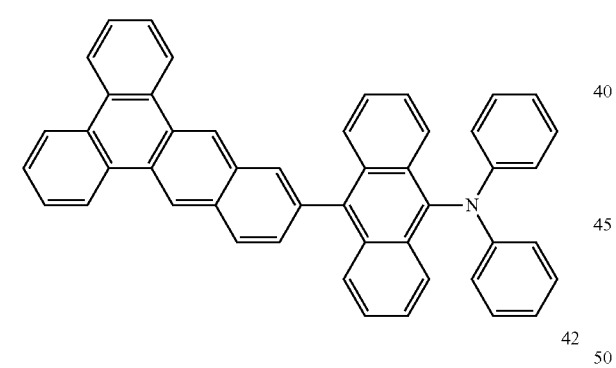
41
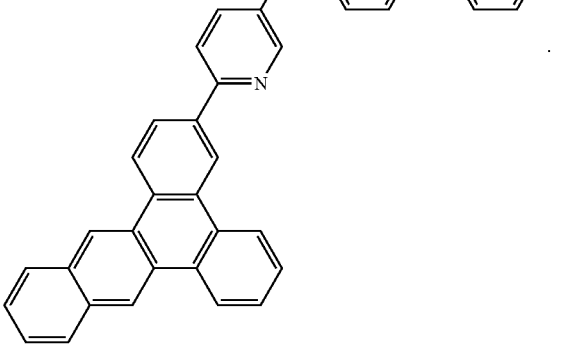
46
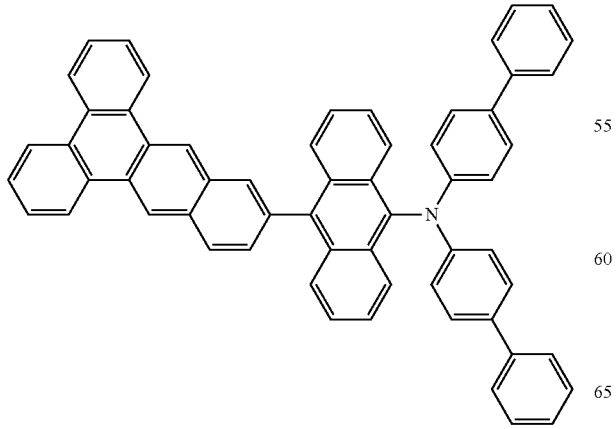
42
47
The embodiments may be realized by providing an organic light-emitting device including a first electrode; a second electrode disposed opposite to the first electrode; and an organic layer between the first electrode and the second electrode, the organic layer including an emission layer, wherein the organic layer includes the compound according to an embodiment.

The first electrode may be an anode, the second electrode may be a cathode, and the organic layer may include a hole transport region between the first electrode and the emission layer, the hole transport region including at least one of a hole injection layer, a hole transport layer, and an electron blocking layer, and an electron transport region between the emission layer and the second electrode, the electron transport region including at least one of a hole blocking layer, an electron transport layer, and an electron injection layer.

The hole transport region may include the compound.

The hole transport region may include the hole transport layer; and the hole transport layer may include the compound.

The hole transport region may further include a charge-generating material.

The charge-generating material may include a p-dopant.

The p-dopant may include one of a quinone derivative, a metal oxide, and a cyano group-containing compound.

The electron transport region may include a metal complex.

The electron transport region may include a Li complex.

The electron transport region may include ET-D1 or ET-D2:

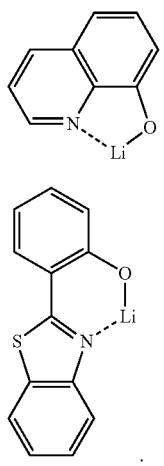

ET-D1

ET-D2

The embodiments may be realized by providing a display device including a thin film transistor, the thin film transistor including a source electrode and a drain electrode; and the organic light-emitting device according to an embodiment, wherein the first electrode of the organic light-emitting device is electrically connected to the source electrode or the drain electrode of the thin film transistor.

BRIEF DESCRIPTION OF THE DRAWING

Features will be apparent to those of skill in the art by describing in detail exemplary embodiments with reference to the attached drawing in which:

The FIGURE illustrates a schematic view of a structure of an organic light-emitting device according to an embodiment.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURES, the dimensions of layers and regions may be exaggerated for clarity of illustration. It will also be understood that when a layer or element is referred to as being "on" another layer or element, it can be directly on the other layer or element, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

According to an aspect of the present disclosure, there is provided a compound represented by Formula 1, below.

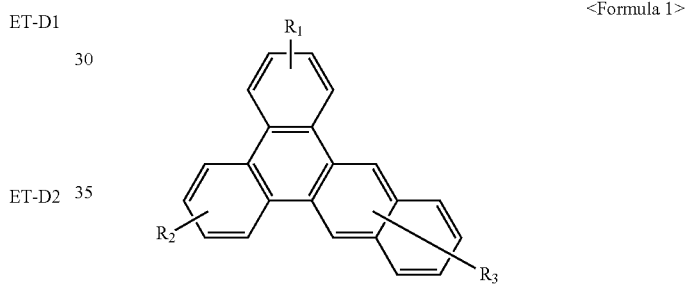

<Formula 1>

In Formula 1, $R_1$ to $R_3$ may each independently be selected from or include, e.g., a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a group represented by Formula 1-1, below, and a substituted or unsubstituted monovalent non-aromatic condensed heteropolycyclic group.

In an implementation, at least one of $R_1$ to $R_3$ may be a group represented by Formula 1-1.

<Formula 1-1>

In Formula 1-1,

X may be selected from or include, e.g., a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group.

m may be an integer of 1 to 3. In an implementation, a plurality of Xs may be the same or different when m is 2 or 3.

$Ar_1$ and $Ar_2$ may each independently be selected from or include, e.g., a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, In an implementation, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$).

$Q_{11}$ to $Q_{17}$ and $Q_{21}$ to $Q_{27}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

A fluorene derivative or an anthracene derivative may be used as a hole transport material. An organic light-emitting device with a hole transport layer including such a hole transport material may not have satisfactory lifetime, efficiency, and power consumption characteristics.

Benzochrysene may be used as a hole transport material. However, using benzochrysene in a hole transport layer may also provide unsatisfactory characteristics.

The embodiments may provide a compound that may have improved electrical stability, improved hole transport ability, and a glass transition temperature that is high enough to help prevent crystallization by inclusion of a compound and that may be suitable for a fluorescent or phosphorescent organic light-emitting device of any color, including red, green, blue, and white. The embodiments may provide an organic light-emitting device with high efficiency, low voltage, high luminance, and long lifespan by inclusion of the compound.

Hereinafter, substituents in Formula 1 will be described in greater detail.

In an implementation, in Formula 1-1, X may be or include, e.g., a substituted or unsubstituted $C_6$-$C_{60}$ arylene group or a substituted or unsubstituted $C_1$-$C_{60}$ heteroarylene group.

In an implementation, in Formula 1-1, X may be a group represented by one of the following Formulae 2a, 2b, and 2c.

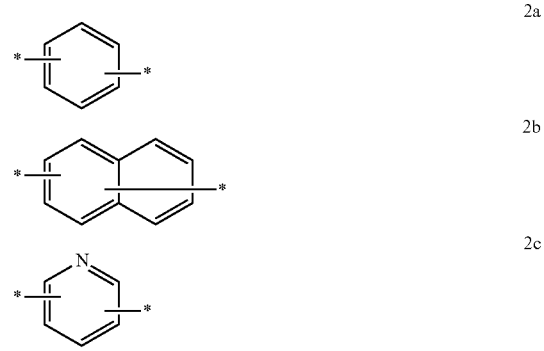

In Formulae 2a, 2b, and 2c, * indicates a binding site to a neighboring atom.

In an implementation, in Formula 1, $Ar_1$ and $Ar_2$ may each independently be or include, e.g., a substituted or unsubstituted $C_6$-$C_{60}$ aryl group or a substituted or unsubstituted $C_1$-$C_{60}$ heteroaryl group.

In an implementation, in Formula 1, An and $Ar_2$ may each independently be a group represented by one of the following Formulae 3a, 3b, and 3c.

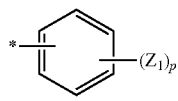

3a

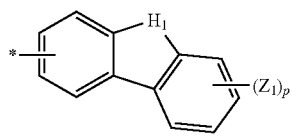

3b

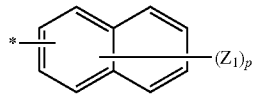

3c

In Formulae 3a, 3b, and 3c, $H_1$ may be, e.g., O or S.

$Z_1$ may be selected from or include, e.g., a hydrogen, a deuterium, a substituted or unsubstituted C1-C20 alkyl group, a substituted or unsubstituted C6-C20 aryl group, a substituted or unsubstituted C1-C20 heteroaryl group, a substituted or unsubstituted monovalent non-aromatic condensed polycyclic group, and a substituted or unsubstituted monovalent non-aromatic condensed heteropolycyclic group.

p may be an integer of, e.g., 1 to 7.

* indicates a binding site to a neighboring atom.

In an implementation, in Formulae 3a, 3b, and 3c, $Z_1$ may be, e.g., one of a hydrogen, a deuterium, and a group represented by the following Formula 4a.

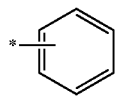

4a

In Formula 4a, * indicates a binding site to a neighboring atom.

In an implementation, the compound represented by Formula 1 may be represented by the following Formula 2.

<Formula 2>

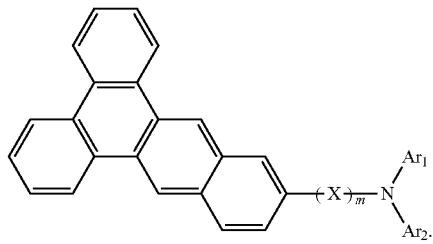

In an implementation, the compound represented by Formula 1 may be represented by the following Formula 3.

<Formula 3>

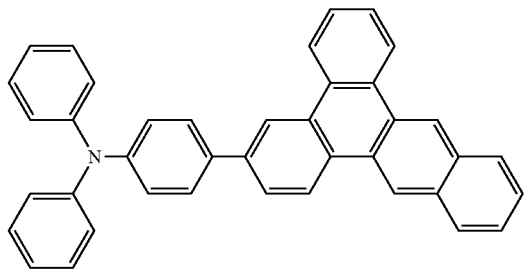

In Formulae 2 and 3, substituents (X, m, $Ar_1$, and $Ar_2$) may be defined the same as those described herein with respect to Formula 1.

In an implementation, the compound represented by Formula 1 may be one of the following Compounds 1 to 44, 46, and 47.

1

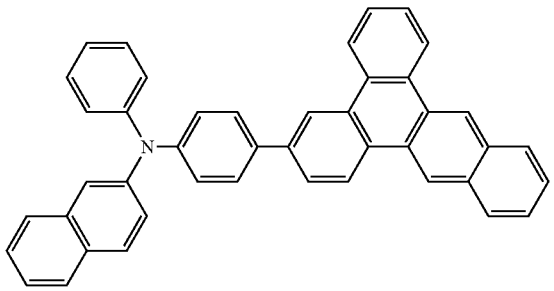

2

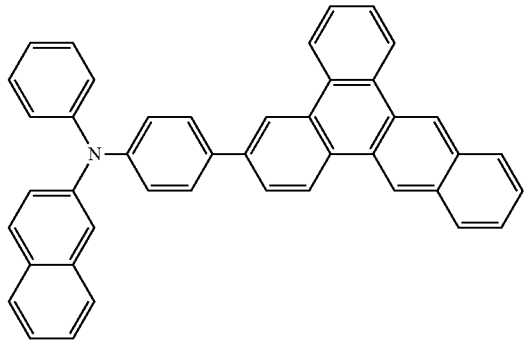

3

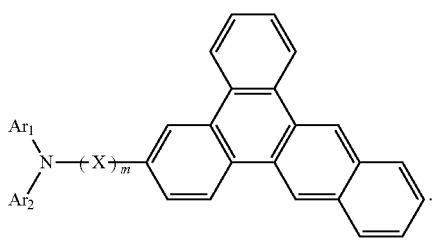

4
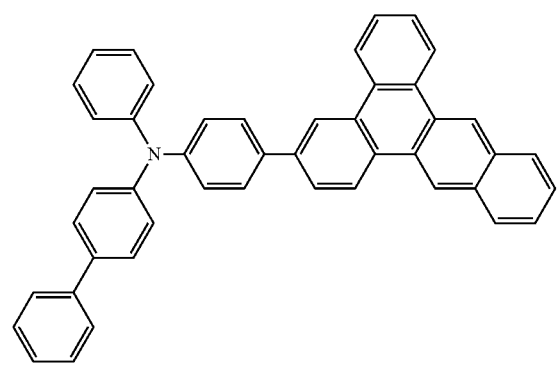
5
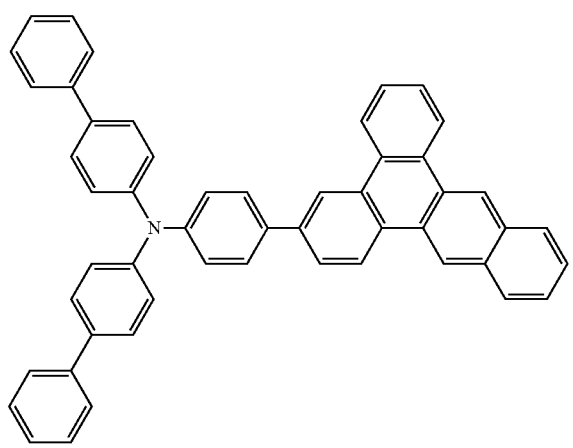
6
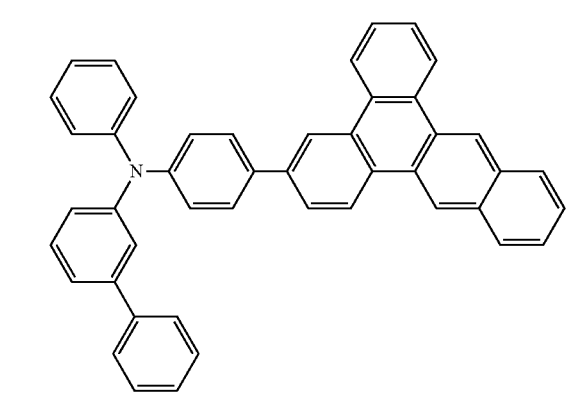
7
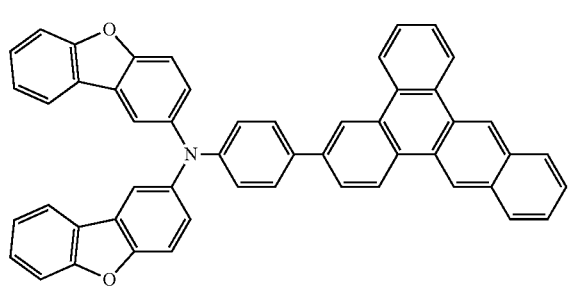
8
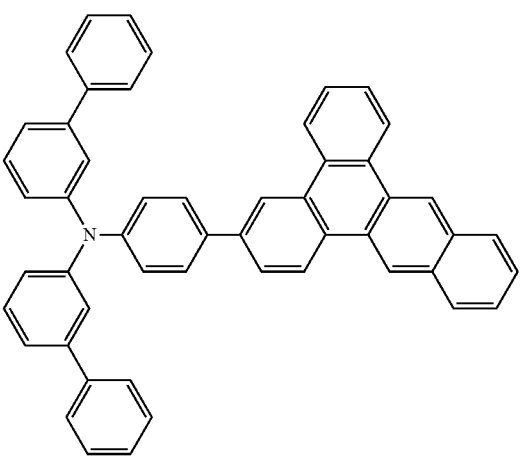
9
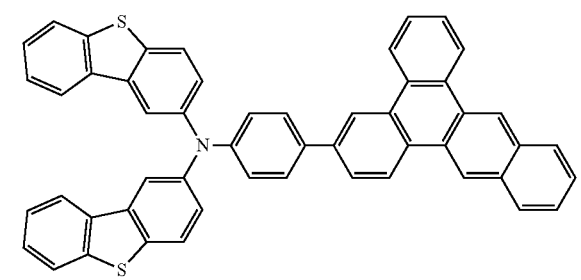
10
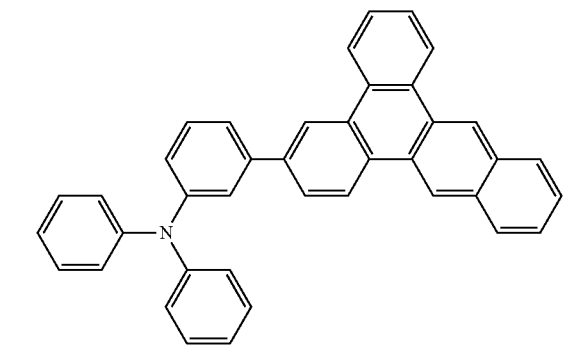
11
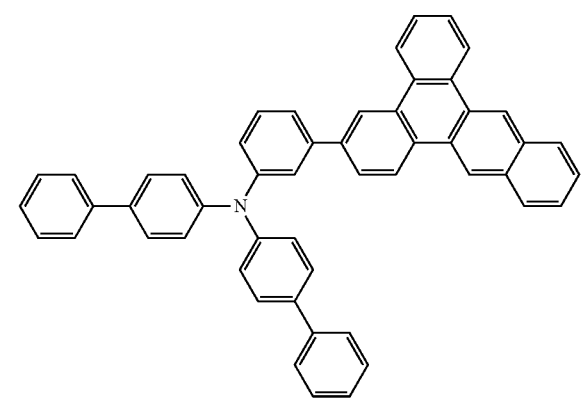

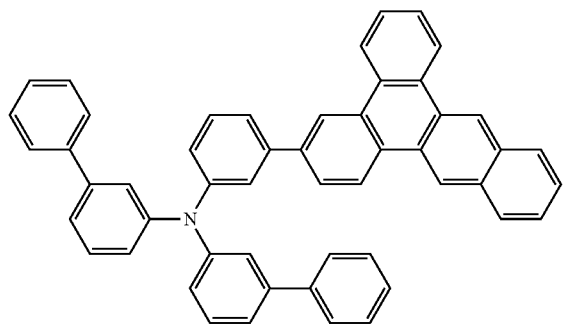
12
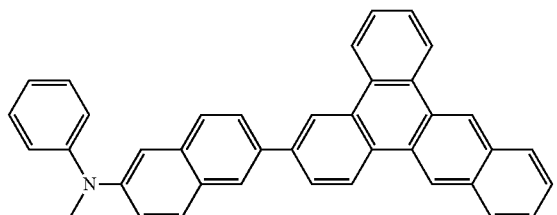
16
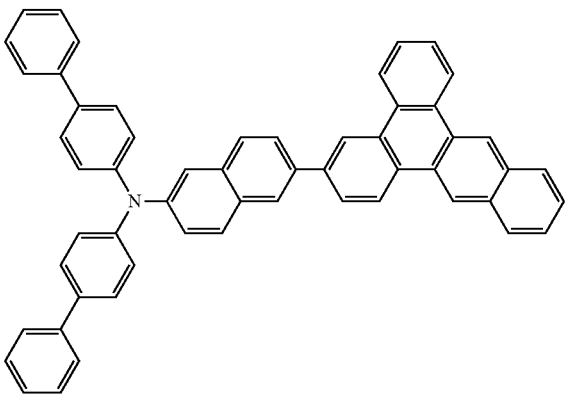
13
17
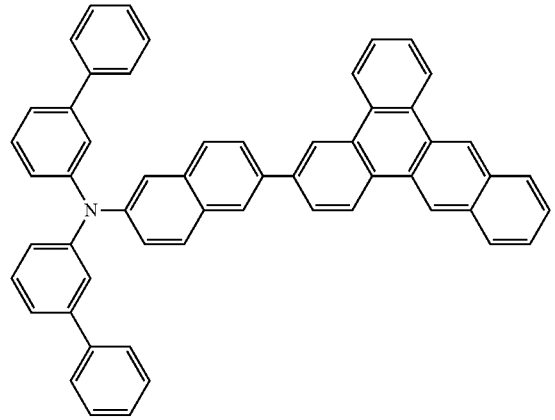
14
18
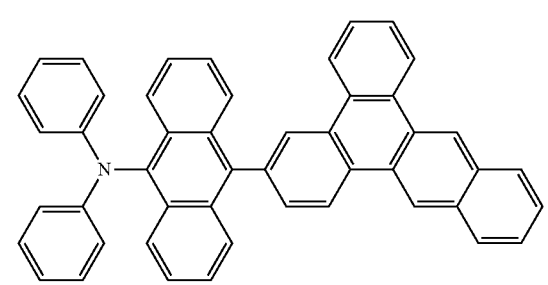
15
19

20
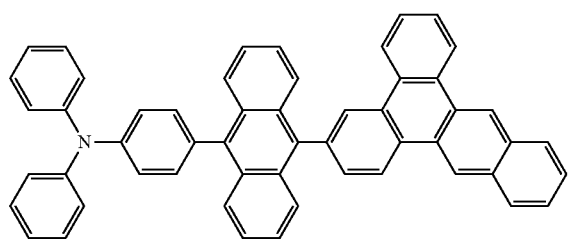
21
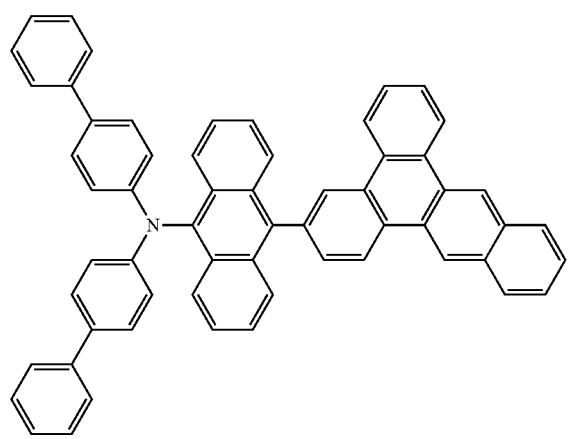
22
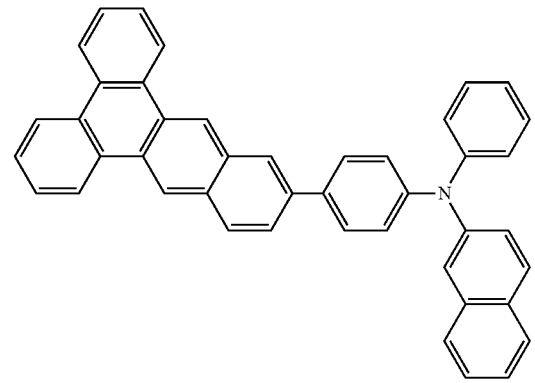
23
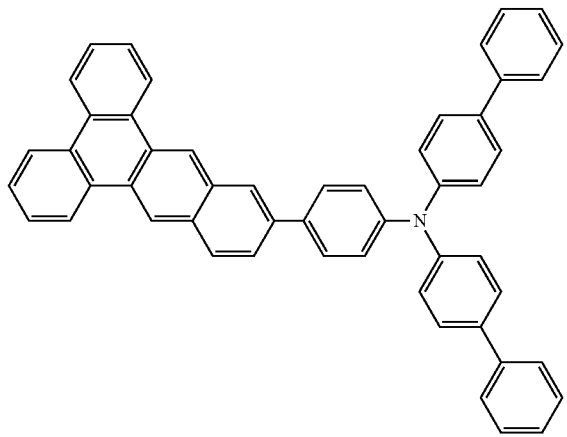
24
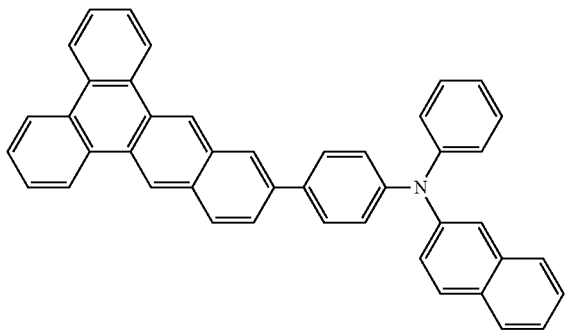
25
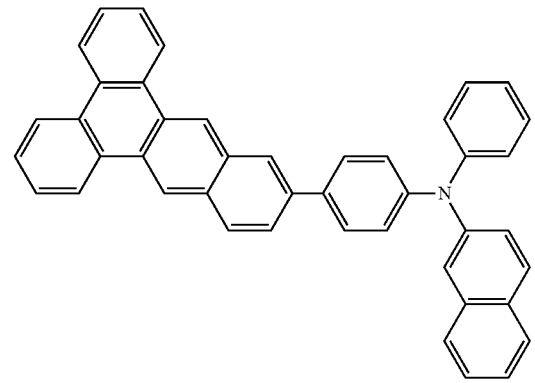
26
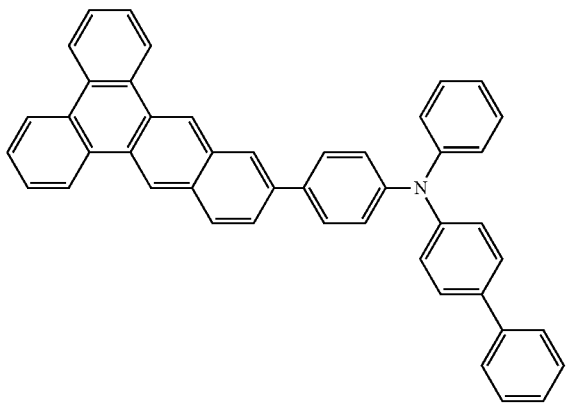
27
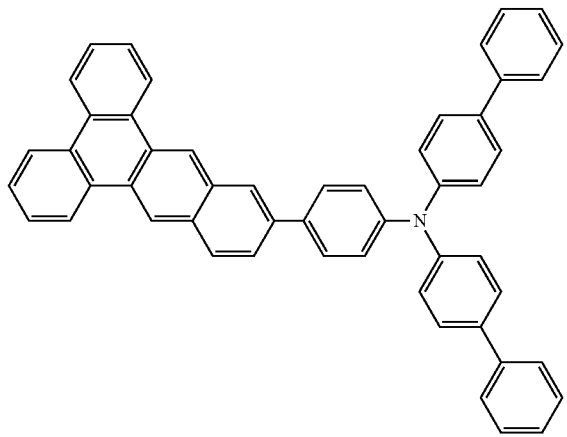

28
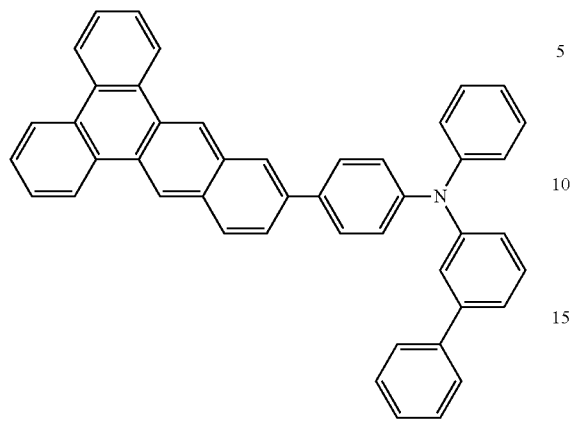
29
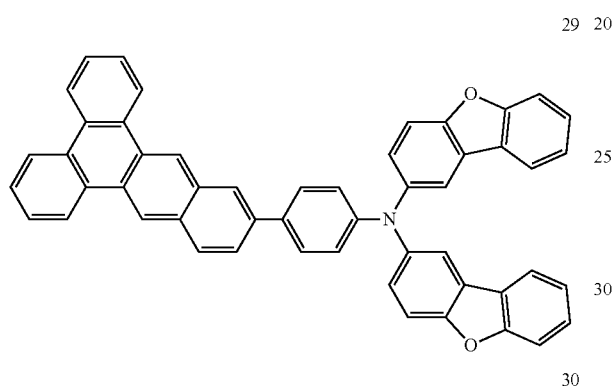
30
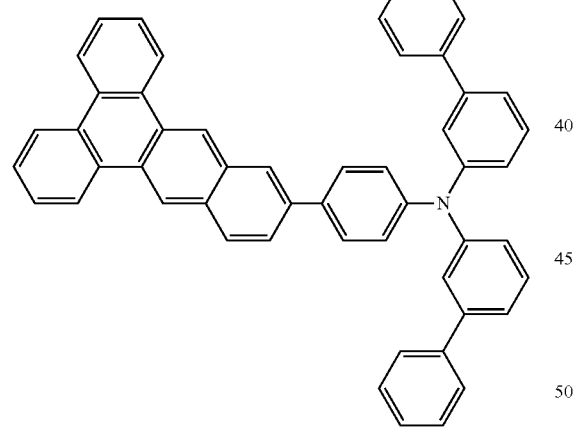
31
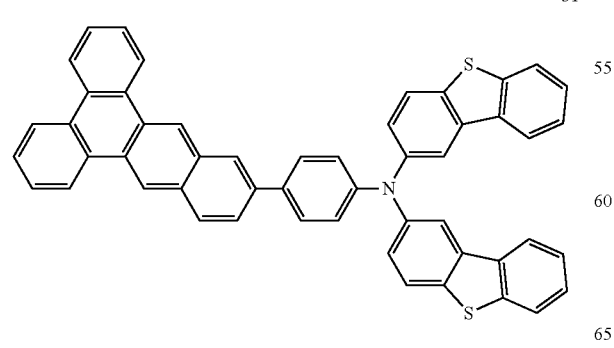
32
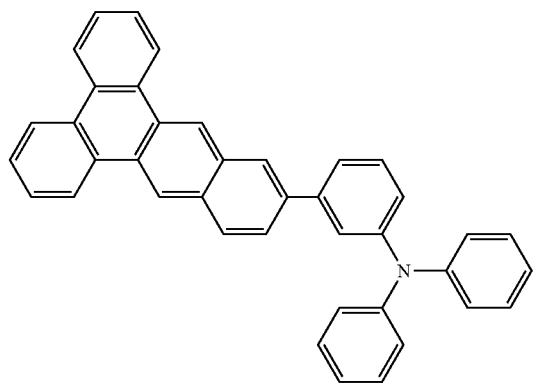
33
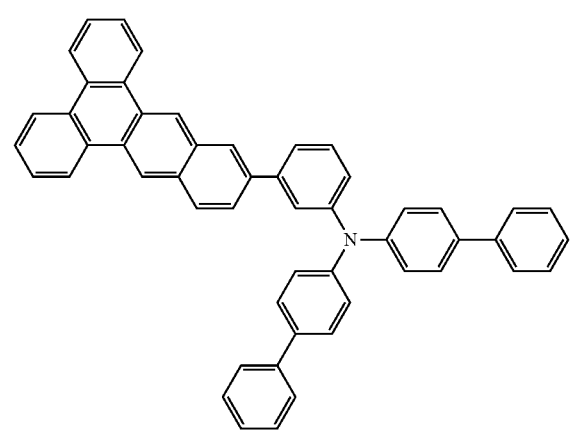
34
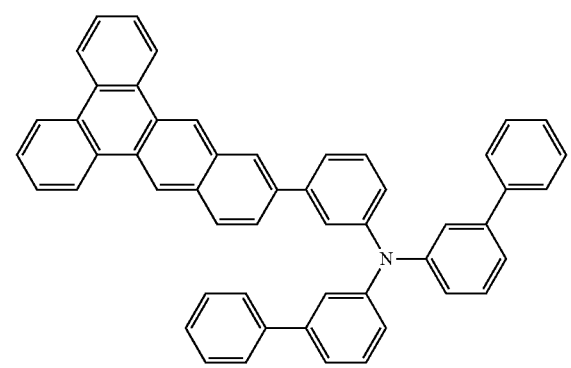
35
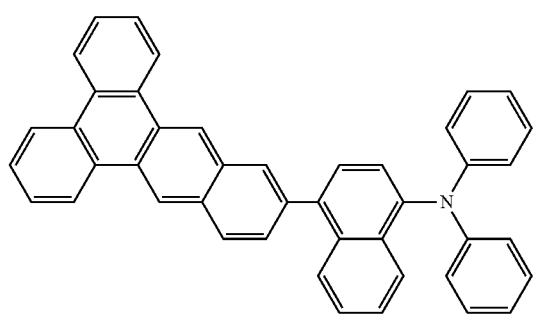

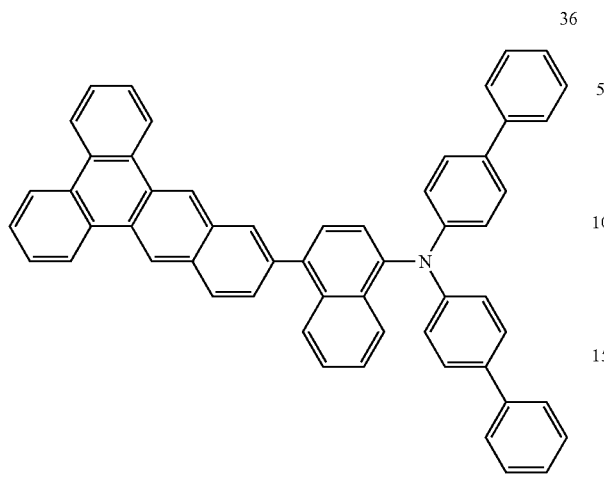
36
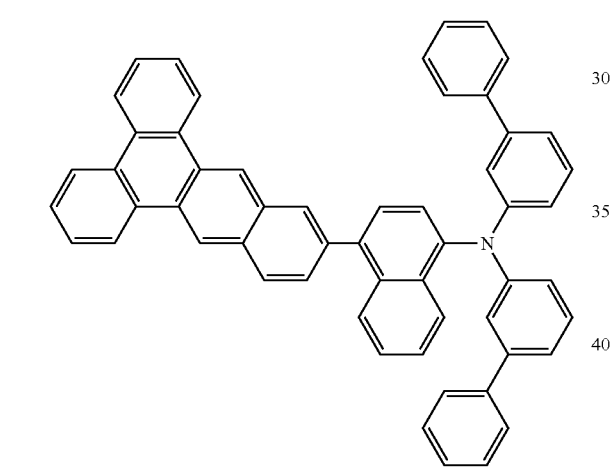
37
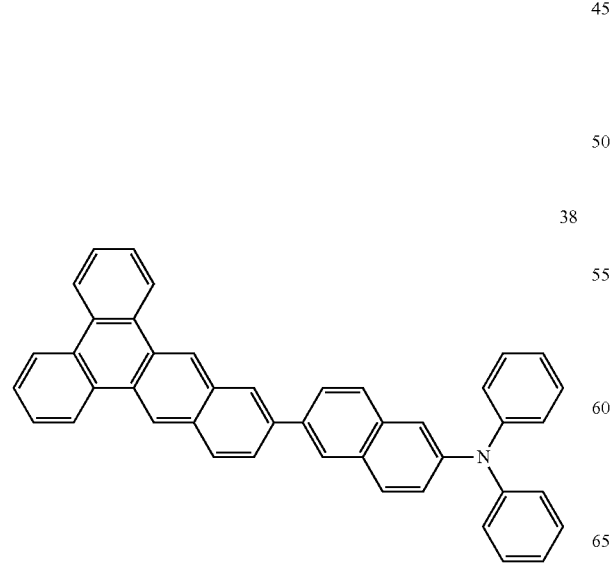
38
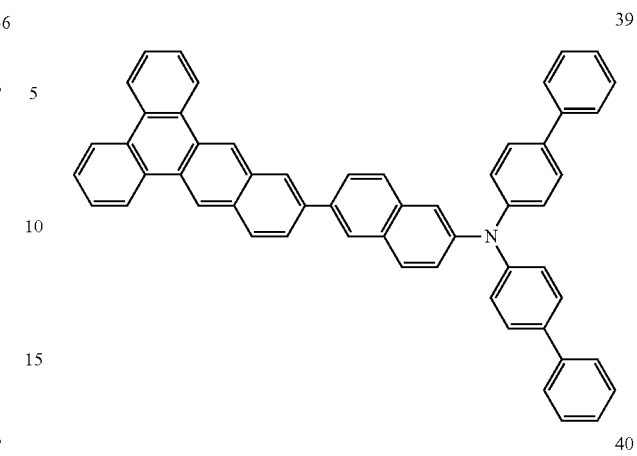

-continued

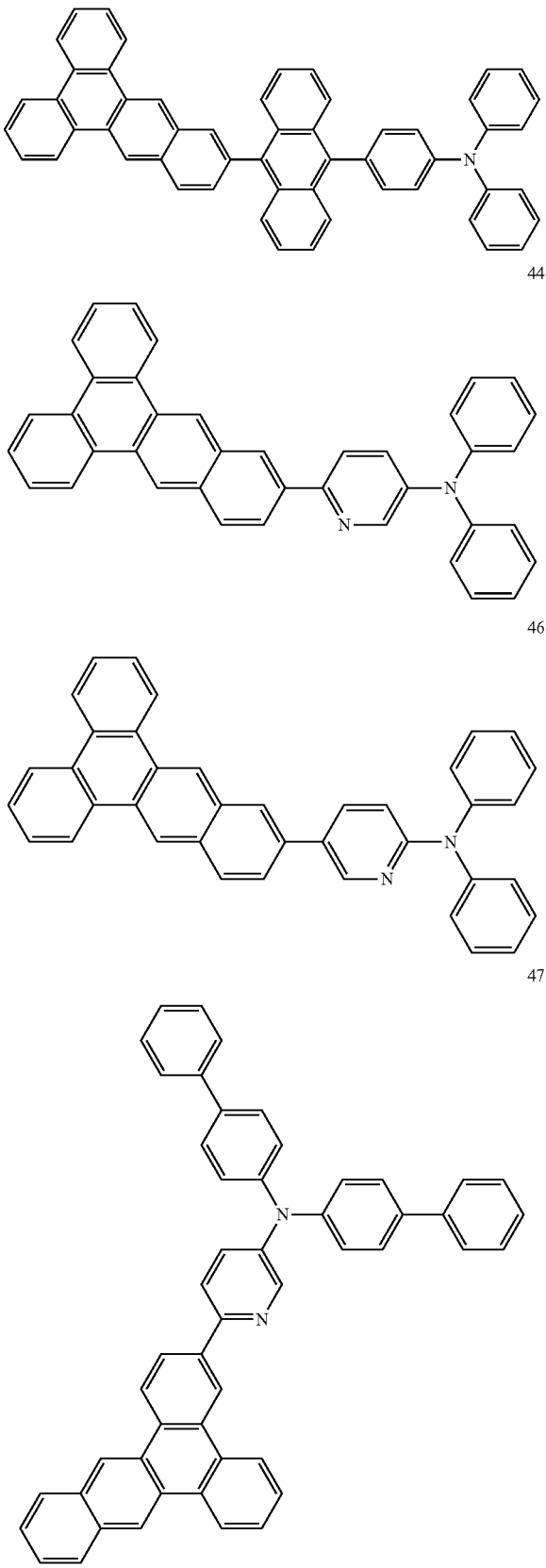

As used herein, the term "organic layer" refers to a single layer and/or a plurality of layers disposed between the first and second electrodes of the organic light-emitting device. Materials included in the "organic layer" are not limited to organic materials.

Hereinafter, a structure of an organic light-emitting device according to an embodiment and a method of manufacturing the same will now be described with reference to the FIGURE.

The FIGURE illustrates a schematic cross-sectional view of an organic light-emitting device 10 according to an embodiment. Referring to the FIGURE, the organic light-emitting device 10 may include a first electrode 110, an organic layer 150, and a second electrode 190.

A substrate may be disposed under the first electrode 110 or on the second electrode 190 in the FIGURE. The substrate may be a glass or transparent plastic substrate with good mechanical strength, thermal stability, transparency, surface smoothness, ease of handling, and water resistance.

For example, the first electrode 110 may be formed by depositing or sputtering a first electrode-forming material on the substrate 11. When the first electrode 110 is an anode, a material having a high work function may be used as the first electrode-forming material to facilitate hole injection. The first electrode 110 may be a reflective electrode, a semi-transmissive electrode, or a transmissive electrode. Transparent and conductive materials such as ITO, IZO, $SnO_2$, and ZnO may be used to form the first electrode. The first electrode 110 as a semi-transmissive electrode or a reflective electrode may be formed of at least one material selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure including a plurality of layers. For example, the first electrode 110 may have a three-layered structure of ITO/Ag/ITO.

The organic layer 150 may be disposed on the first electrode 110. The organic layer 150 may include an emission layer (EML).

The organic layer 150 may further include a hole transport region between the first electrode and the EML, and/or an electron transport region between the EML and the second electrode.

For example, the hole transport region may include at least one of a hole transport layer (HTL), a hole injection layer (HIL), a buffer layer, and an electron blocking layer (EBL). For example, the electron transport layer may include at least one of a hole blocking layer (HBL), an electron transport layer (ETL), and an electron injection layer (EIL).

The hole transport region may have a single-layered structure including a single material, a single-layered structure including a plurality of materials, or a multi-layered structure including a plurality of layers including different materials.

In an implementation, the electron transport region may have a single-layered structure including a plurality of materials, or a multi-layered structure of HIL/HTL, HIL/HTL/buffer layer, HIL/buffer layer, HTL/buffer layer, or HIL/HTL/EBL, wherein these layers forming a multi-layered structure are sequentially disposed on the first electrode 110 in the order stated above.

When the hole transport region includes a HIL, the HIL may be formed on the first electrode 110 by using any of a variety of methods, e.g., by using vacuum deposition, spin coating, casting, Langmuir-Blodgett (LB) deposition, inkjet printing, laser printing, laser induced thermal imaging (LITI), or the like.

When the HIL is formed using vacuum deposition, the deposition conditions may vary depending on the material that is used to form the HIL and the structure of the HIL. For example, the deposition conditions may be selected from the following conditions: a deposition temperature of about 100° C. to about 500° C., a degree of vacuum of about $10^{-8}$ to about $10^{-3}$ torr, and/or a deposition rate of about 0.01 to 100 Å/sec.

When the HIL is formed using spin coating, the coating conditions may vary depending on the material that is used to form the HIL and the structure of the HIL. For example, the coating conditions may be selected from the following conditions: a coating rate of about 2,000 rpm to about 5,000 rpm and a heat treatment temperature of about 80° C. to about 200° C.

When the hole transport region includes a HTL, the HTL may be formed on the first electrode 110 or the HIL by using any of a variety of methods, e.g., by using vacuum deposition, spin coating, casting, Langmuir-Blodgett (LB) deposition, inkjet printing, laser printing, laser induced thermal imaging (LITI), or the like. When the HTL is formed using vacuum deposition or spin coating, the conditions for deposition and coating may be similar to the above-described deposition and coating conditions for forming the HIL, and accordingly will not be described in detail.

In an implementation, the hole transport region may include at least one of m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), and a compound according to an embodiment.

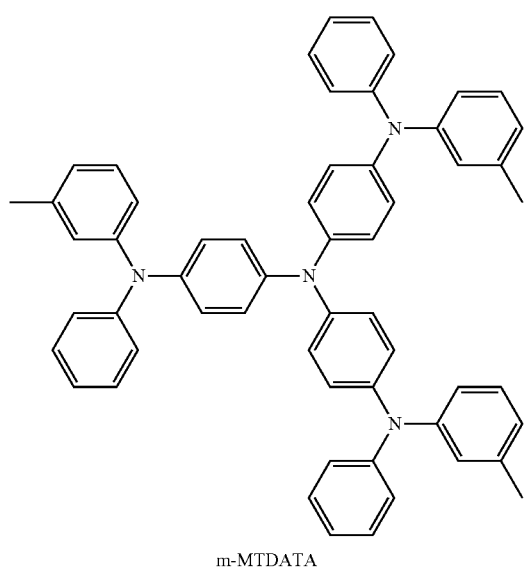

m-MTDATA

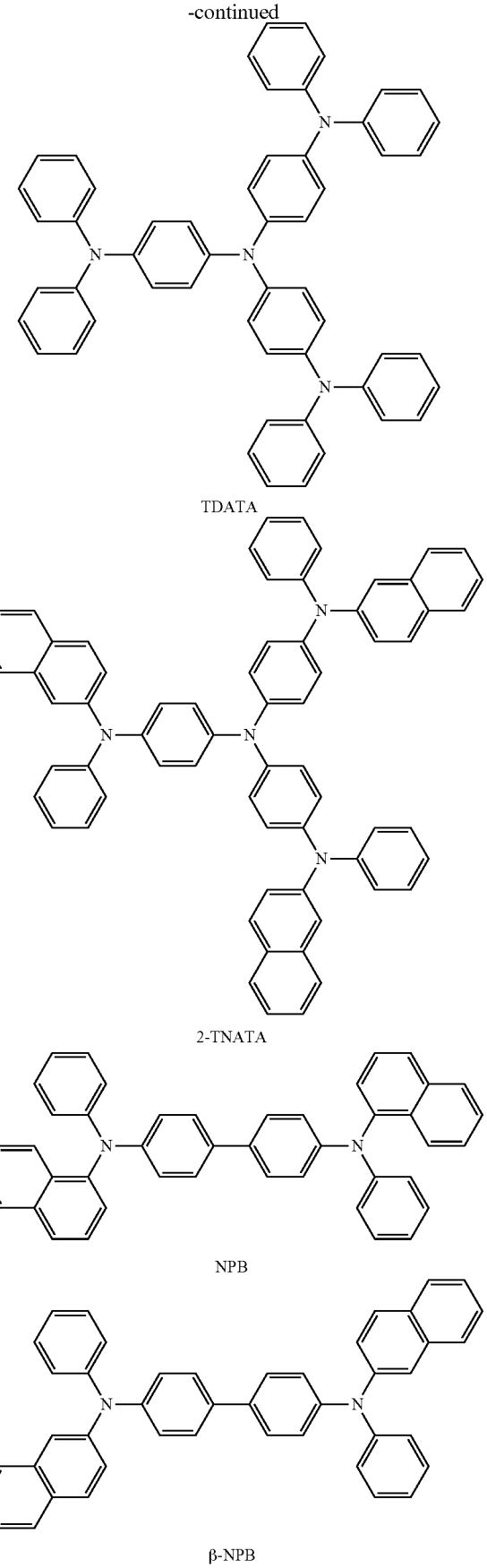

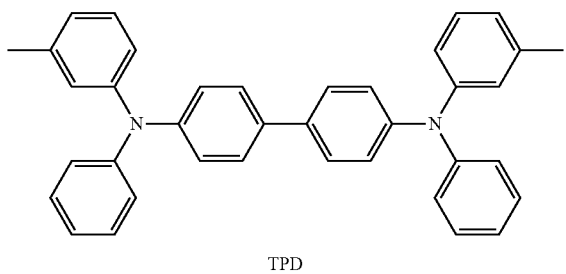

TPD

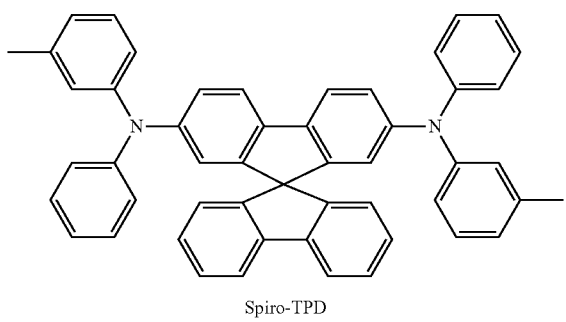

Spiro-TPD

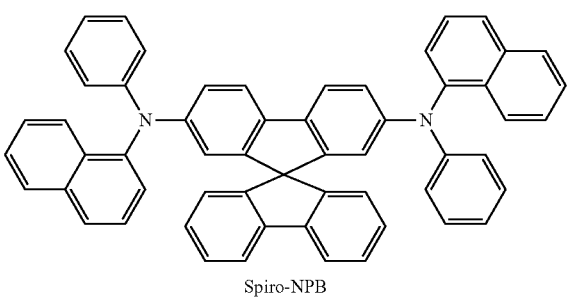

Spiro-NPB

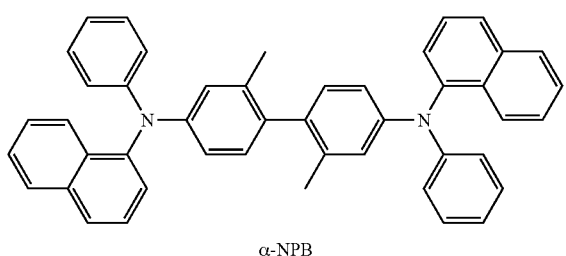

α-NPB

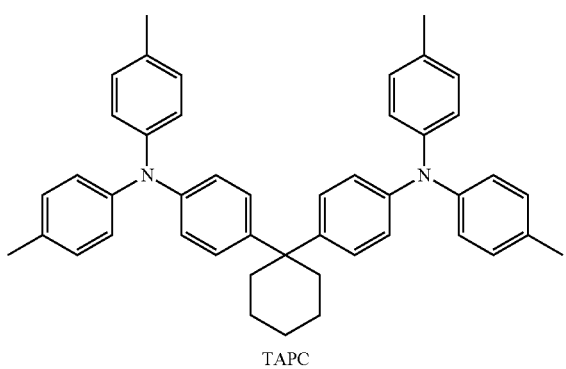

TAPC

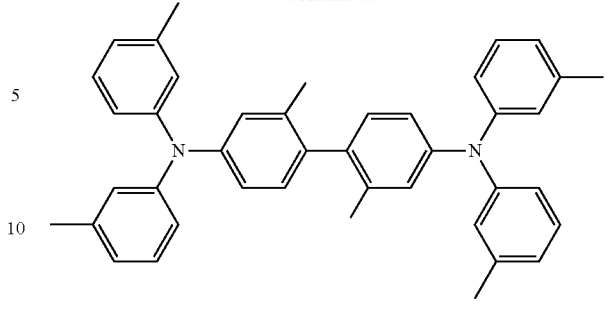

HMTPD

For example, the HTL may include at least one of the compounds according to any of the embodiments.

The thickness of the hole transport region may be from about 100 Å to about 10,000 Å, e.g., from about 100 Å to about 1,000 Å. When the hole transport region includes a HIL and a HTL, a thickness of the HIL may be from about 100 Å to about 10,000 Å, e.g., from about 100 Å to about 1,000 Å, and a thickness of the HTL may be from about 50 Å to about 2,000 Å, e.g., from about 100 Å to about 1,500 Å. When the thicknesses of the hole transport region, the HIL, and the HTL are within these ranges, satisfactory hole transport characteristics may be obtained without a substantial increase in driving voltage.

The hole transport region may further include a charge-generating material to help improve conductivity, in addition to the materials as described above. The charge-generating material may be homogeneously or heterogeneously dispersed in the hole transport region.

The charge-generating material may be, e.g., a p-dopant. The p-dopant may include one of quinone derivatives, metal oxides, and cyano group-containing compounds. Non-limiting examples of the p-dopant may include quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and Compound HT-D1.

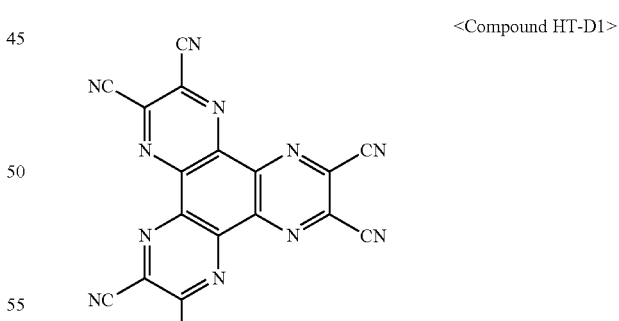

<Compound HT-D1>

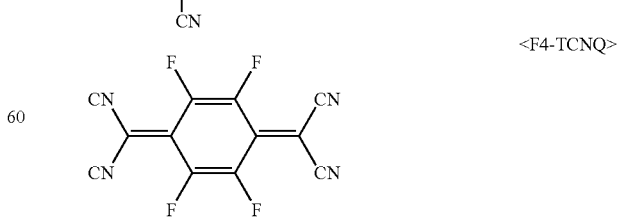

<F4-TCNQ>

The hole transport region may further include a buffer layer, in addition to the EBL, HIL, and HTL described above. The buffer layer may compensate for an optical resonance distance of light according to a wavelength of the light emitted from the EML, and thus may help improve light-emission efficiency. A material in the buffer layer may include any suitable material used in the hole transport region. The EBL may block migration of electrons from the electron transport region into EML.

The EML may be formed on the first electrode 110 or the hole transport region by using any of a variety of methods, e.g., by using vacuum deposition, spin coating, casting, Langmuir-Blodgett (LB) deposition, inkjet printing, laser printing, laser induced thermal imaging (LITI), or the like. When the EML is formed using vacuum deposition or spin coating, the deposition and coating conditions for forming the EML may be similar to the above-described deposition and coating conditions for forming the HIL, and accordingly will not be described in detail When the organic light-emitting device 10 is a full color organic light-emitting device, the EML may be patterned into a red emission layer, a green emission layer, and a blue emission layer to correspond to individual subpixels, respectively. In an implementation, the EML may have a structure in which a red emission layer, a green emission layer and a blue emission layer are stacked upon one another, or a structure including a mixture of a red light-emitting material, a green light-emitting material, and a blue light-emitting material without separation of layers for the different color emission, and thus may emit white light.

The EML may include a host and a dopant.

The host may include, e.g., at least one of TPBi, TBADN, ADN (also referred to as "DNA"), CBP, CDBP, and TCP.

TPBi

TBADN

ADN

CBP

CDBP

TCP

In an implementation, the host may include a compound represented by Formula 301.

$$Ar_{301}\text{-}[(L_{301})_{xb1}\text{-}R_{301}]_{xb2} \qquad <\text{Formula 301}>$$

In Formula 301, $Ar_{301}$ may be selected from a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (where $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{301}$ may be selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

$R_{301}$ may be selected from a $C_1$-$C_{20}$ alkyl group, and a $C_1$-$C_{20}$ alkoxy group, a $C_1$-$C_{20}$ alkyl group, and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3; and xb2 may be selected from 1, 2, 3, and 4.

For example, in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and $R_{301}$ may be selected from a $C_1$-$C_{20}$ alkyl group, and a $C_1$-$C_{20}$ alkoxy group, a $C_1$-$C_{20}$ alkyl group, and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

In some other embodiments, the host may include a compound represented by Formula 301A.

<Formula 301A>

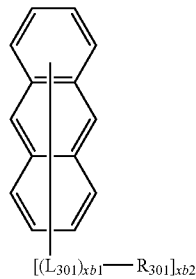

$[(L_{301})_{xb1}\text{---}R_{301}]_{xb2}$

In Formula 301A, substituents may be defined the same as those described herein.

The compound of Formula 301 may include at least one of Compounds H1 to H42.

H1
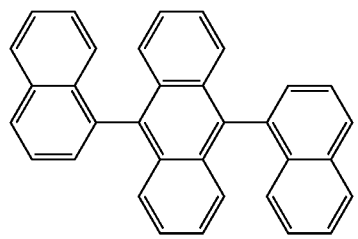

H2
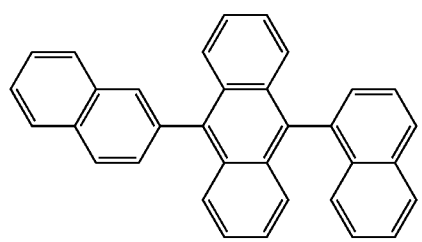

H3
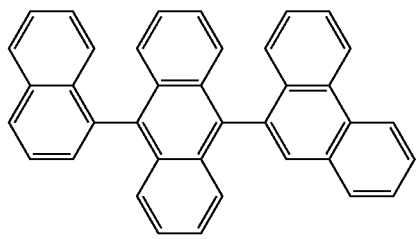

H4
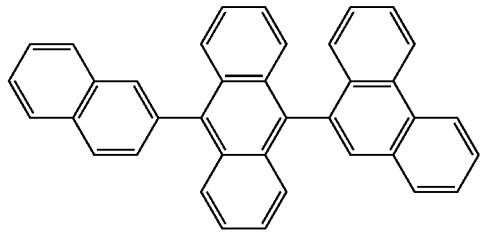

H5
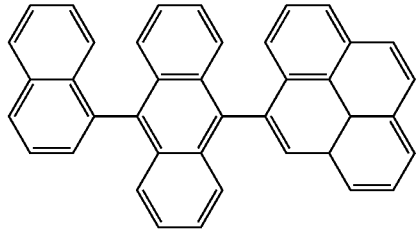

H6
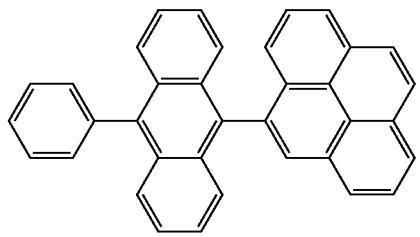

H7
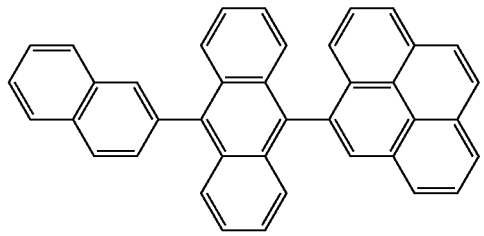

H8
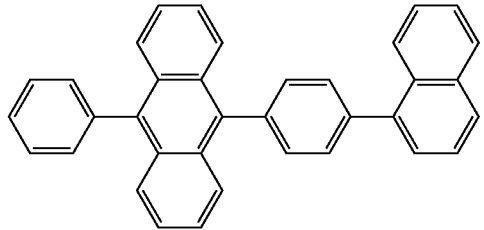

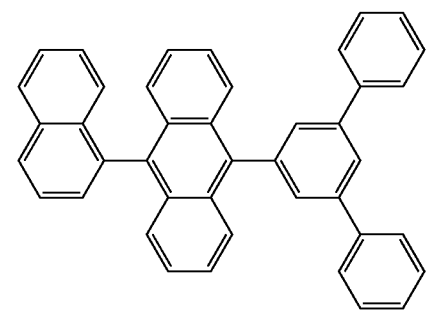
H9
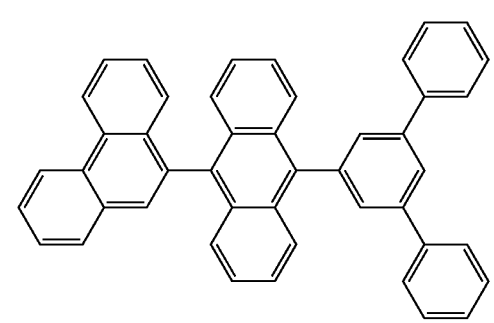
H10
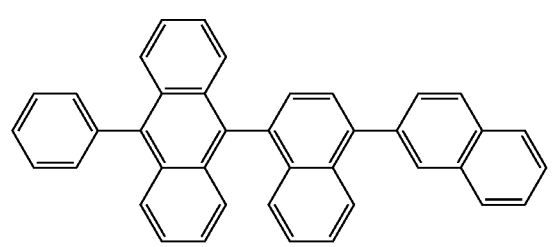
H11
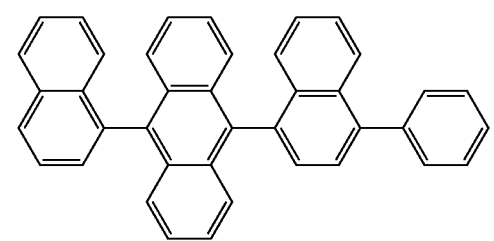
H12
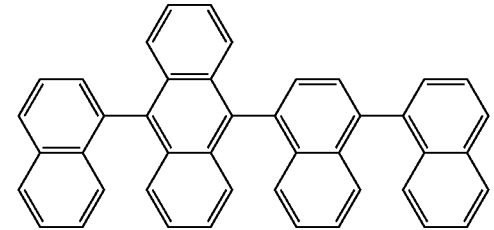
H13
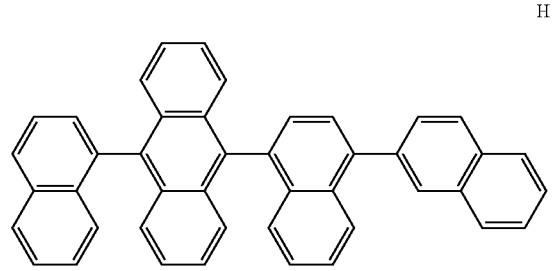
H14
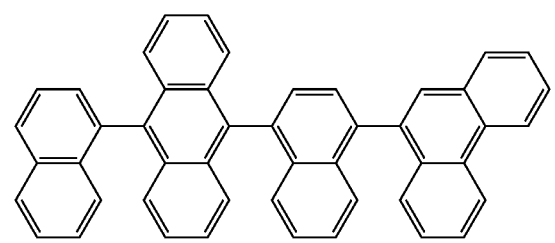
H15
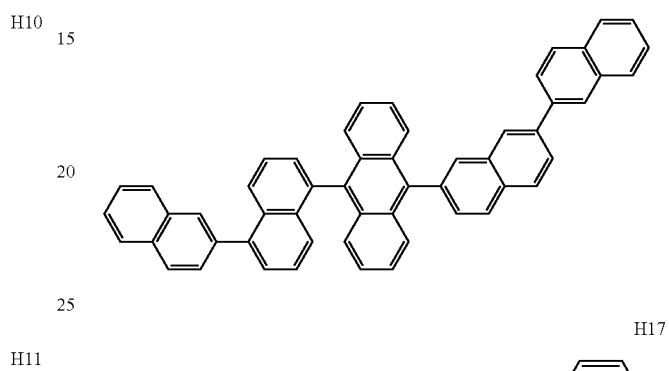
H16
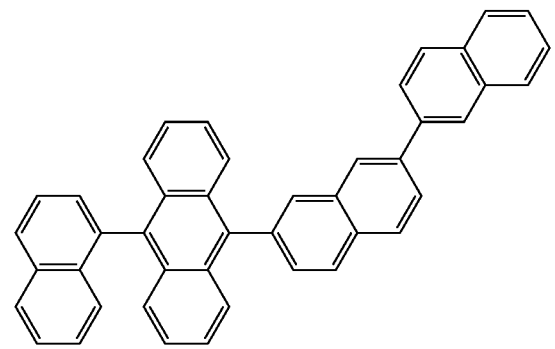
H17
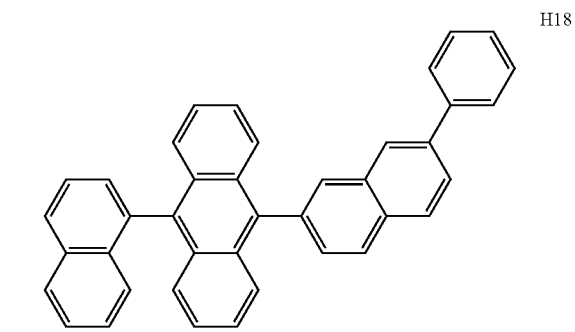
H18
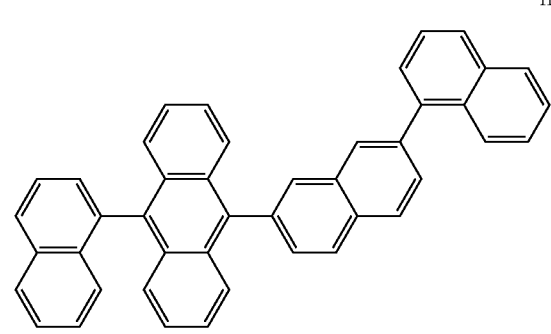
H19

-continued
H20
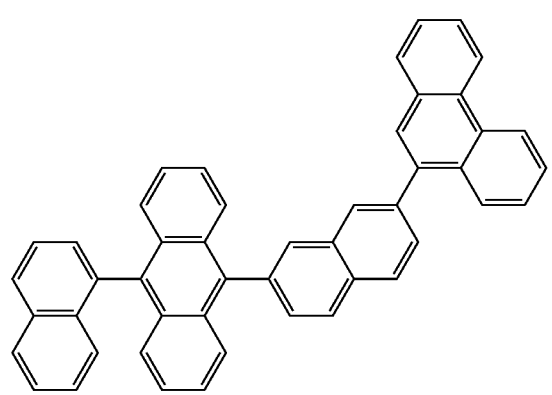
H21
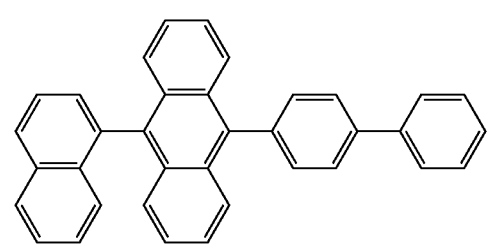
H22
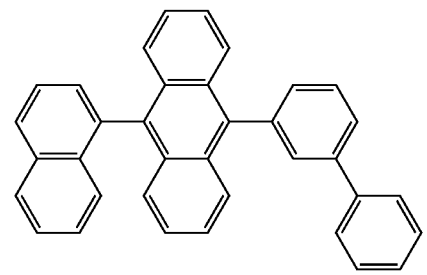
H23
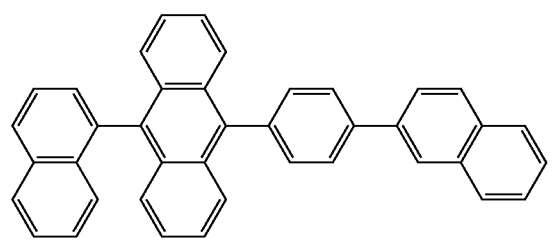
H24
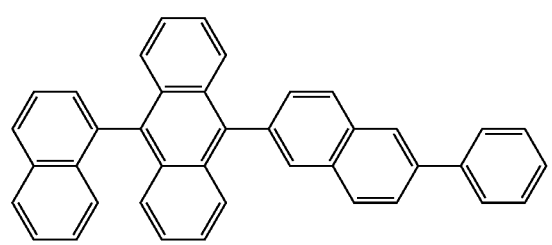
-continued
H25
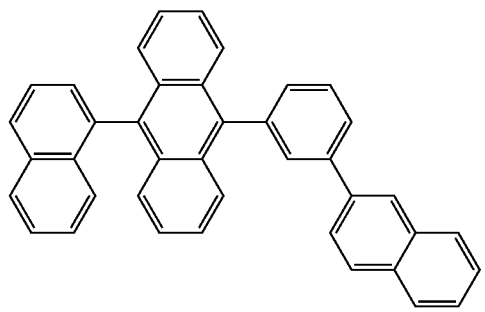
H26
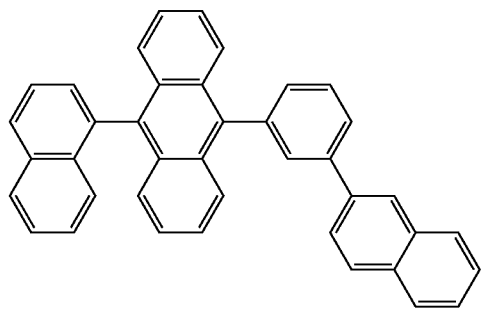
H27
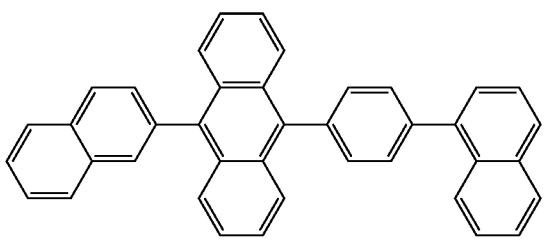
H28
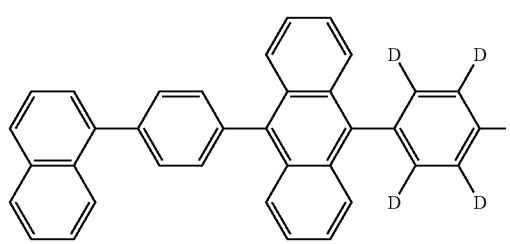
H29
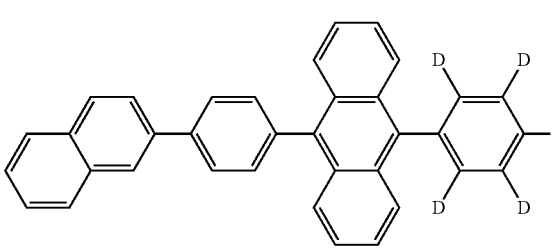
H30
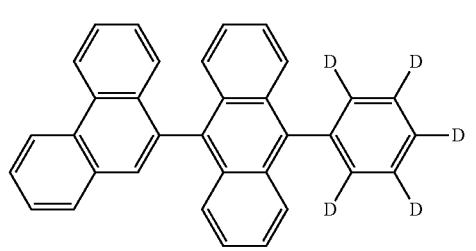

H31
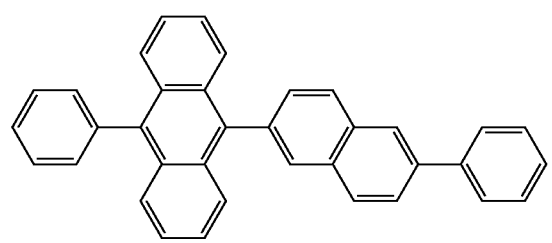
H32
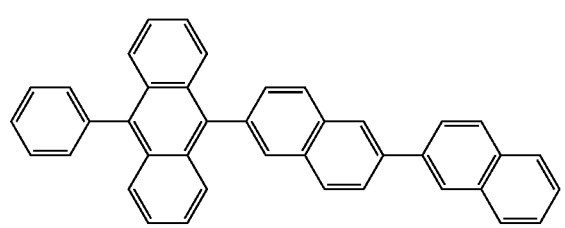
H33
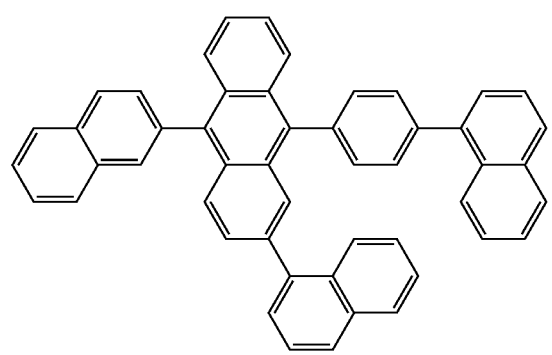
H34
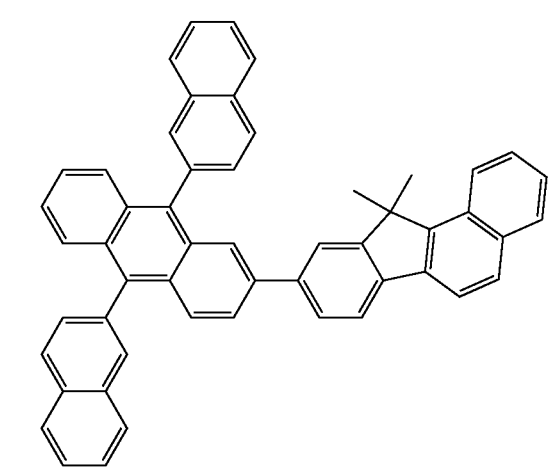
H35
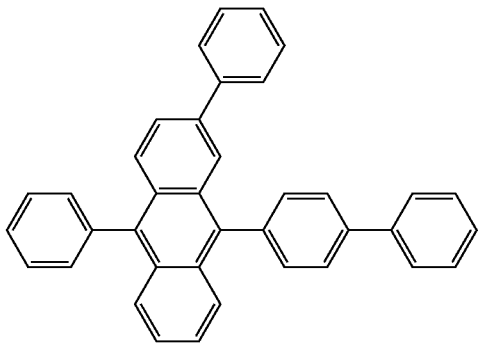
H36
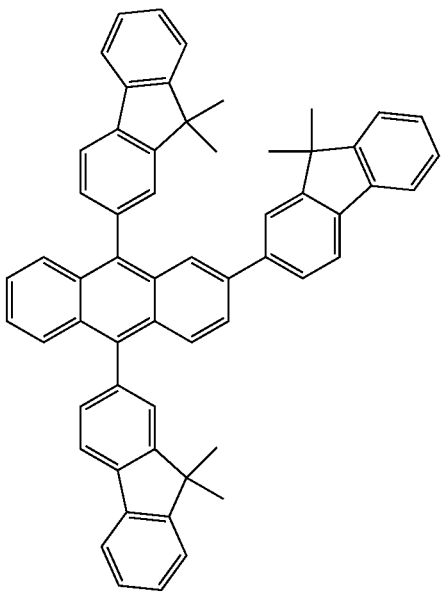
H37
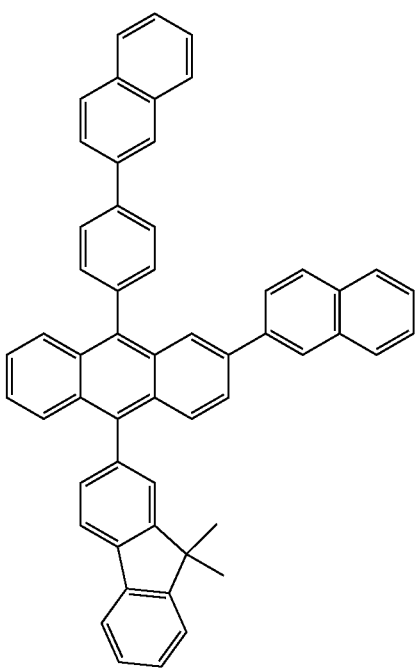

H38
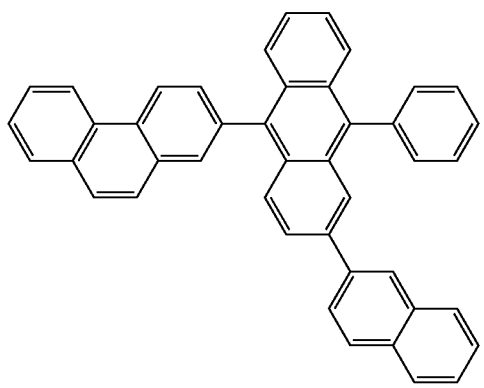
H39
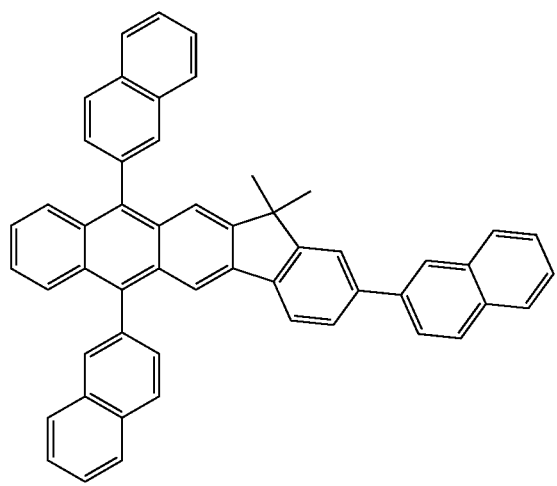
H40
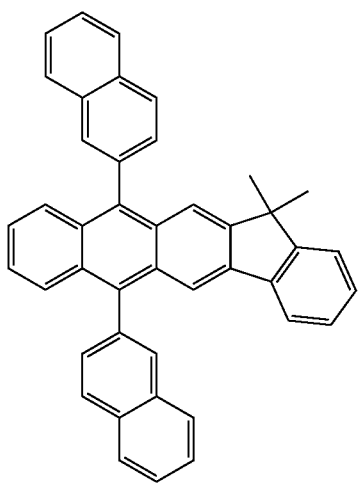
H41
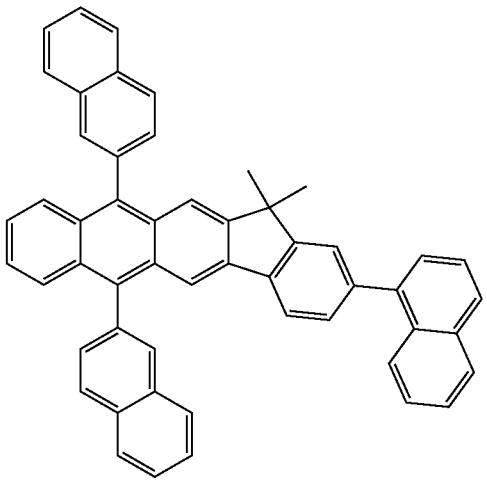
H42
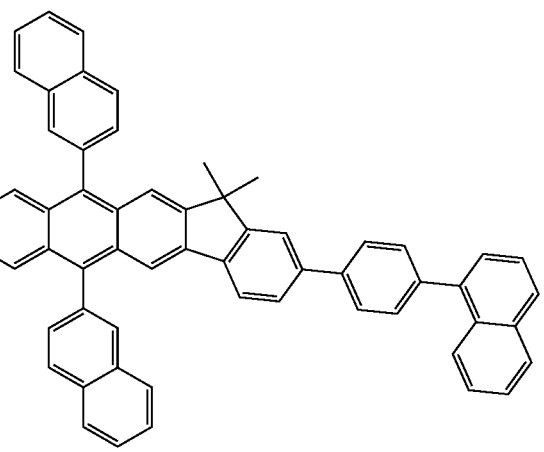
In an implementation, the host may include at least one of Compounds H43 to H49.
H43
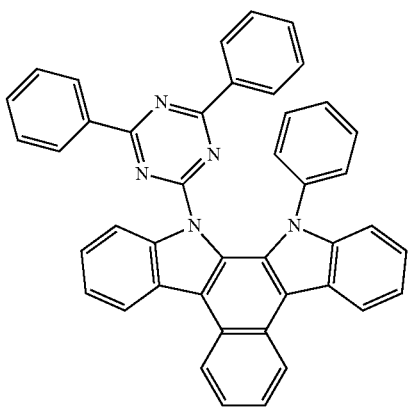

H44
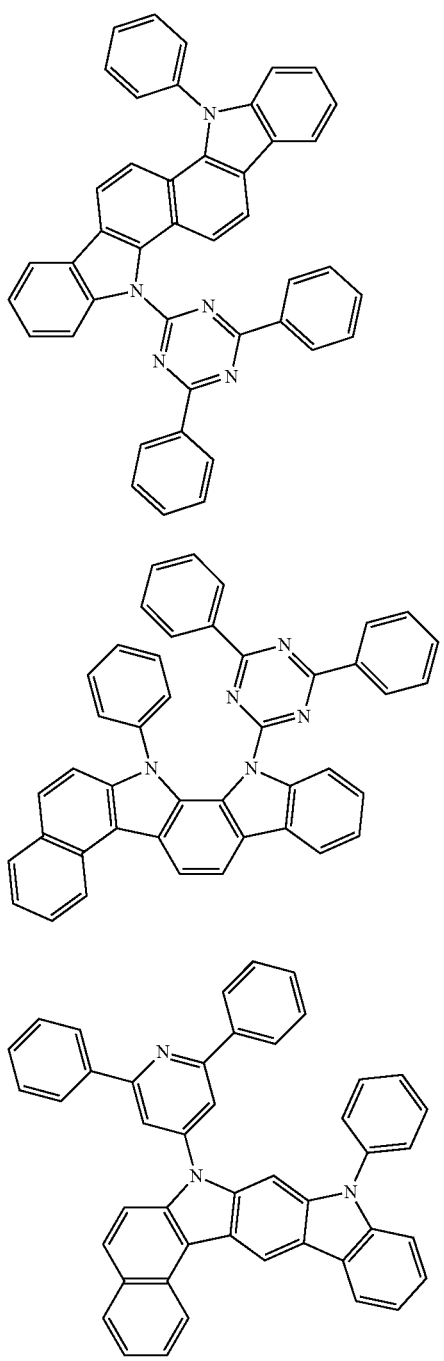
H45
H46
H47
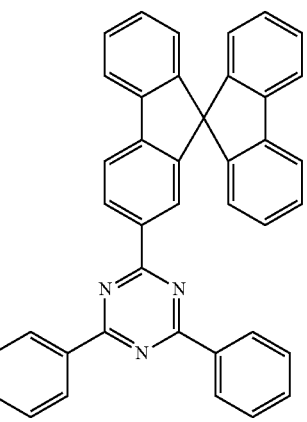
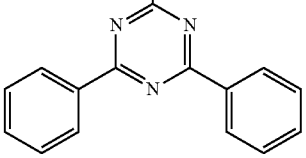
H48
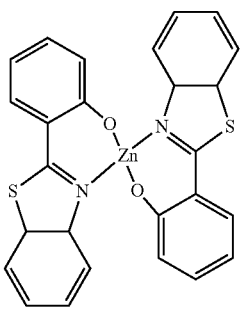
H49
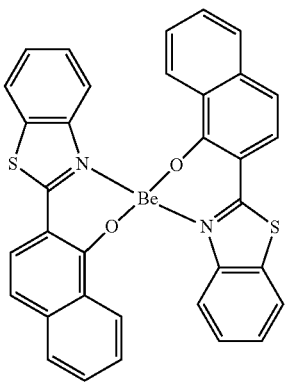
The dopant for the EML may include at least one of a fluorescent dopant and a phosphorescent dopant.
The phosphorescent dopant may include an organic metal complex represented by Formula 401.
<Formula 401>
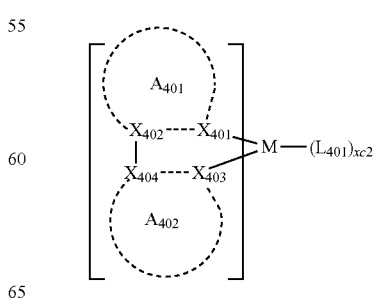
In Formula 401, M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may be each independently a nitrogen or a carbon, $A_{401}$ and $A_{402}$ ring may be each independently selected from a substituted or unsubstituted benzene group, a substituted or unsubstituted naphthalene group, a substituted or unsubstituted fluorene group, a substituted or unsubstituted spiro-fluorene group, a substituted or unsubstituted indene group, a substituted or unsubstituted pyrrole group, a substituted or unsubstituted thiophene group, a substituted or unsubstituted furan group, a substituted or unsubstituted imidazole group, a substituted or unsubstituted pyrazole group, a substituted or unsubstituted thiazole group, a substituted or unsubstituted isothiazole group, a substituted or unsubstituted oxazole group, a substituted or unsubstituted isooxazole group, a substituted or unsubstituted pyridine group, a substituted or unsubstituted pyrazine group, a substituted or unsubstituted pyrimidine group, a substituted or unsubstituted pyridazine group, a substituted or unsubstituted quinoline group, a substituted or unsubstituted isoquinoline group, a substituted or unsubstituted benzoquinoline group, a substituted or unsubstituted quinoxaline group, a substituted or unsubstituted quinazoline group, a substituted or unsubstituted carbazole group, a substituted or unsubstituted benzoimidazole group, a substituted or unsubstituted benzofuran group, a substituted or unsubstituted benzothiophene group, a substituted or unsubstituted isobenzothiophene group, a substituted or unsubstituted benzoxazole group, a substituted or unsubstituted isobenzoxazole group, a substituted or unsubstituted triazole group, a substituted or unsubstituted oxadiazole group, a substituted or unsubstituted triazine group, a substituted or unsubstituted dibenzofuran group, and a substituted or unsubstituted dibenzothiophene group, at least one substituent of the substituted benzene group, the substituted naphthalene group, the substituted fluorene group, the substituted spiro-fluorene group, the substituted indene group, the substituted pyrrole group, the substituted thiophene group, the substituted furan group, the substituted imidazole group, the substituted pyrazole group, the substituted thiazole group, the substituted isothiazole group, the substituted oxazole group, the substituted isooxazole group, the substituted pyridine group, the substituted pyrazine group, the substituted pyrimidine group, the substituted pyridazine group, the substituted quinoline group, the substituted isoquinoline group, the substituted benzoquinoline group, the substituted quinoxaline group, the substituted quinazoline group, the substituted carbazole group, the substituted benzoimidazole group, the substituted benzofuran group, the substituted benzothiophene group, the substituted isobenzothiophene group, the substituted benzoxazole group, the substituted isobenzoxazole group, the substituted triazole group, the substituted oxadiazole group, the substituted triazine group, the substituted dibenzofuran group, and the substituted dibenzothiophene group may be selected from a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$), and —N($Q_{421}$)($Q_{422}$), —Si($Q_{423}$)($Q_{424}$)($Q_{425}$), and —B($Q_{426}$)($Q_{427}$);

$L_{401}$ may be an organic ligand;

xc1 may be 1, 2, or 3; and xc2 may be 0, 1, 2, or 3.

For example, $L_{401}$ may be a monovalent, divalent, or trivalent organic ligand. For example, $L_{401}$ may be selected from a halogen ligand (for example, Cl or F), a diketone ligand (for example, acetylacetonate, 1,3-diphenyl-1,3-propanedionate, 2,2,6,6-tetramethyl-3,5-heptanedionate, or hexafluoroacetonate), a carboxylic acid ligand (for example, picolinate, dimethyl-3-pyrazole carboxylate, or benzoate), a carbon monoxide ligand, an isonitrile ligand, a cyano ligand, and a phosphorous ligand (for example, phosphine or phosphite).

When $A_{401}$ in Formula 401 has at least two substituents, the at least two substituents of $A_{401}$ may be linked to each other to form a saturated or unsaturated ring.

When $A_{402}$ in Formula 401 has at least two substituents, the at least two substituents of $A_{402}$ may be linked to each other to form a saturated or unsaturated ring.

When xc1 in Formula 401 is 2 or greater, the plurality of ligands in Formula 401, represented by

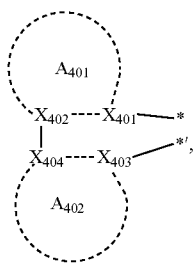
may be identical or differ. When xc1 in Formula 401 is 2 or greater, $A_{401}$ and $A_{402}$ may be linked to $A_{401}$ and $A_{402}$ of another adjacent ligand directly or via a linker (for example, a $C_1$-$C_5$ alkylene group, —N(R')— (where R' is a $C_1$-$C_{10}$ alkyl group or a $C_6$-$C_{20}$ aryl group), or —C(═O)—).
The fluorescent dopant may include at least one of Compounds PD1 to PD74.
PD1
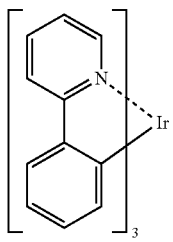
PD2
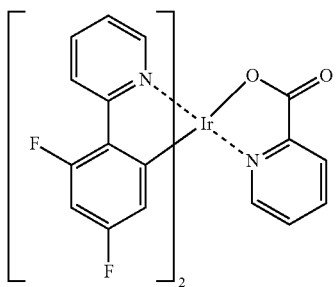
PD3
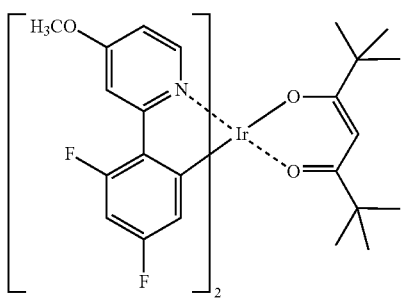
PD4
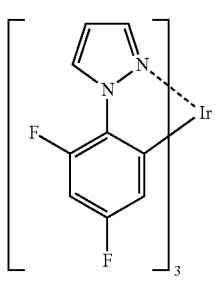
PD5
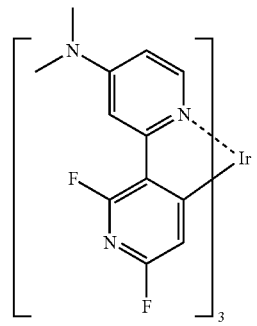
PD6
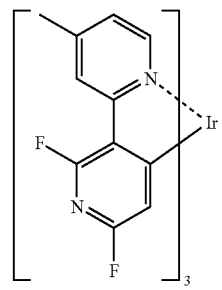
PD7
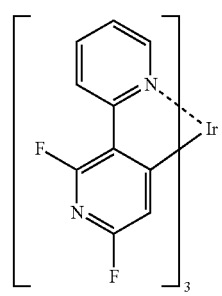
PD8
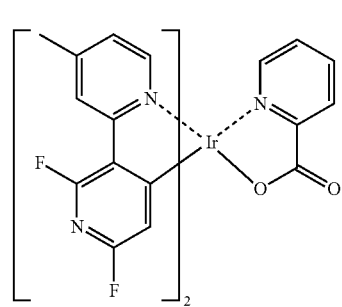
PD9
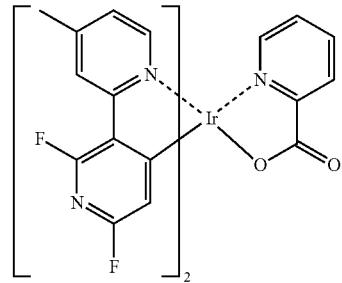

-continued
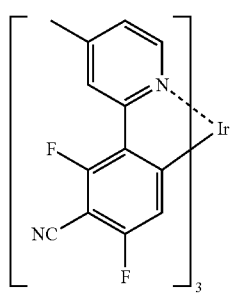
PD10
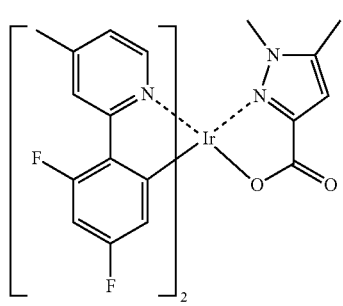
PD11
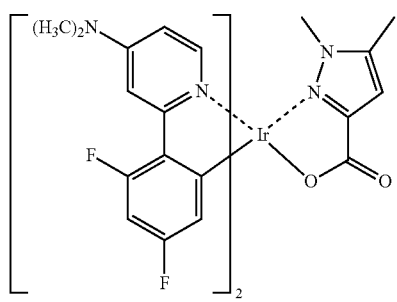
PD12
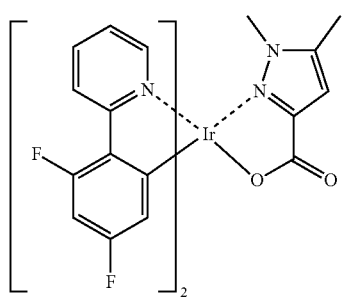
PD13
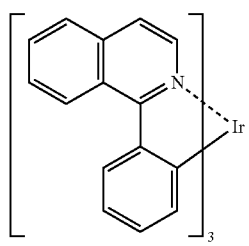
PD14
-continued
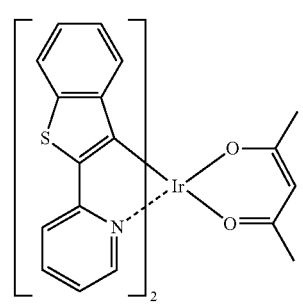
PD15
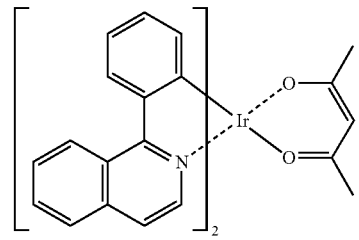
PD16
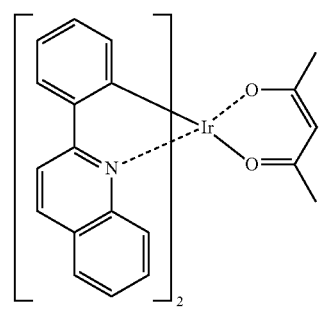
PD17
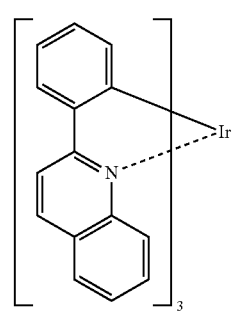
PD18
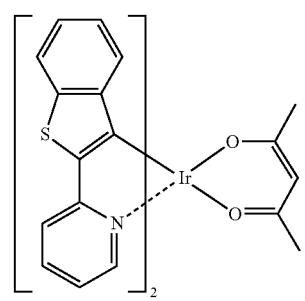
PD19

PD20
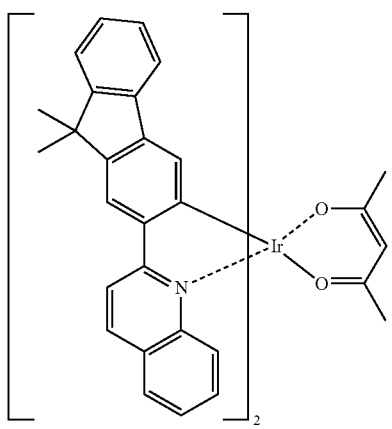
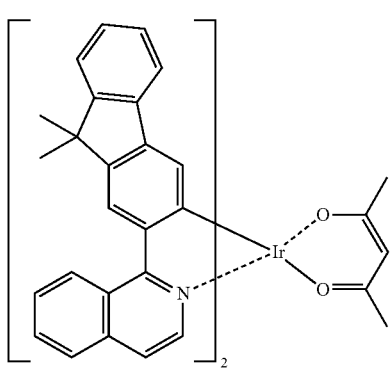
PD22
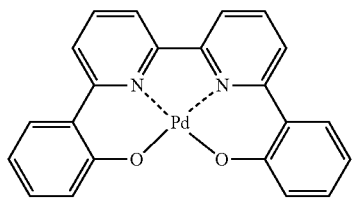
PD23
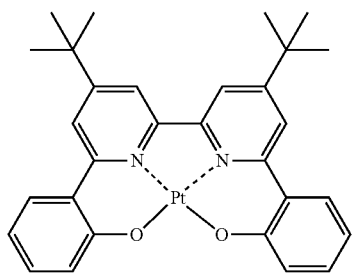
PD24
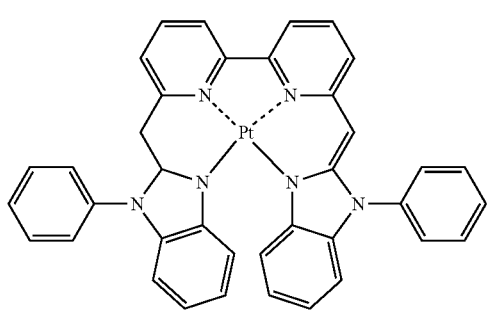
PD25
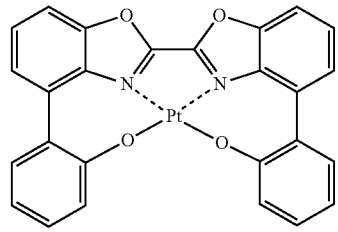
PD26
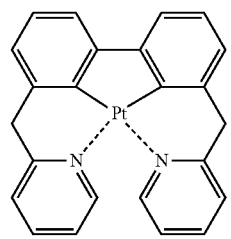
PD27
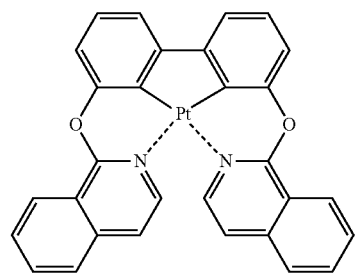
PD28
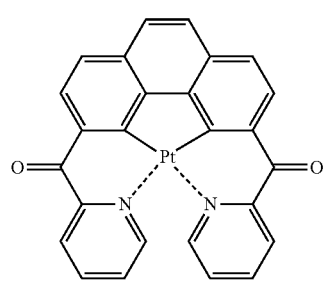
PD29
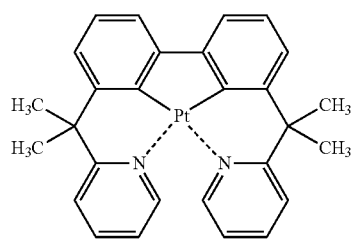
PD30
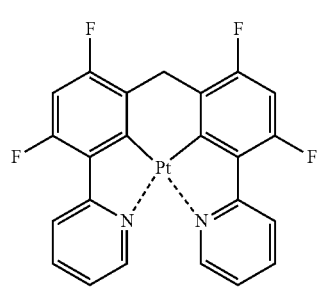

PD31 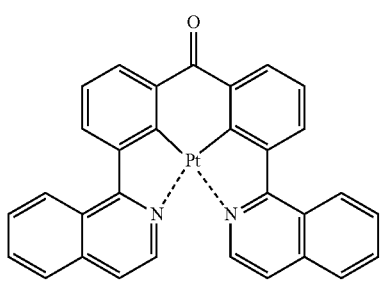
PD32 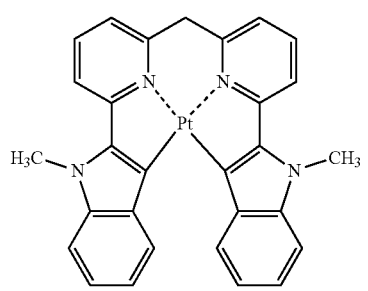
PD33 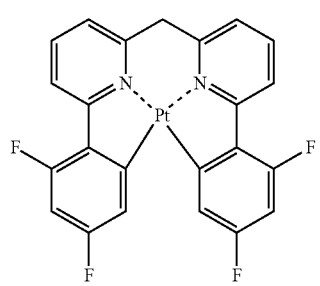
PD34 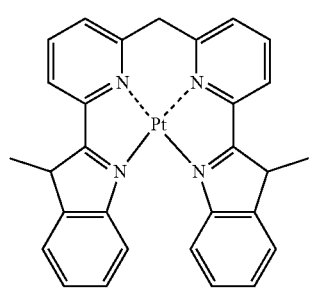
PD35 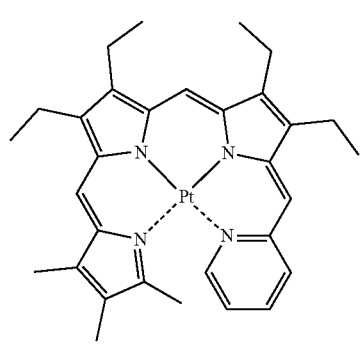
PD36 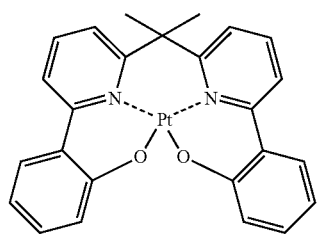
PD37 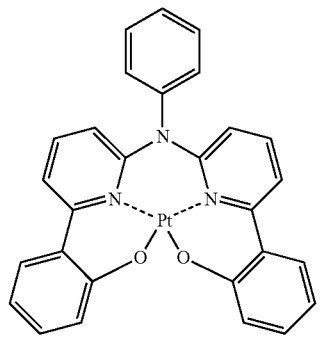
PD38 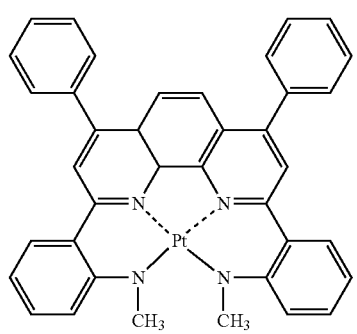
PD39 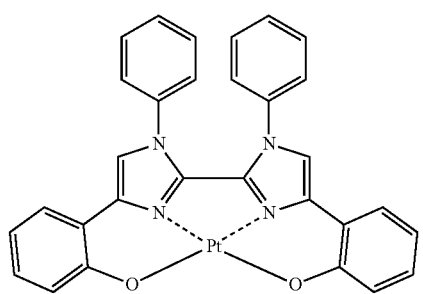
PD40 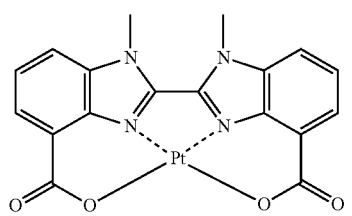
PD41 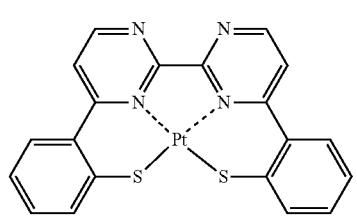

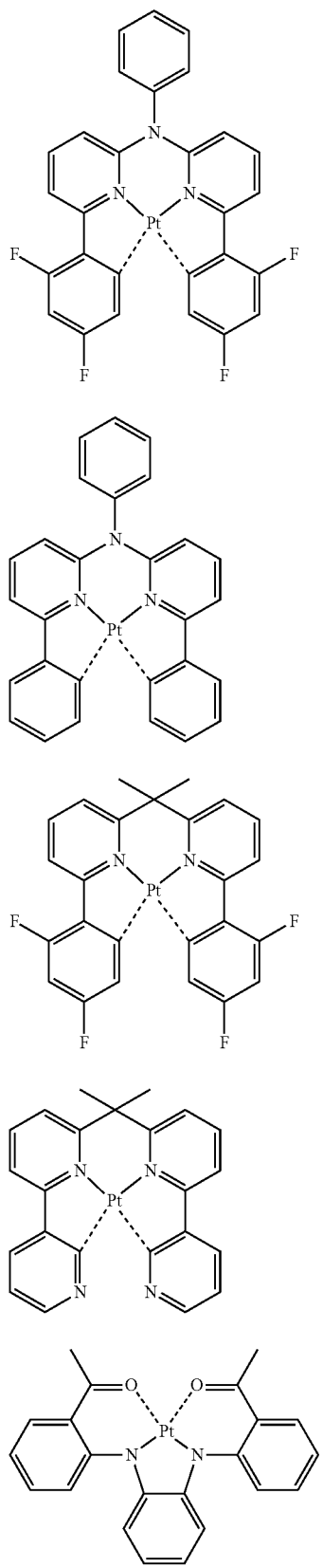
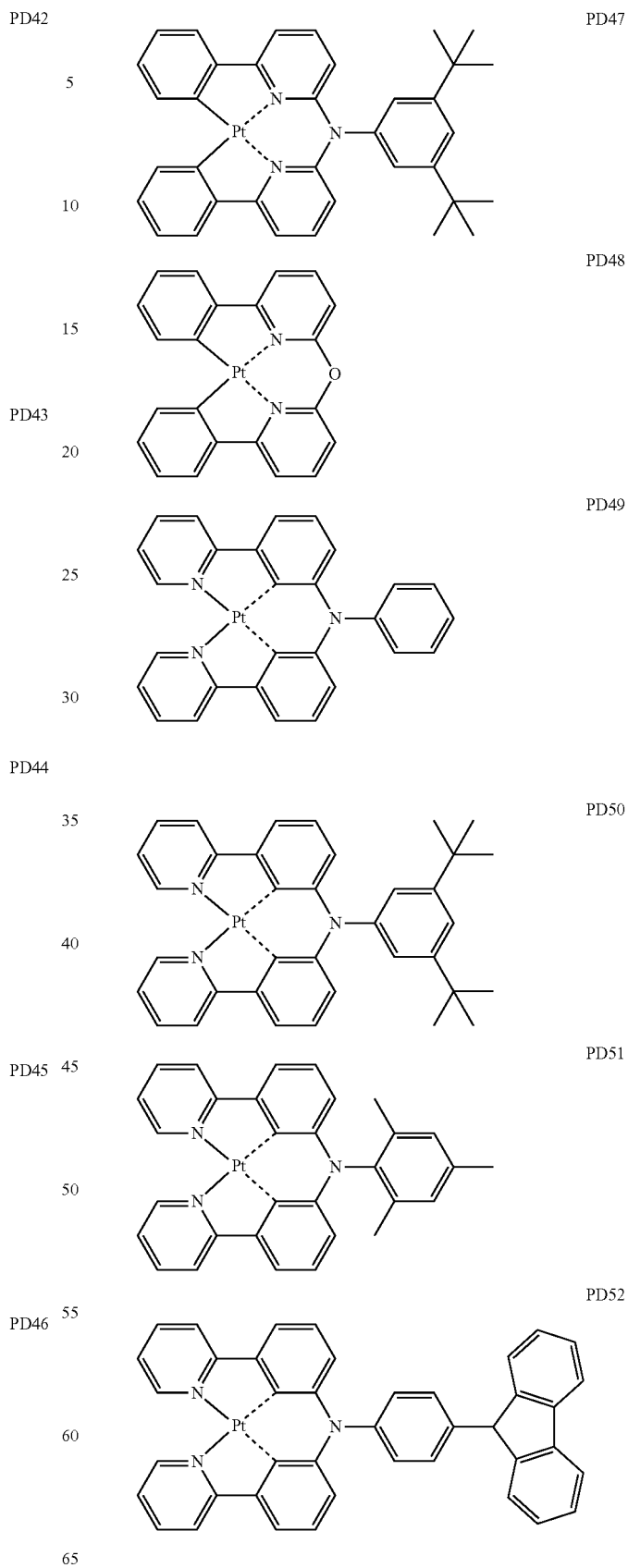

PD53
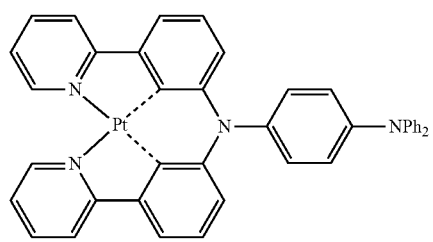
PD58
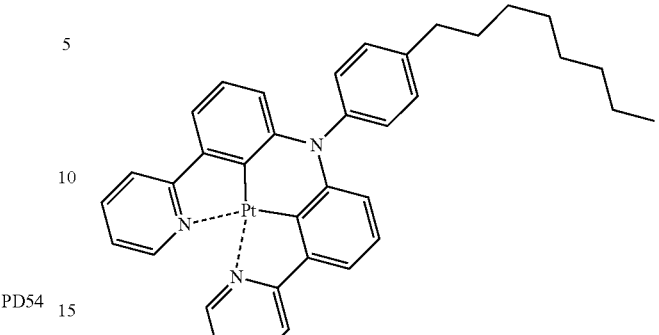
PD54
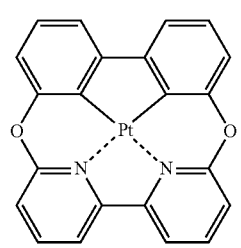
PD59
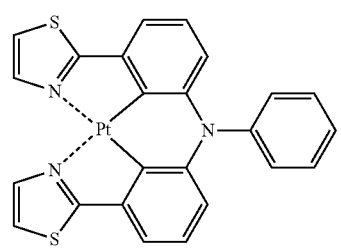
PD55
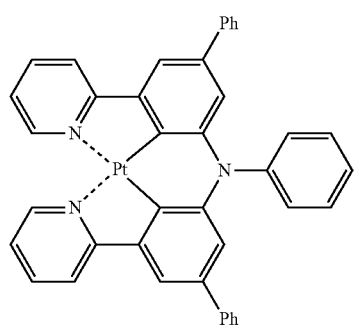
PD60
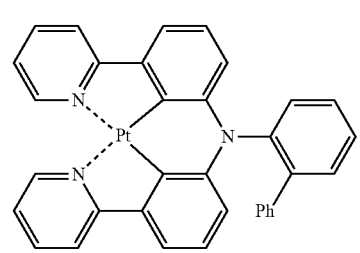
PD56
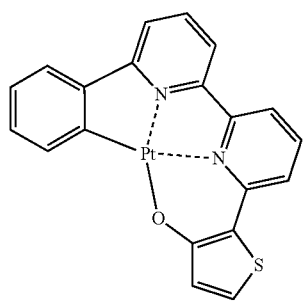
PD61
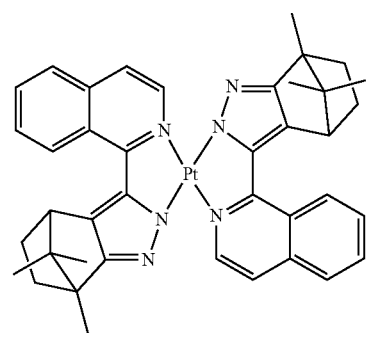
PD57
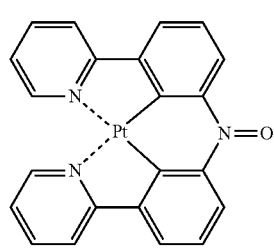
PD62
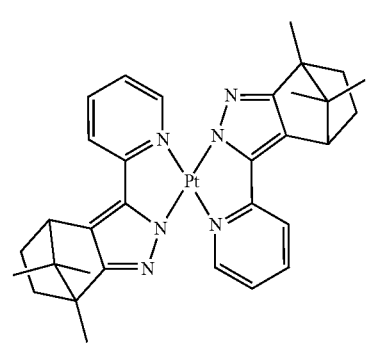

-continued
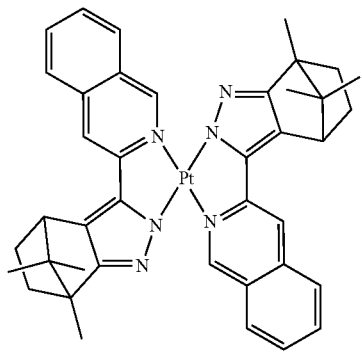
PD63
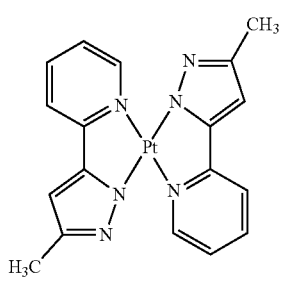
PD64
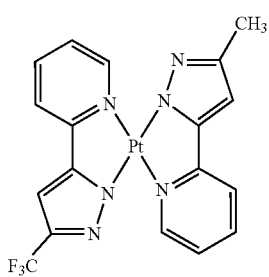
PD65
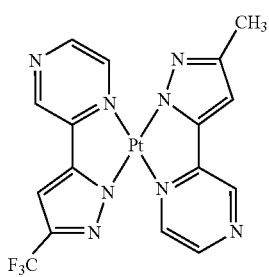
PD66
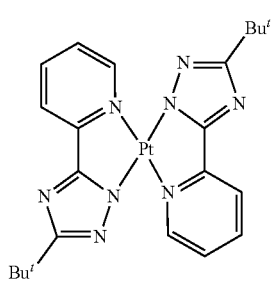
PD67
-continued
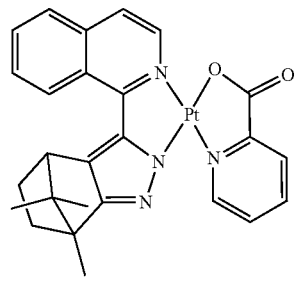
PD68
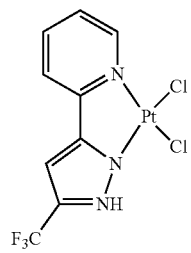
PD69
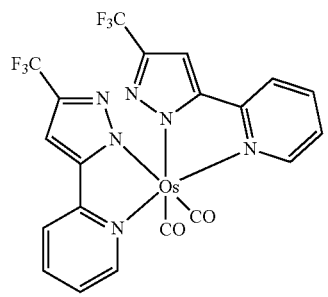
PD70
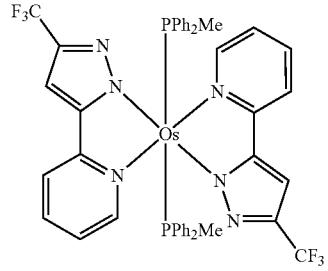
PD71
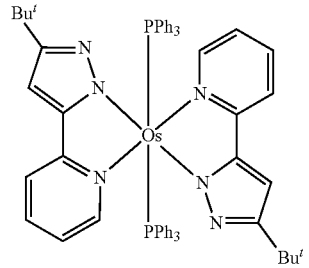
PD72

-continued
PD73
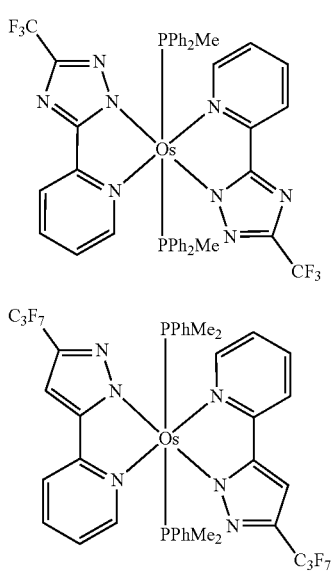
PD74
For example, the phosphorescent dopant may include PtOEP.
PtOEP
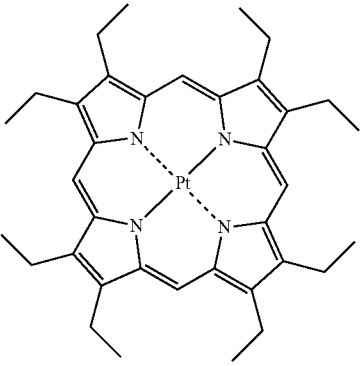
For example, the fluorescent dopant may include at least one of DPAVBi, BDAVBi, TBPe, DCM, DCJTB, Coumarin 6, and C545T.
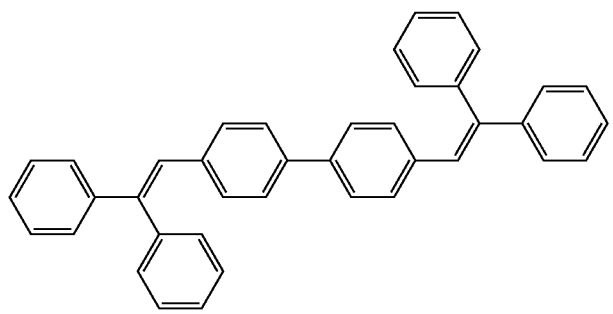
DPVBi
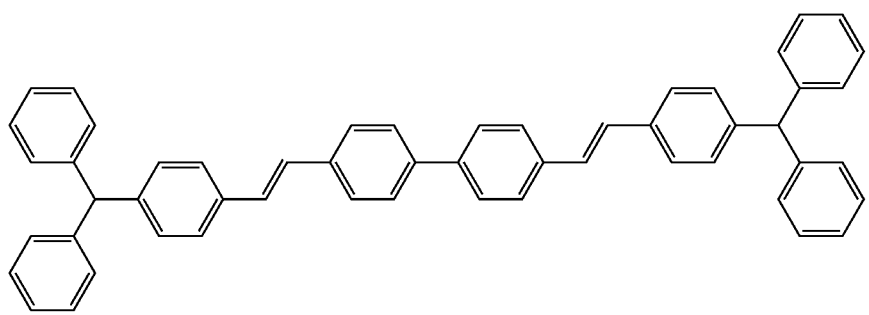
DPAVBi
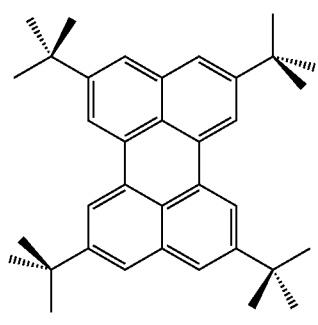
TBPe
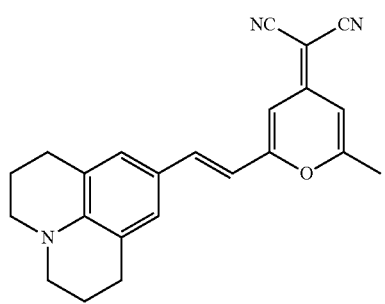
DCM -continued

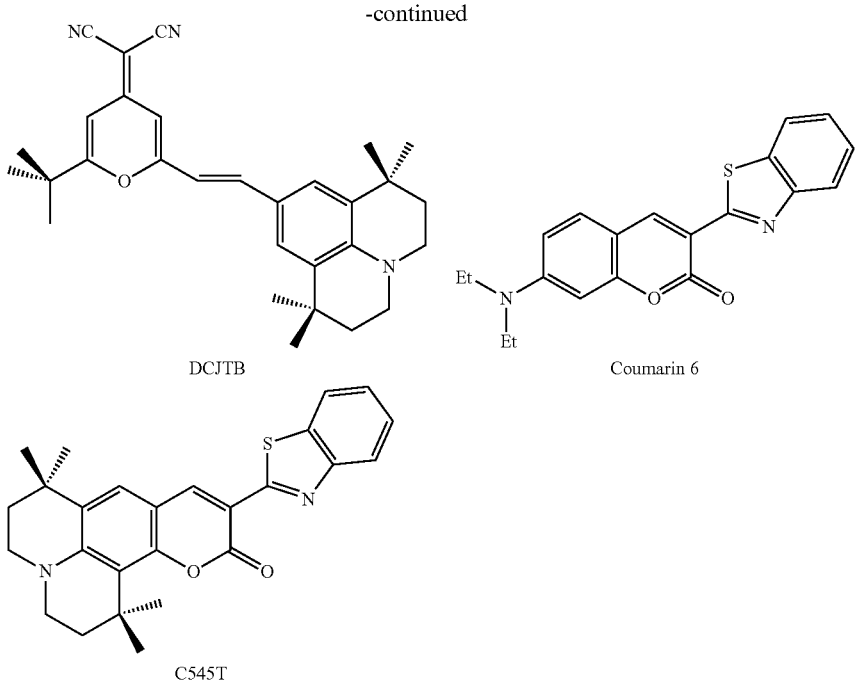

DCJTB

Coumarin 6

C545T

For example, the fluorescent dopant may include a compound represented by Formula 501.

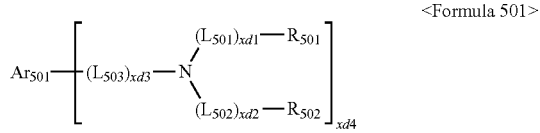

<Formula 501>

In Formula 501,

Ar$_{501}$ may be selected from a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, a monovalent non-aromatic condensed heteropolycyclic group, and —Si($Q_{501}$)($Q_{502}$)($Q_{503}$) (where $Q_{501}$ to $Q_{503}$ are each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group), $L_{501}$ to $L_{503}$ may be defined the same as described above herein in conjunction with $L_{301}$;

$R_{501}$ and $R_{502}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group;

xd1 to xd3 are each independently selected from 0, 1, 2, and 3; and xb4 is selected from 1, 2, 3, and 4.

For example, the fluorescent dopant may include at least one of Compounds FD1 to FD8.

-continued

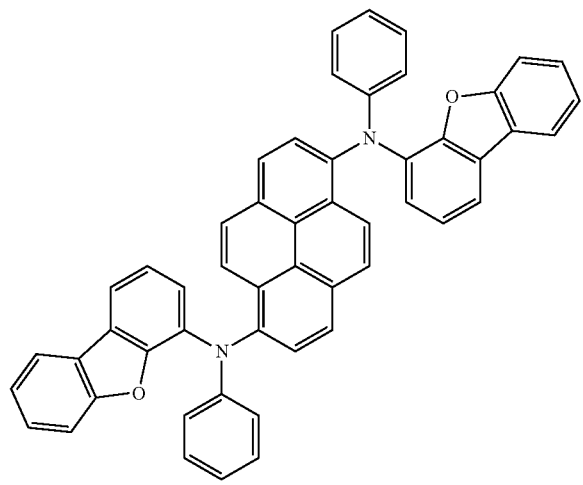
FD5

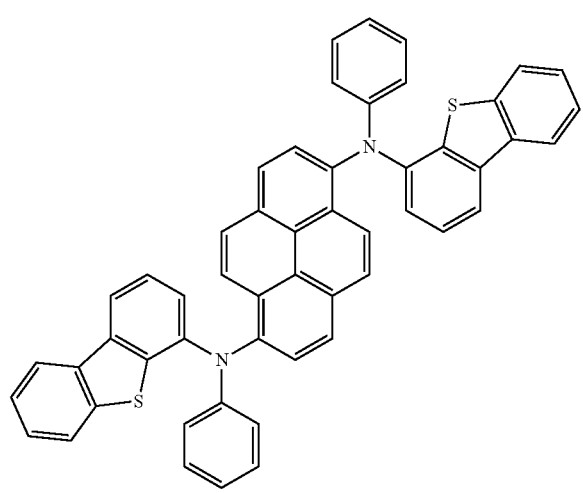
FD6

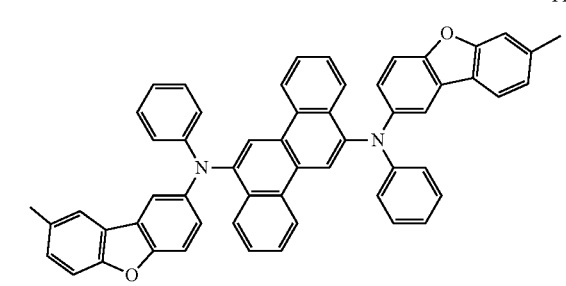
FD7

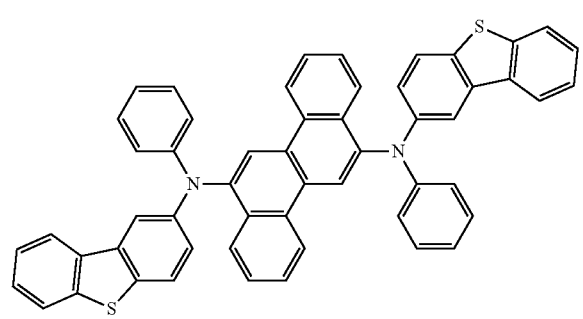
FD8

The amount of the dopant in the EML may be from about 0.01 parts to about 15 parts by weight based on 100 parts by weight of the host.

The thickness of the EML may be about 100 Å to about 1,000 Å, e.g., about 200 Å to about 600 Å. When the thickness of the EML is within these ranges, the EML may have good light emitting ability without a substantial increase in driving voltage.

Next, the electron transport region may be formed on the EML.

The electron transport region may include at least one of a HBL, an ETL, and an EIL.

When the electron transport region includes a HBL, the HBL may be formed on the EML by using any of a variety of methods, e.g., by using vacuum deposition, spin coating, casting, Langmuir-Blodgett (LB) deposition, inkjet printing, laser printing, laser induced thermal imaging (LITI), or the like. When the HBL is formed using vacuum deposition or spin coating, the deposition and coating conditions for forming the HBL may be similar to the above-described deposition and coating conditions for forming the HIL, and accordingly will not be described in detail.

For example, the HBL may include at least one of BCP and Bphen.

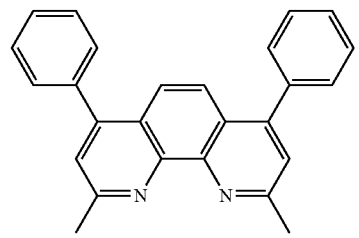
BCP

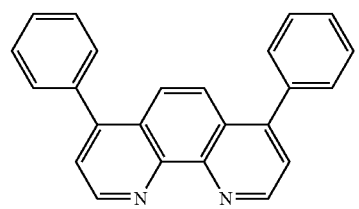
Bphen

The thickness of the HBL may be from about 20 Å to about 1,000 Å, e.g., about 30 Å to about 300 Å. When the thickness of the HBL is within these ranges, the HBL may have satisfactory hole blocking characteristics without a substantial increase in driving voltage.

The electron transport region may have a stack structure including ETL and EIL, or HBL, ETL, and EIL that are sequentially stacked on the EML in the stated order.

In an implementation, the organic layer 150 of the organic light-emitting device may include an electron transport region disposed between the EML and the second electrode 190 and including an ETL. The ETL may include multiple layers. For example, the ETL may include a first electron transport layer and a second electron transport layer.

The ETL may include at least one of BCP, Bphen, Alq$_3$, Balq, TAZ, and NTAZ.

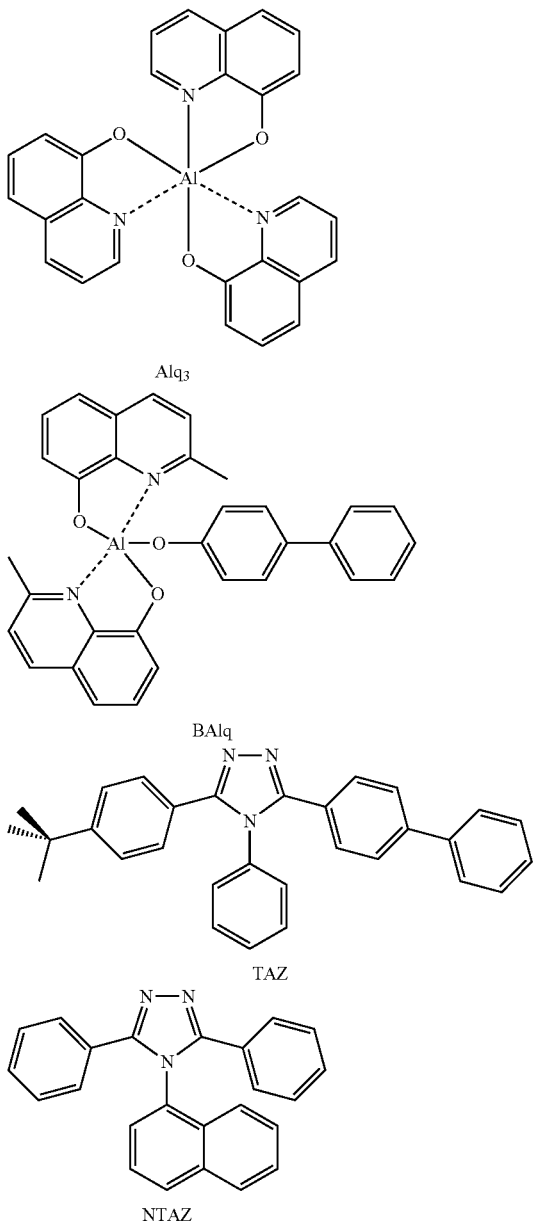

In an implementation, the ETL may include at least one of compounds represented by Formulae 601 and 602.

$$Ar_{601}\text{-}[(L_{601})_{xe1}\text{-}E_{601}]_{xe2} \qquad \text{<Formula 601>}$$

In Formula 601, $Ar_{601}$ may be selected from a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, and a naphthalene group, a heptalene group, a fluorene group, a spiro-fluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ hetero aryl group, a monovalent non-aromatic condensed polycyclic group, a monovalent non-aromatic condensed heteropolycyclic group, and —Si($Q_{301}$)($Q_{302}$)($Q_{303}$) (where $Q_{301}$ to $Q_{303}$ are each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group);

$L_{601}$ may be defined the same as described above herein in conjunction with $L_{301}$;

$E_{601}$ may be selected from a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, and a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coroneryl group, an obarenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and
xe2 may be selected from 1, 2, 3, and 4.

<Formula 602>

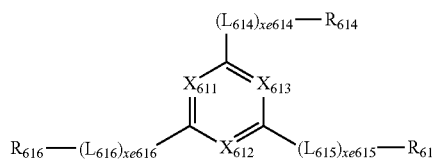

In Formula 602,
$X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, at least one of $X_{611}$ to $X_{613}$ may be N;

$L_{611}$ to $L_{616}$ may be defined the same as described above in conjunction $L_{301}$;

$R_{611}$ to $R_{616}$ may be each independently selected from
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxyl group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from, 0, 1, 2, and 3.

The compound of Formula 601 and the compound of Formula 602 may each independently be selected from Compounds ET1 to ET15.

ET1

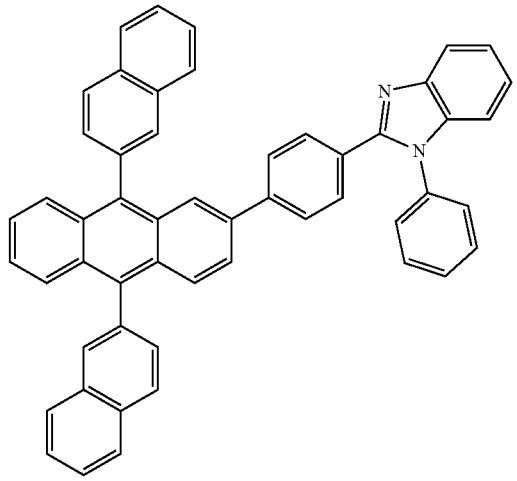

ET2

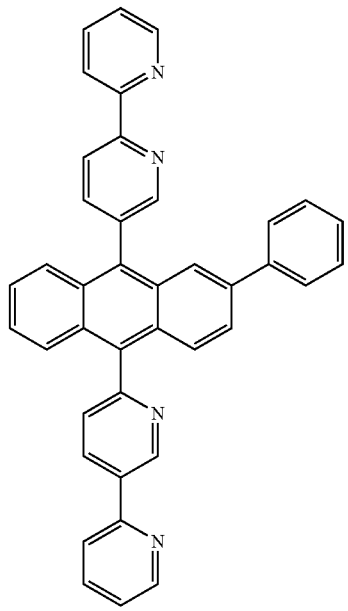

ET3
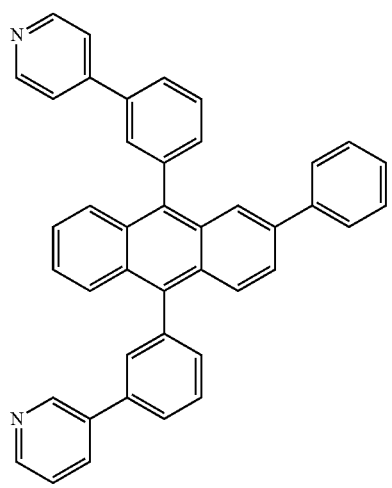
ET4
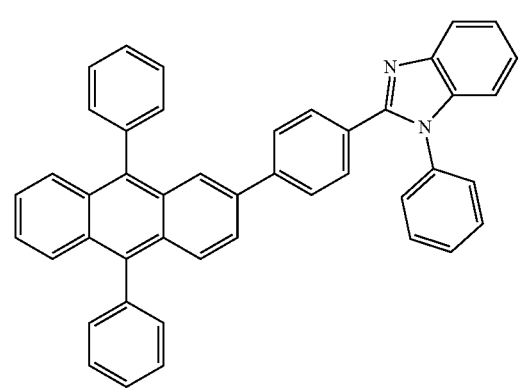
ET5
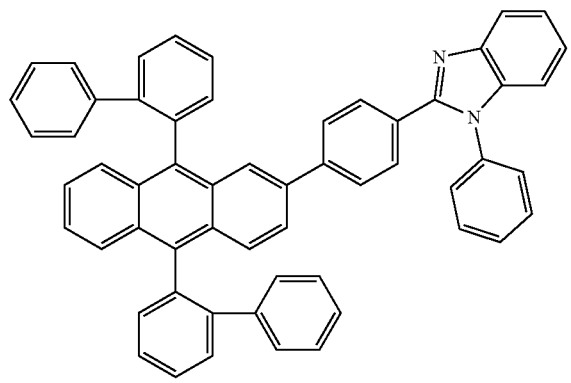
ET6
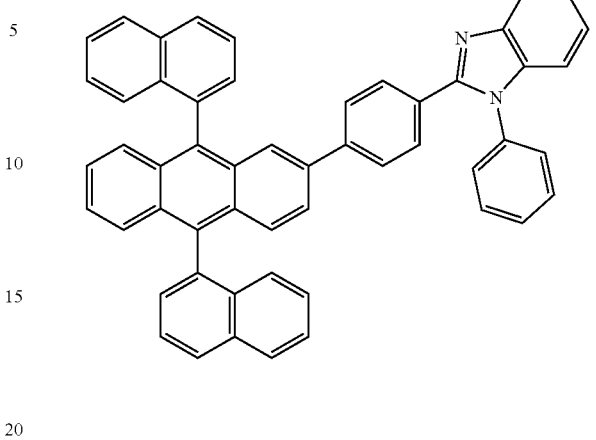
ET7
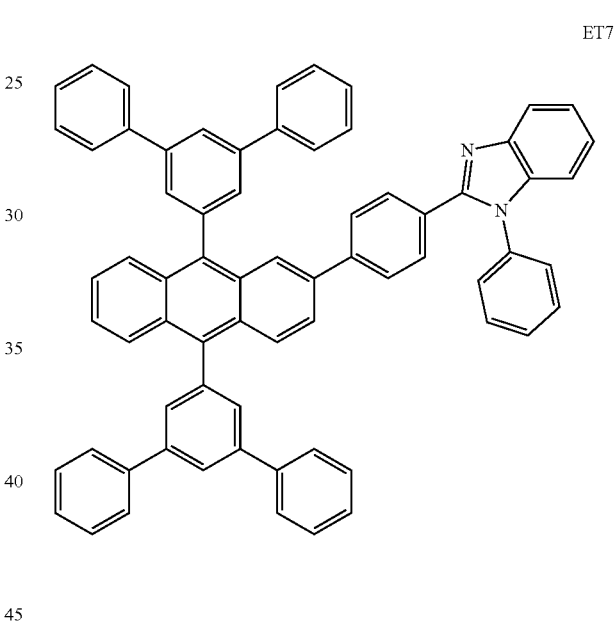
ET8
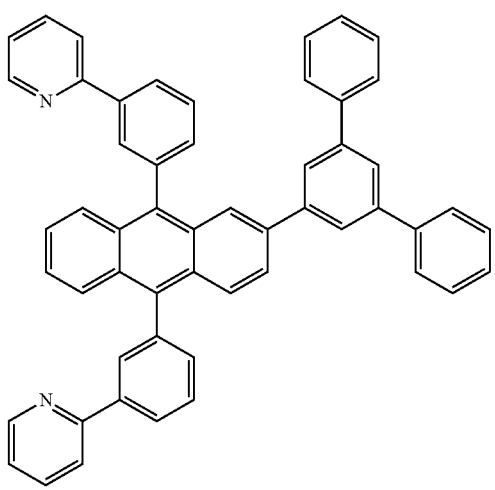

ET9
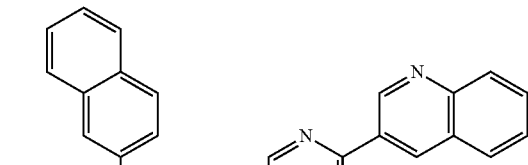
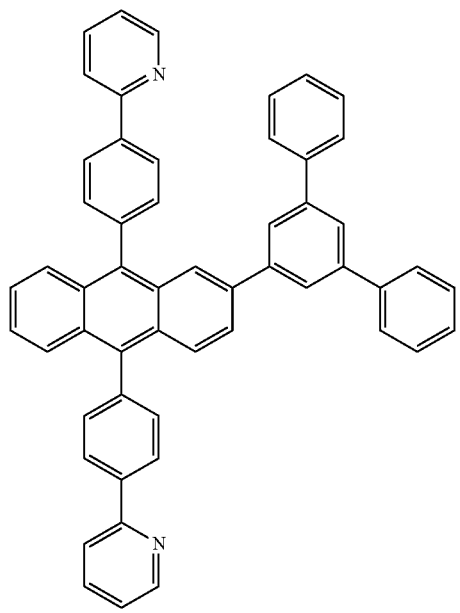
ET11
ET12
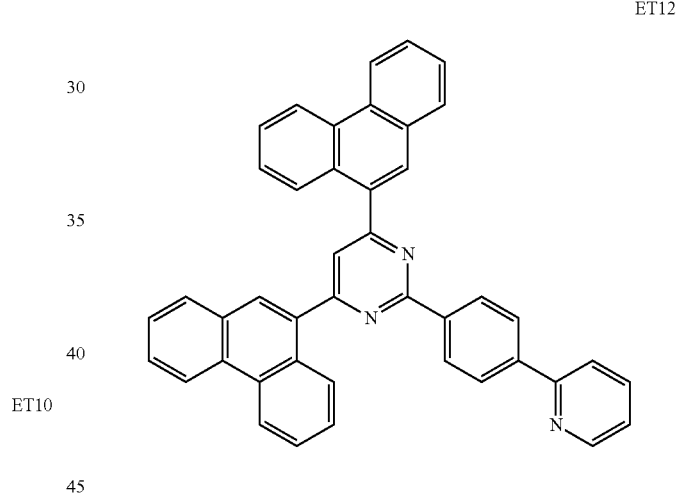
ET10
ET13
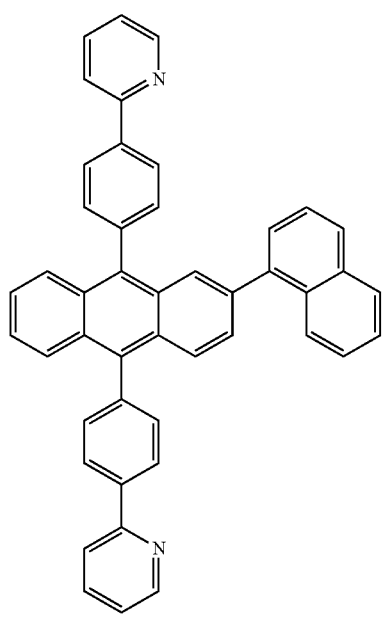
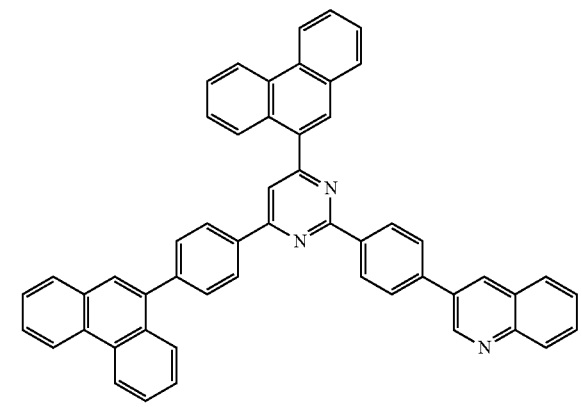

ET14

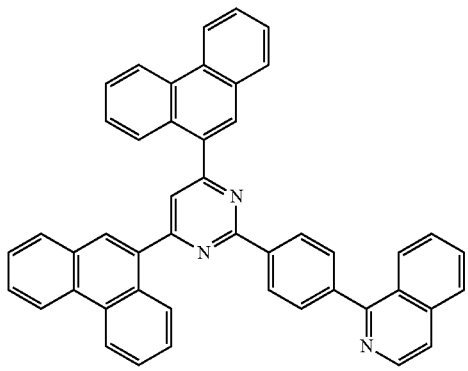

ET15

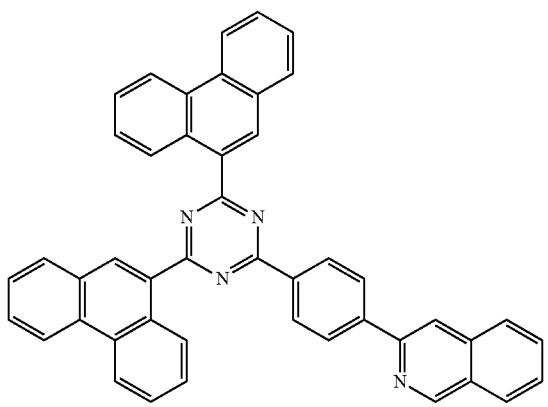

The thickness of the ETL may be from about 100 Å to about 1,000 Å, e.g., from about 150 Å to about 500 Å. When the thickness of the ETL is within these ranges, the ETL may have satisfactory electron transporting ability without a substantial increase in driving voltage.

In an implementation, the ETL may further include a metal-containing material, in addition to the above-described materials.

The metal-containing material may include a lithium (Li) complex. Non-limiting examples of the Li complex may include compound ET-D1 (lithium quinolate (LiQ)), and compound ET-D2.

ET-D1

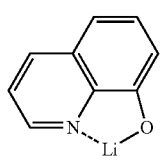

ET-D2

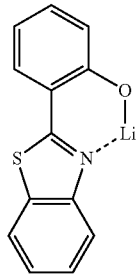

The electron transport region may include an EIL that may facilitate injection of electrons from the second electrode 190.

The EIL may be formed on the ETL by using any of a variety of methods, e.g., by using vacuum deposition, spin coating, casting, Langmuir-Blodgett (LB) deposition, inkjet printing, laser printing, laser induced thermal imaging (LITI), or the like. When the EIL is formed using vacuum deposition or spin coating, the deposition and coating conditions for forming the EIL may be similar to the above-described deposition and coating conditions for forming the HIL, and accordingly will not be described in detail.

The EIL may include at least one selected from LiF, NaCl, CsF, $Li_2O$, BaO, and LiQ.

The thickness of the EIL may be from about 1 Å to about 100 Å, e.g., from about 3 Å to about 90 Å. When the thickness of the EIL is within these ranges, the EIL may have satisfactory electron injection ability without a substantial increase in driving voltage.

The second electrode 190 may be disposed on the organic layer 150, as described above. The second electrode 190 may be a cathode as an electron injecting electrode. A material for forming the second electrode 190 may be a metal, an alloy, an electrically conductive compound, which have a low-work function, or a mixture thereof. Non-limiting examples of materials for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). In an implementation, a material for forming the second electrode 190 may include ITO or IZO. The second electrode 190 may be a reflective electrode, a semi-transmissive electrode, or a transmissive electrode.

In an implementation, the organic layer 150 of the organic light-emitting device 10 may be formed using a compound of Formula 1 according to any of the above-described embodiments by deposition or a wet process of coating a solution of a compound of Formula 1 according to any of the above-described embodiments.

In an implementation, the organic light-emitting device may be included in various types of flat panel display devices, such as in a passive matrix organic light-emitting display device or in an active matrix organic light-emitting display device. For example, when the organic light-emitting device is included in an active matrix organic light-emitting display device including a thin-film transistor, the first electrode on the substrate as a pixel electrode may be electrically connected to a source electrode or a drain electrode of the thin-film transistor. In an implementation, the organic light-emitting device may also be included in a flat panel display devices having a double-sided screen.

Hereinafter, substituents described with reference to the formulae will now be described in detail. In this regard, the numbers of carbons in substituents are presented only for illustrative purposes and do not limit the characteristics of the substituents. The substituents not defined herein are construed as having common meanings understood by one of ordinary skill in the art.

As used herein, a $C_1$-$C_{60}$ alkyl group refers to a linear or branched aliphatic hydrocarbon monovalent group having 1 to 60 carbon atoms. Non-limiting examples of the $C_1$-$C_{60}$ alkyl group, a methyl group, an ethyl group, a propyl group, an isobutyl group, a sec-butyl group, a tert-butyl group, a pentyl group, an iso-amyl group, and a hexyl group. A $C_1$-$C_{60}$ alkylene group refers to a divalent group having the same structure as the $C_1$-$C_{60}$ alkyl.

As used herein, a $C_1$-$C_{60}$ alkoxy group refers to a monovalent group represented by —$OA_{101}$ (where $A_{101}$ is a $C_1$-$C_{60}$) alkyl group, as described above. Non-limiting examples of the $C_1$-$C_{60}$ alkoxy group are a methoxy group, an ethoxy group, and an isopropyloxy group.

As used herein, a $C_2$-$C_{60}$ alkenyl group refers to a hydrocarbon group including at least one carbon double bond in the middle or terminal of the $C_2$-$C_{60}$ alkyl group. Non-limiting examples of the $C_2$-$C_{60}$ alkenyl group are an ethenyl group, a prophenyl group, and a butenyl group. A $C_2$-$C_{60}$ alkylene group refers to a divalent group having the same structure as the $C_2$-$C_{60}$ alkenyl group.

As used herein, a $C_2$-$C_{60}$ alkynyl group refers to a hydrocarbon group including at least one carbon triple bond in the middle or terminal of the $C_2$-$C_{60}$ alkyl group. Non-limiting examples of the $C_2$-$C_{60}$ alkynyl group are an ethynyl group, and a propynyl group. A $C_2$-$C_{60}$ alkynylene group used herein refers to a divalent group having the same structure as the $C_2$-$C_{60}$ alkynyl group.

As used herein, a $C_3$-$C_{10}$ cycloalkyl group refers to a monovalent, monocyclic hydrocarbon group having 3 to 10 carbon atoms. Non-limiting examples of the $C_3$-$C_{10}$ cycloalkyl group are a cyclopropyl group, a cyclobutyl group, a cyclopentyl group, a cyclohexyl group, and a cycloheptyl group. A $C_3$-$C_{10}$ cycloalkylene group refers to a divalent group having the same structure as the $C_3$-$C_{10}$ cycloalkyl group.

As used herein, a $C_1$-$C_{10}$ heterocycloalkyl group refers to a monovalent monocyclic group having 1 to 10 carbon atoms in which at least one hetero atom selected from N, O, P, and S is included as a ring-forming atom. Non-limiting examples of the $C_2$-$C_{10}$ heterocycloalkyl group are a tetrahydrofuranyl group, and a tetrahydrothiophenyl group. A $C_2$-$C_{10}$ heterocycloalkylene group refers to a divalent group having the same structure as the $C_2$-$C_{10}$ heterocycloalkyl group.

As used herein, a $C_3$-$C_{10}$ cycloalkenyl group refers to a monovalent monocyclic group having 3 to 10 carbon atoms that includes at least one double bond in the ring but does not have aromaticity. Non-limiting examples of the $C_3$-$C_{10}$ cycloalkenyl group are a cyclopentenyl group, a cyclohexenyl group, and a cycloheptenyl group. A $C_3$-$C_{10}$ cycloalkenylene group refers to a divalent group having the same structure as the $C_3$-$C_{10}$ cycloalkenyl group.

As used herein, a $C_2$-$C_{10}$ heterocycloalkenyl group used herein refers to a monovalent monocyclic group having 2 to 10 carbon atoms that includes at least one double bond in the ring and in which at least one hetero atom selected from N, O, P, and S is included as a ring-forming atom. Non-limiting examples of the $C_2$-$C_{10}$ heterocycloalkenyl group are a 2,3-hydrofuranyl group, and a 2,3-hydrothiophenyl group. A $C_2$-$C_{10}$ heterocycloalkenylene group used herein refers to a divalent group having the same structure as the $C_2$-$C_{10}$ heterocycloalkenyl group.

As used herein, a $C_6$-$C_{60}$ aryl group refers to a monovalent, aromatic carbocyclic aromatic group having 6 to 60 carbon atoms, and a $C_6$-$C_{60}$ arylene group refers to a divalent, aromatic carbocyclic group having 6 to 60 carbon atoms. Non-limiting examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group, and the $C_6$-$C_{60}$ arylene group include at least two rings, the rings may be fused to each other.

As used herein, a $C_1$-$C_{60}$ heteroaryl group refers to a monovalent, aromatic carbocyclic aromatic group having 1 to 60 carbon atoms and at least one hetero atom selected from N, O, P, and S as a ring-forming atom. A $C_1$-$C_{60}$ heteroarylene group refers to a divalent, aromatic carbocyclic group having 1 to 60 carbon atoms, and at least one hetero atom selected from N, O, P, and S as a ring-forming atom. Non-limiting examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group include at least two rings, the rings may be fused to each other.

As used herein, a $C_6$-$C_{60}$ aryloxy group indicates —$OA_{102}$ (where $A_{102}$ is a $C_6$-$C_{60}$ aryl group, as described above), and a $C_6$-$C_{60}$ arylthio group indicates —$SA_{103}$ (where $A_{103}$ is a $C_6$-$C_{60}$ aryl group, as described above).

As used herein, a monovalent non-aromatic condensed polycyclic group (including, for example, 8 to 60 carbon atoms) refers to a monovalent group that includes at least two rings condensed to each other and includes only carbon atoms as ring-forming atoms and that represents non-aromaticity as a whole. An example of the monovalent non-aromatic condensed polycyclic group is a fluorenyl group. As used herein, a divalent non-aromatic condensed polycyclic group refers to a divalent group with the same structure as the monovalent non-aromatic condensed polycyclic group.

As used herein, a monovalent non-aromatic condensed heteropolycyclic group (including, for example, 2 to 60 carbon atoms) refers to a monovalent group that includes at least two rings condensed to each other and include carbon and hetero atoms selected from N, O, P and S as ring-forming atoms and that represents non-aromaticity as a whole. An example of the monovalent non-aromatic condensed heteropolycyclic group is a carbazolyl group. As used herein, a divalent non-aromatic condensed heteropolycyclic group refers to a divalent group with the same structure as the monovalent non-aromatic condensed polycyclic group.

As used herein, at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$, and —$N(Q_{31})(Q_{32})$, —$Si(Q_{33})(Q_{34})(Q_{35})$, and —$B(Q_{36})(Q_{37})$, wherein $Q_{11}$ to $Q_{17}$, $Q_{21}$ to $Q_{27}$ and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

For example, at least one substituent of the substituted $C_3$-$C_{10}$ cycloalkylene group, the substituted $C_2$-$C_{10}$ heterocycloalkylene group, substituted $C_3$-$C_{10}$ cycloalkenylene group, the substituted $C_2$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —$N(Q_{11})(Q_{12})$, —$Si(Q_{13})(Q_{14})(Q_{15})$, and —$B(Q_{16})(Q_{17})$, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$) and —B($Q_{26}$)($Q_{27}$), and —N($Q_{31}$)($Q_{32}$), —Si($Q_{33}$)($Q_{34}$)($Q_{35}$), and —B($Q_{36}$)($Q_{37}$), wherein $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

As used herein, "Ph" denotes a phenyl group, "Me" denotes a methyl group, "Et" denotes an ethyl group, "ter-Bu" or "Bu$^t$" denotes a tert-butyl group.

One or more embodiments of the present disclosure will now be described in detail with reference to the following examples including synthesis examples. However, these examples are only for illustrative purposes and are not intended to limit the scope of the one or more embodiments of the present disclosure.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1: Synthesis of Compound 1

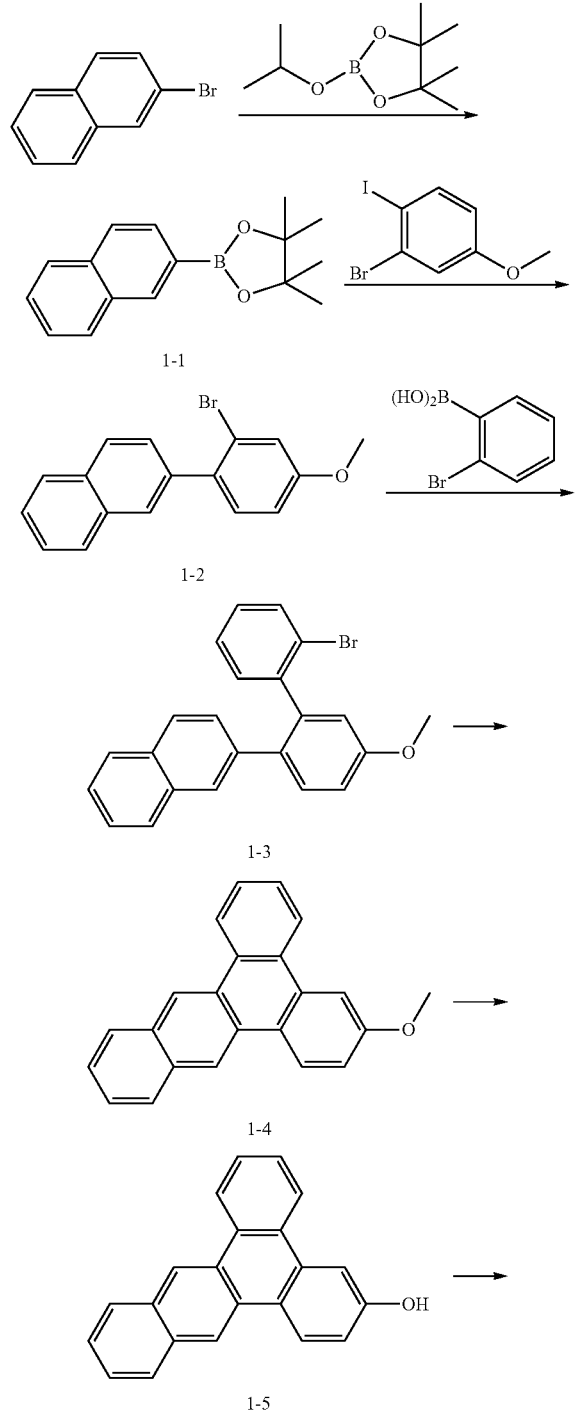

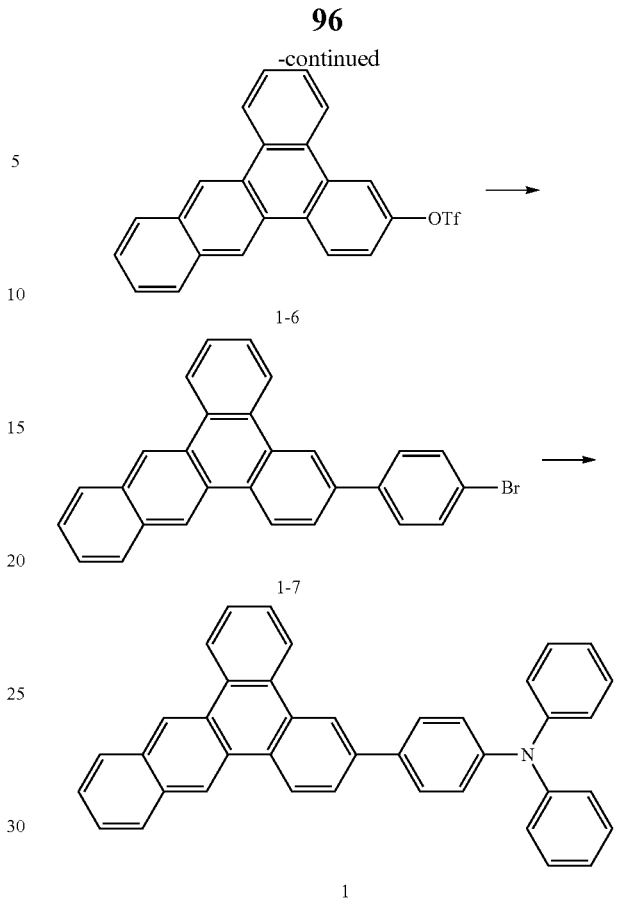

(1) Synthesis of Intermediate 1-1

20.0 g (20 mmol) of 2-bromonaphthalene was dissolved in 50 mL of tetrahydrofuran (THF), and then 8.8 mL (22.0 mmol) of n-BuLi (2.5 M in hexane) was slowly dropwise added thereto at about −78° C. After the reaction solution was stirred at the same temperature for about 1 hour, 4.65 mL (25.0 mmol) of 2-isoproxy-4,4,5,5,-tetramethyl-1,3,2-dioxaborolane was slowly dropwise added to the reaction solution, stirred at about −78° C. for about 1 hour, and then further stirred at ambient temperature for about 24 hours. After termination of the reaction, 30 mL of a 10% HCl aqueous solution and 30 mL of $H_2O$ were added thereto, followed by extraction three times with 50 ml of diethyl ether. An organic phase was collected and dried using magnesium sulfate, followed by evaporating the solvent. The resulting residue was purified by silica gel column chromatography to obtain 3.7 g of Intermediate 1-1 (Yield: 73%). This compound was identified by liquid chromatography-mass spectrometry (LC-MS). $C_{16}H_{19}BO_2$:$M^+$ 255.1

(2) Synthesis of Intermediate 1-2

2.5 g (10.0 mmol) of Intermediate 1-1, 3.4 g (11.0 mmol) of 2-bromo-1-iodo-4-methoxy benzene, 0.58 g (0.5 mmol) of $Pd(PPh_3)_4$, and 2.1 g (15.0 mmol) of $K_2CO_3$ were dissolved in 40 mL of a mixed solution of THF and $H_2O$ (2:1 by volume) and stirred at about 80° C. for about 5 hours. After the resulting reaction solution was cooled down to ambient temperature, 40 mL of water was added thereto, followed by extraction three times with 50 mL of diethyl ether. An organic phase was collected and dried using magnesium sulfate, followed by evaporating the solvent. The resulting residue was purified by silica gel column chromatography to obtain 2.3 g of Intermediate 1-2 (Yield: 72%). This compound was identified by LC-MS. $C_{17}H_{13}BrO$ $M^+$ 313.1

(3) Synthesis of Intermediate 1-3

3.13 g (10.0 mmol) of Intermediate 1-2, 2 g (10.0 mmol) of (2-bromophenyl)boronic acid, 0.58 g (0.5 mmol) of Pd(PPh$_3$)$_4$, and 2.1 g (15.0 mmol) of K$_2$CO$_3$ were dissolved in 40 mL of a mixed solution of THF and H$_2$O (2:1 by volume) and stirred at about 80° C. for about 5 hours. After the resulting reaction solution was cooled down to ambient temperature, 40 mL of water was added thereto, followed by extraction three times with 50 mL of diethyl ether. An organic phase was collected and dried using magnesium sulfate, followed by evaporating the solvent. The resulting residue was purified by silica gel column chromatography to obtain 2.9 g of Intermediate 1-3 (Yield: 75%). This compound was identified by LC-MS. C$_{23}$H$_{17}$BrO M$^+$ 389.1

(4) Synthesis of Intermediate 1-4

10 mmol of Intermediate 1-3, 1.4 mmol of palladium(II) acetate, 2.8 mmol of PCy$_3$-HBF$_4$, and 6 mmol of K$_2$CO$_3$ were dissolved in 100 mL of N—N-dimethyl acetamide (DMA) and stirred at about 140° C. for about 4 hours. After the resulting reaction solution was cooled down to ambient temperature, 30 mL of water and 30 mL of toluene were added thereto, followed by extraction three times with 50 mL of diethyl ether. An organic phase was collected and dried using magnesium sulfate, followed by evaporating the solvent. The resulting residue was purified by silica gel column chromatography to obtain 2.2 g of Intermediate 1-4 (Yield: 73%). This compound was identified by LC-MS. C$_{23}$H$_{16}$O M$^+$ 309.1

(5) Synthesis of Intermediate 1-5

After 3.08 g (10 mmol) of Intermediate 1-4 was diluted with 500 mL of dichloromethane, 15 mL of tribromoboron was slowly dropwise added thereto. After about 3 hours, the reaction was terminated at about 0° C. with a saturated sodium bicarbonate aqueous solution, followed by phase separation to obtain an organic phase. The organic phase was dried using anhydrous magnesium sulfate and concentrated under reduced pressure. The resulting residue was purified by silica gel column chromatography to obtain 2.6 g of Intermediate 1-5 (Yield: 89%). This compound was identified by LC-MS. C$_{22}$H$_{14}$O M$^+$ 295.1

(6) Synthesis of Intermediate 1-6

After 4.4 g (15 mmol) of Intermediate 1-5 was diluted with 600 mL of dichloromethane, 31 mL of triethylamine was dropwise added thereto and then 48 g of anhydrous trifluoroacetic acid was slowly dropwise added thereto at about 0° C. The reaction solution was stirred at ambient temperature for about 3 hours, and then the reaction was terminated with water. An organic phase was collected, dried using anhydrous magnesium sulfate, and then concentrated under reduced pressure. The resulting residue was purified by silica gel column chromatography to obtain 6.1 g of Intermediate 1-6 (Yield: 96%). This compound was identified by LC-MS. C$_{23}$H$_{13}$F$_3$O$_3$S M$^+$ 427.1

(7) Synthesis of Intermediate 1-7

3.6 g of Intermediate 1-7 (Yield: 82%) was obtained in the same manner as in the synthesis of Intermediate 1-3, except that 4.3 g (10 mmol) of Intermediate 1-6, instead of Intermediate 1-2, and 2.4 g of 4-bromophenyl)boronic acid were used. This compound was identified by LC-MS. C$_{28}$H$_{17}$Br M$^+$ 434.1

(8) Synthesis of Compound 1

4.3 g (10 mmol) of Intermediate 1-7, 3.7 g (22 mmol) of diphenylamine, 0.36 g (0.4 mmol) of Pd$_2$(dba)$_3$, 0.04 g (0.4 mmol) of PtBu$_3$, and 4 g (40 mmol) of KOtBu were dissolved in 80 mL of toluene and stirred at about 85° C. for about 2 hours. The resulting reaction solution was cooled down to ambient temperature, followed by extraction three times with 50 mL of water and 50 mL of diethyl ether 50 mL. An organic phase was collected and dried using magnesium sulfate, followed by evaporating the solvent. The resulting residue was purified by silica gel column chromatography to obtain 4.2 g of Compound 1 (Yield: 81%). This compound was identified by fast atom bombardment mass spectrometry (MS/FAB) and $^1$H nuclear magnetic resonance (NMR). C$_{40}$H$_{27}$N cal. 521.21. found 522.21.

$^1$H NMR (CDCl$_3$, 400 MHz) 9.01-8.99 (d, 2H), 8.71-8.64 (m, 2H), 8.46 (d, 1H), 8.28-8.26 (d, 2H), 8.01-7.95 (m, 2H), 7.67-7.45 (m, 6H), 7.08-7.04 (m, 4H), 6.85-6.84 (m, 2H), 6.66-6.63 (m, 2H), 6.16-6.13 (m, 4H)

Synthesis Example 2: Synthesis of Compound 23

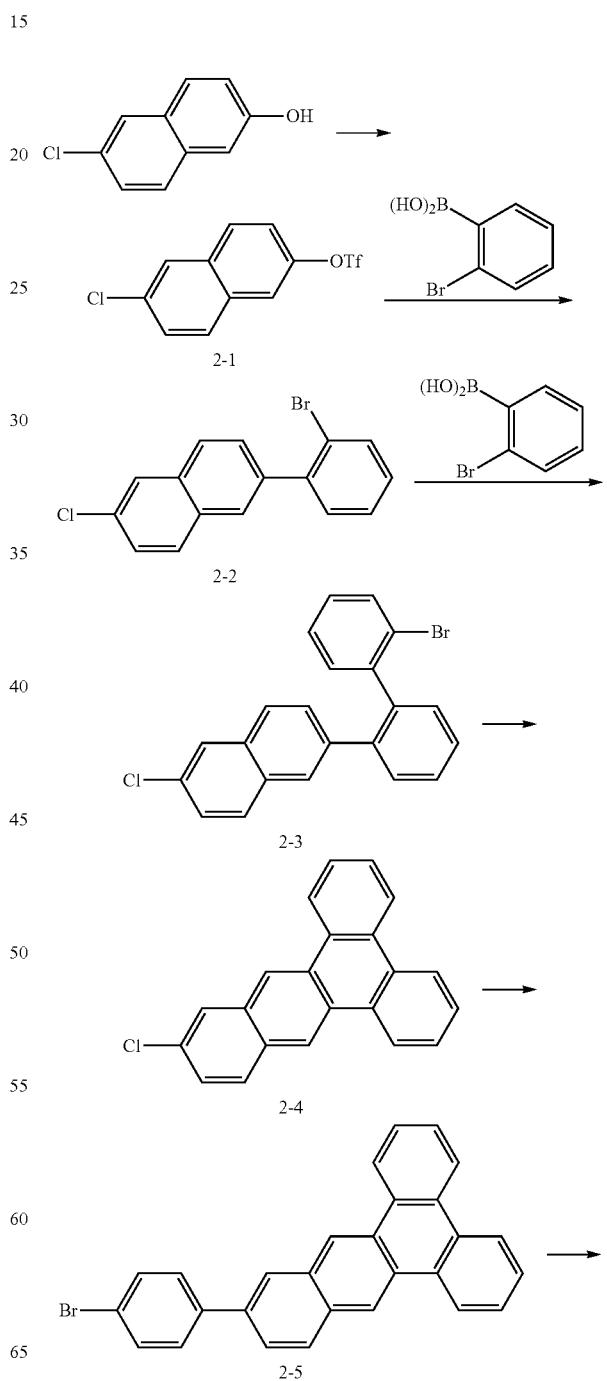

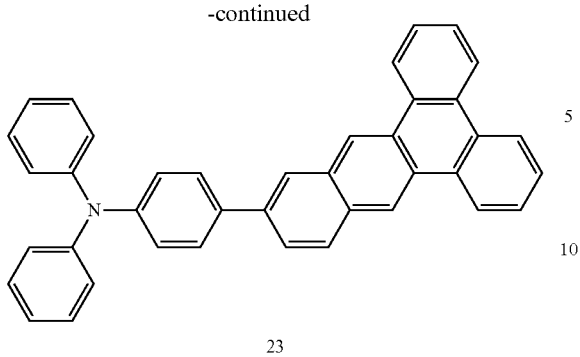

23

(1) Synthesis of Intermediate 2-1

2.8 g (Yield: 91%) of Intermediate 2-1 was obtained in the same manner as in the synthesis of Intermediate 1-6, except that 2.7 g (15 mmol) of 6-chloronaphthalene-2-ol, instead of Intermediate 1-5, was used. This compound was identified by LC-MS. $C_{11}H_6ClF_3O_3S$ $M^+$ 311.1

(2) Synthesis of Intermediate 2-2

2.5 g (Yield: 77%) of Intermediate 2-2 was obtained in the same manner as in the synthesis of Intermediate 1-6, except that 3.1 g (10.0 mmol) of Intermediate 2-1, instead of Intermediate 1-2, was used. This compound was identified by LC-MS. $C_{16}H_{10}BrCl$ $M^+$ 317.1

(3) Synthesis of Intermediate 2-3

3.1 g (Yield: 80%) of Intermediate 2-3 was obtained in the same manner as in the synthesis of Intermediate 1-6, except that 3.1 g (10.0 mmol) of Intermediate 2-2, instead of Intermediate 1-2, was used. This compound was identified by LC-MS. $C_{22}H_{14}BrCl$ $M^+$ 317.1

(4) Synthesis of Intermediate 2-4

2.3 g (Yield: 75%) of Intermediate 2-4 was obtained in the same manner as in the synthesis of Intermediate 1-4, except that Intermediate 2-3, instead of Intermediate 1-3, was used. This compound was identified by LC-MS. $C_{22}H_{13}Cl$ $M^+$ 313.1

(5) Synthesis of Intermediate 2-5

3.6 g (Yield: 82%) of Intermediate 2-5 was obtained in the same manner as in the synthesis of Intermediate 1-7, except that 3.12 g (10 mmol) of Intermediate 2-4, instead of Intermediate 1-6, was used. This compound was identified by LC-MS. $C_{28}H_{17}Br$ $M^+$ 433.1

(6) Synthesis of Compound 23

4.4 g (Yield: 85%) of Compound 23 was obtained in the same manner as in the synthesis of Compound 1, except that 4.33 g (10 mmol) of Intermediate 2-5, instead of Intermediate 1-7, was used. This compound was identified by MS/FAB and $^1$H NMR. $C_{40}H_{27}N$ cal. 521.21. found 522.21.

$^1$H NMR (CDCl$_3$, 400 MHz) 9.29 (s, 1H), 9.02 (s, 1H), 8.74-8.68 (m, 2H), 8.52-8.48 (m, 2H), 8.39 (s, 1H), 8.07-8.05 (d, 1H), 7.90-7.88 (d, 1H), 7.56-7.47 (m, 6H), 7.08-7.04 (m, 4H), 6.85-6.81 (m, 2H), 6.66-6.63 (m, 2H), 6.16-6.13 (m, 4H)

Additional compounds were also synthesized using appropriate intermediate materials (for example, a corresponding compound with Br-substituent group, a corresponding boron compound, and the like) in the same manner as in the above-described synthetic pathways (of Intermediate 1-7 and Intermediate 2-5), and then identified by $^1$H NMR and MS/FAB. The results are shown in Table 1.

Synthesis methods of other compounds not shown in Table 1 will also be obvious to those skilled in the art based on the above-described synthetic pathways and source materials.

TABLE 1

| Compound | ¹H NMR (CDCl₃, 400 MHz) | MS/FAB found | MS/FAB calc. |
|---|---|---|---|
| 1 | δ = 9.01-8.99 (d, 2H), 8.71-8.64 (m, 2H), 8.46 (d, 1H), 8.28-8.26 (d, 2H), 8.01-7.95 (m, 2H), 7.67-7.45 (m, 6H), 7.08-7.04 (m, 4H), 6.85-6.84 (m, 2H), 6.66-6.63 (m, 2H), 6.16-6.13 (m, 4H) | 522.21 | 521.21 |
| 2 | δ = 9.01-8.99 (m, 2H), 8.71-8.66 (m, 2H), 8.46 (s, 1H), 8.28-8.26 (d, 1H), 8.01-7.95 (m, 3H), 7.88 (m, 1H), 7.67-7.43 (m, 10H), 7.33 (d, 1H), 7.14-7.04 (m, 3H), 6.66-6.57 (m, 3H), 6.24-6.22 (m, 2H) | 572.23 | 571.23 |
| 5 | δ = 9.01-8.99 (m, 2H), 8.71-8.64 (m, 2H), 8.46 (s, 1H), 8.28-8.26 (d, 1H), 8.01-7.95 (m, 3H), 7.67-7.35 (m, 15H), 6.85-6.81 (m, 4H), 6.65-6.61 (m, 2H) | 674.28 | 673.28 |
| 18 | δ = 9.01-8.99 (d, 2H), 8.71-8.64 (m, 2H), 8.52 (s, 1H), 8.30-8.27 (d, 1H), 8.18 (s, 1H), 8.03-7.96 (m, 3H), 7.84-7.78 (m, 2H), 7.65-7.32 (m, 16H), 7.21-7.19 (m, 2H), 7.08-7.04 (m, 3H), 6.93-6.92 (d, 2H), 6.16-6.14 (dd, 2H) | 724.29 | 723.29 |
| 22 | δ = 9.01-9.00 (m, 3H), 8.75-8.69 (m, 2H), 8.50-8.48 (d, 1H), 8.36-8.34 (d, 1H), 8.13 (d, 1H), 8.01-7.96 (m, 2H), 7.78-7.76 (ss, 1H), 7.67-7.45 (m, 4H), 7.12-7.08 (m, 4H), 6.97-6.95 (d, 1H), 6.66-6.63 (m, 2H), 6.33-6.31 (m, 4H), | 523.21 | 522.21 |
| 23 | δ = 9.29 (s, 1H), 9.02 (s, 1H), 8.74-8.68 (m, 2H), 8.52-8.48 (m, 2H), 8.39 (s, 1H), 8.07-8.05 (d, 1H), 7.90-7.88 (d, 1H), 7.56-7.47 (m, 6H), 7.08-7.04 (m, 4H), 6.85-6.81 (m, 2H), 6.66-6.63 (m, 2H), 6.16-6.13 (m, 4H) | 522.21 | 521.21 |
| 27 | δ = 9.29 (s, 1H), 9.02 (s, 1H), 8.73-8.68 (m, 2H), 8.52-8.48 (m, 2H), 8.39 (s, 1H), 8.07-8.05 (s, 1H), 7.90-7.88 (d, 1H), 7.58-7.35 (m, 20H), 6.85-6.81 (m, 4H), 6.62-6.58 (m, 2H) | 674.28 | 673.28 |
| 29 | δ = 9.29 (m, 1H), 9.02 (m, 1H), 8.74-6.68 (m, 2H), 8.52-8.48 (m, 2H), 8.39 (m, 1H), 8.07-8.05 (m, 1H), 7.90-7.78 (m, 3H), 7.56-7.50 (m, 10H), 7.42-7.36 (m, 6H), 6.98-6.96 (m, 2H), 6.73-6.69 (m, 2H), | 702.24 | 701.24 |
| 37 | δ = 9.12 (s, 1H), 9.06 (s, 1H), 8.74-8.67 (m, 2H), 8.52-8.48 (m, 2H), 8.36 (s, 1H), 8.11-8.09 (d, 1H), 8.04-8.02 (d, 1H), 7.77-7.75 (d, 2H), 7.62-7.51 (m, 8H), 7.37-7.28 (m, 4H), 7.08-7.05 (m, 6H), 6.66-6.63 (m, 2H), 6.16-6.13 (m, 4H) | 698.28 | 697.28 |
| 38 | δ = 9.32 (m, 1H), 9.02 (m, 1H), 8.74-8.67 (m, 2H), 8.52-8.48 (m, 3H), 8.17 (s, 1H), 8.06-8.03 (ss, 1H), 7.96-7.94 (ss, 1H), 7.84-7.75 (m, 2H), 7.56-7.48 (m, 5H), 7.31-7.30 (d, 1H), 7.08-7.04 (m, 4H), 6.97-6.95 (m, 1H), 6.66-6.63 (m, 2H), 6.18-6.16 (m, 4H) | 572.23 | 571.23 |

Example 1

A 15 Ω/cm² ITO glass substrate (having a thickness of 1,200 Å, available from Corning) was cut to a size of 50 mm×50 mm×0.7 mm and then sonicated in isopropyl alcohol and deionized water each for five minutes, and then cleaned by irradiation of ultraviolet rays for 30 minutes and exposure to ozone. The resulting glass substrate with or as an ITO anode was mounted into a vacuum deposition device.

2-TNATA was vacuum-deposited on the ITO anode of the glass substrate to form an HIL having a thickness of 600 Å, and Compound 1 of Synthesis Example 1 was vacuum-deposited as a hole transport compound to form a HTL having a thickness of about 300 Å.

Next, 9,10-di(naphthalen-2-yl)anthracene (hereinafter, "ADN") as a blue fluorescent host and N,N,N',N'-tetraphenyl-pyrene-1,6-diamine (hereinafter, "TPD") as a blue fluorescent dopant were co-deposited on the HTL in a weight ratio of about 98:2 to form an EML having a thickness of about 300 Å.

Alq₃ was deposited on the EML to form an ETL having a thickness of about 300 Å. Subsequently, LiF as a halogenated alkali metal was deposited on the ETL to form an EIL having a thickness of about 10 Å, and then Al was vacuum-deposited on the EIL to form a cathode having a thickness of about 3,000 Å, thus resulting in a LiF/Al electrode (cathode), thereby manufacturing an organic light-emitting device.

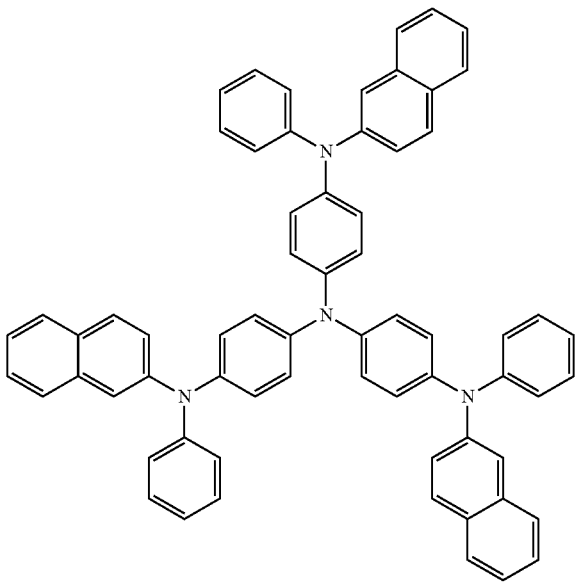

2-TNATA

-continued

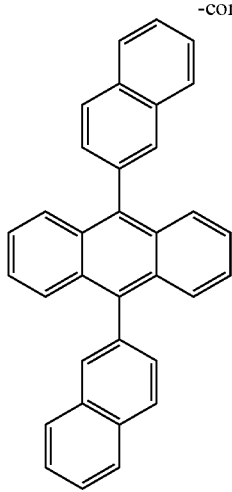

ADN

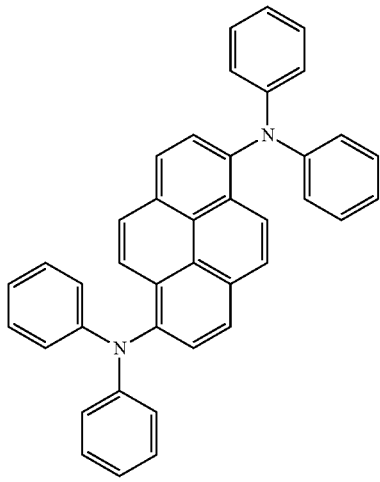

TPD

Example 2

An organic light-emitting device was manufactured in the same manner as in Example 1, except that Compound 2, instead of Compound 1, was used to form the HTL.

Example 3

An organic light-emitting device was manufactured in the same manner as in Example 1, except that Compound 5, instead of Compound 1, was used to form the HTL.

Example 4

An organic light-emitting device was manufactured in the same manner as in Example 1, except that Compound 18, instead of Compound 1, was used to form the HTL.

Example 5

An organic light-emitting device was manufactured in the same manner as in Example 1, except that Compound 22, instead of Compound 1, was used to form the HTL.

Example 6

An organic light-emitting device was manufactured in the same manner as in Example 1, except that Compound 23, instead of Compound 1, was used to form the HTL.

Example 7

An organic light-emitting device was manufactured in the same manner as in Example 1, except that Compound 27, instead of Compound 1, was used to form the HTL.

Example 8

An organic light-emitting device was manufactured in the same manner as in Example 1, except that Compound 29, instead of Compound 1, was used to form the HTL.

Example 9

An organic light-emitting device was manufactured in the same manner as in Example 1, except that Compound 37, instead of Compound 1, was used to form the HTL.

Example 10

An organic light-emitting device was manufactured in the same manner as in Example 1, except that Compound 38, instead of Compound 1, was used to form the HTL.

Comparative Example 1

An organic light-emitting device was manufactured in the same manner as in Example 1, except that NPB, instead of Compound 1, was used to form the HTL.

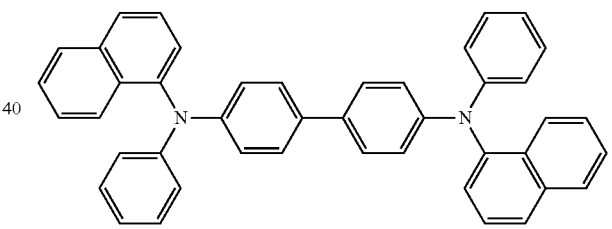

NPB

Comparative Example 2

An organic light-emitting device was manufactured in the same manner as in Example 1, except that Compound A13, instead of Compound 1, was used to form the HTL.

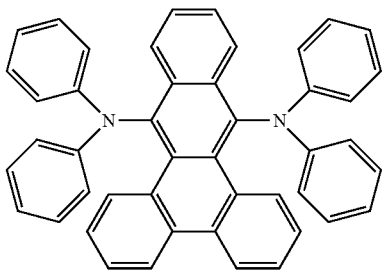

A13

Characteristics of the organic light-emitting devices of Examples 1 to 10 and Comparative Examples 1 and 2 are shown in Table 2.

TABLE 2

| Example | HTL material | Driving voltage (V) | Current density (mA/cm$^2$) | Luminance (cd/m$^2$) | Efficiency (cd/A) | Emission color | Half-life span (hr @100 mA/cm$^2$) |
|---|---|---|---|---|---|---|---|
| Example 1 | Compound 1 | 5.58 | 50 | 3090 | 6.18 | blue | 295 hr |
| Example 2 | Compound 2 | 5.45 | 50 | 3095 | 6.19 | blue | 298 hr |
| Example 3 | Compound 5 | 5.60 | 50 | 3072 | 6.14 | blue | 302 hr |
| Example 4 | Compound 18 | 5.55 | 50 | 3095 | 6.19 | blue | 290 hr |
| Example 5 | Compound 22 | 5.54 | 50 | 3101 | 6.20 | blue | 305 hr |
| Example 6 | Compound 23 | 5.49 | 50 | 3150 | 6.30 | blue | 315 hr |
| Example 7 | Compound 27 | 5.33 | 50 | 3172 | 6.34 | blue | 319 hr |
| Example 8 | Compound 29 | 5.35 | 50 | 3169 | 6.34 | blue | 328 hr |
| Example 9 | Compound 37 | 5.25 | 50 | 3177 | 6.35 | blue | 306 hr |
| Example 10 | Compound 38 | 5.48 | 50 | 3205 | 6.4 | blue | 295 hr |
| Comparative Example 1 | NPB | 7.01 | 50 | 2645 | 5.29 | blue | 258 hr |
| Comparative Example 2 | A13 | 7.33 | 50 | 2690 | 5.38 | blue | 207 hr |

Referring to Table 2, the organic light-emitting devices of Examples 1 to 10 (including a compound of Formula 1 in the HTL) were found to have a reduced driving voltage and improved efficiency and lifetime characteristics.

As described above, according to the one or more of the above embodiments, an organic light-emitting device with a high efficiency, low voltage, high luminance, and long lifespan may be manufactured using a compound of Formula 1.

The embodiments may provide a compound as a hole transport material that may provide an improved efficiency, low voltage, high luminance, and improved long lifetime characteristics, and an organic light-emitting device including the compound.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound represented by Formula 2 or Formula 3:

<Formula 2>

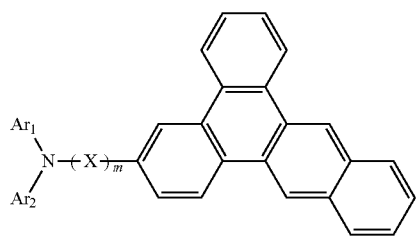

<Formula 3>

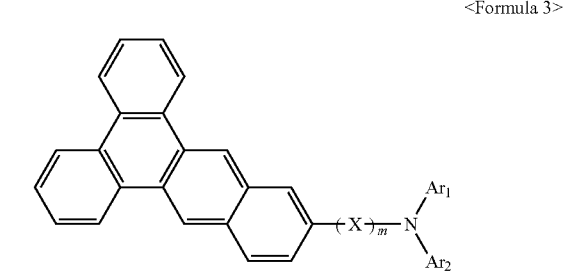

wherein, in Formula 2 and Formula 3,

X is selected from a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

m is an integer of 1 to 3, a plurality of Xs being the same or different when m is 2 or 3; and $Ar_1$ and $Ar_2$ are each independently selected from a substituted or unsubstituted $C_1$-$C_{60}$ heteroaryl group and a substituted or unsubstituted monovalent non-aromatic condensed heteropolycyclic group, wherein at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ arylene group, the substituted $C_6$-$C_{60}$ aryloxy group, the substituted $C_6$-$C_{60}$ arylthio group, the substituted $C_1$-$C_{60}$ heteroaryl group, the substituted $C_1$-$C_{60}$ heteroarylene group, the substituted monovalent non-aromatic condensed heteropolycyclic group, the substituted divalent non-aromatic condensed polycyclic group, and the substituted divalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group, a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{10}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_6$)($Q_{17}$), a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, and a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{10}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$), wherein $Q_{11}$ to $Q_{17}$ and $Q_{21}$ to $Q_{27}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The compound as claimed in claim 1, wherein X is a substituted or unsubstituted $C_6$-$C_{60}$ arylene group or a substituted or unsubstituted $C_1$-$C_{60}$ heteroarylene group.

3. The compound as claimed in claim 1, wherein X is a group represented by one of Formulae 2a, 2b, and 2c:

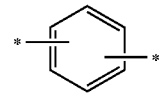

2a

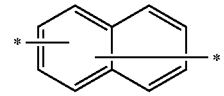

2b

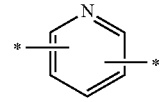

2c wherein, in Formulae 2a, 2b, and 2c, * indicates a binding site to an adjacent atom.

4. The compound as claimed in claim 1, wherein, in Formula 2 and Formula 3, $Ar_1$ and $Ar_2$ are each independently a substituted or unsubstituted $C_1$-$C_{60}$ heteroaryl group.

5. The compound as claimed in claim 1, wherein, in Formula 2 and Formula 3, $Ar_1$ and $Ar_2$ are each independently a group represented by Formula 3b:

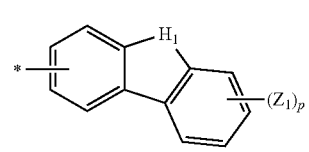

3b wherein, in Formula 3b,
$H_1$ is O or S;
$Z_1$ is selected from a hydrogen, a deuterium, a substituted or unsubstituted C1-C20 alkyl group, a substituted or unsubstituted C6-C20 aryl group, a substituted or unsubstituted C1-C20 heteroaryl group, a substituted or unsubstituted monovalent non-aromatic condensed polycyclic group, and a substituted or unsubstituted monovalent non-aromatic condensed heteropolycyclic group;
p is an integer of 1 to 7; and
* indicates a binding site to a neighboring atom.

6. The compound as claimed in claim 5, wherein $Z_1$ is a hydrogen, a deuterium, or a group represented by Formula 4a:

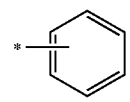

4a wherein, in Formula 4a, * indicates a binding site to a neighboring atom.

7. The compound as claimed in claim 1, wherein the compound represented by Formula 2 or Formula 3 is one of the following Compounds:

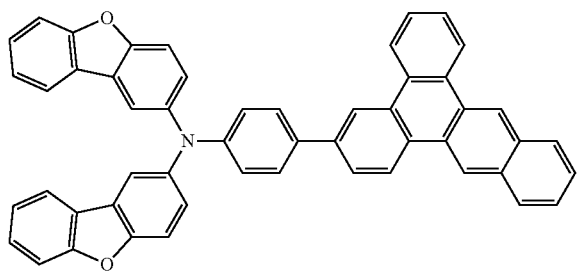

7

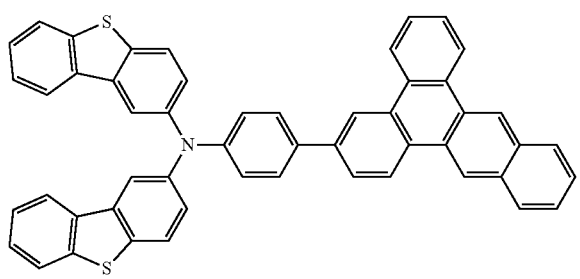

9

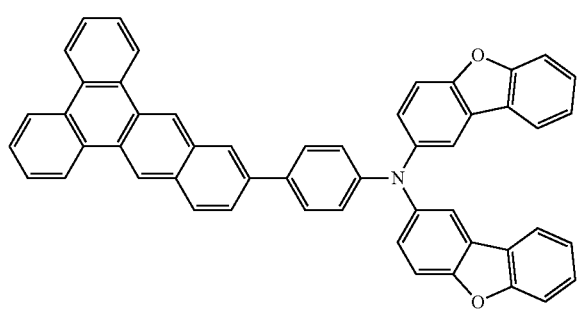

31

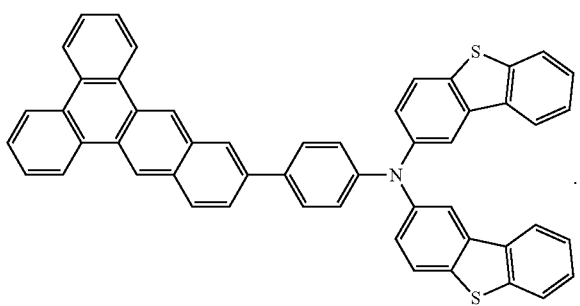

45

8. An organic light-emitting device, comprising:
a first electrode;
a second electrode disposed opposite to the first electrode; and
an organic layer between the first electrode and the second electrode, the organic layer including an emission layer,
wherein the organic layer includes the compound as claimed in claim 1.

9. The organic light-emitting device as claimed in claim 8, wherein:
the first electrode is an anode,
the second electrode is a cathode, and
the organic layer includes:

a hole transport region between the first electrode and the emission layer, the hole transport region including at least one of a hole injection layer, a hole transport layer, and an electron blocking layer, and
an electron transport region between the emission layer and the second electrode, the electron transport region including at least one of a hole blocking layer, an electron transport layer, and an electron injection layer.

10. The organic light-emitting device as claimed in claim 9, wherein the hole transport region includes the compound.

11. The organic light-emitting device as claimed in claim 9, wherein:
the hole transport region includes the hole transport layer; and
the hole transport layer includes the compound.

12. The organic light-emitting device as claimed in claim 9, wherein the hole transport region further includes a charge-generating material.

13. The organic light-emitting device as claimed in claim 12, wherein the charge-generating material includes a p-dopant.

14. The organic light-emitting device as claimed in claim 13, wherein the p-dopant includes one of a quinone derivative, a metal oxide, and a cyano group-containing compound.

15. The organic light-emitting device as claimed in claim 9, wherein the electron transport region includes a metal complex.

16. The organic light-emitting device as claimed in claim 9, wherein the electron transport region includes a Li complex.

17. The organic light-emitting device as claimed in claim 9, wherein the electron transport region includes ET-D1 or ET-D2:

ET-D1

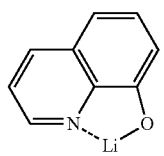

ET-D2

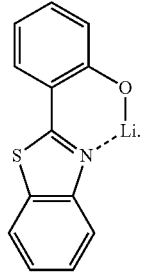

18. A display device, comprising:
a thin film transistor, the thin film transistor including a source electrode and a drain electrode; and
the organic light-emitting device as claimed in claim 8, wherein the first electrode of the organic light-emitting device is electrically connected to the source electrode or the drain electrode of the thin film transistor.

* * * * *